(12) United States Patent
Watabe et al.

(10) Patent No.: US 12,344,602 B2
(45) Date of Patent: Jul. 1, 2025

(54) ORGANIC COMPOUND, EL DEVICE, LIGHT-EMITTING APPARATUS, ELECTRONIC APPLIANCE, LIGHTING DEVICE, AND ELECTRONIC DEVICE

(71) Applicant: SEMICONDUCTOR ENERGY LABORATORY CO., LTD., Atsugi (JP)

(72) Inventors: Takeyoshi Watabe, Kanagawa (JP); Tomohiro Kubota, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 1087 days.

(21) Appl. No.: 17/292,742

(22) PCT Filed: Nov. 12, 2019

(86) PCT No.: PCT/IB2019/059683
§ 371 (c)(1),
(2) Date: May 11, 2021

(87) PCT Pub. No.: WO2020/100013
PCT Pub. Date: May 22, 2020

(65) Prior Publication Data
US 2021/0395245 A1    Dec. 23, 2021

(30) Foreign Application Priority Data
Nov. 16, 2018  (JP) .................. 2018-215717

(51) Int. Cl.
| | | |
|---|---|---|
| H01L 51/54 | (2006.01) | |
| C07D 471/00 | (2006.01) | |
| H10K 85/60 | (2023.01) | |
| H10K 50/17 | (2023.01) | |

(52) U.S. Cl.
CPC ....... C07D 471/00 (2013.01); H10K 85/6572 (2023.02); H10K 50/17 (2023.02)

(58) Field of Classification Search
None
See application file for complete search history.

(56) References Cited

U.S. PATENT DOCUMENTS

| | | | |
|---|---|---|---|
| 6,762,553 | B1 | 7/2004 | Yokogawa et al. |
| 8,283,002 | B2 | 10/2012 | Brown et al. |
| 10,700,283 | B2 | 6/2020 | Nakaie et al. |
| 10,840,452 | B2 | 11/2020 | Funyuu et al. |
| 2009/0167156 | A1 | 7/2009 | Kawamura et al. |
| 2010/0171417 | A1 | 7/2010 | Kitamura et al. |
| 2010/0292399 | A1 | 11/2010 | Brown et al. |
| 2010/0301744 | A1 | 12/2010 | Osaka et al. |
| 2012/0080667 | A1 | 4/2012 | Nowatari et al. |
| 2012/0235197 | A1 | 9/2012 | Okuyama |
| 2013/0075670 | A1 | 3/2013 | Brown et al. |
| 2015/0008409 | A1 | 1/2015 | Ito et al. |
| 2015/0041795 | A1 | 2/2015 | Suzuki et al. |
| 2015/0194621 | A1 | 7/2015 | Nishimura et al. |
| 2015/0372258 | A1 | 12/2015 | Mizuno |
| 2016/0093678 | A1 | 3/2016 | Seo et al. |
| 2016/0301011 | A1 | 10/2016 | Nakaie et al. |
| 2019/0027689 | A1 | 1/2019 | Funyuu et al. |
| 2021/0078934 | A1 | 3/2021 | Endo |
| 2021/0257562 | A1 | 8/2021 | Watabe et al. |

FOREIGN PATENT DOCUMENTS

| | | |
|---|---|---|
| CN | 105793233 A | 7/2016 |
| CN | 106132917 A | 11/2016 |
| CN | 108431985 A | 8/2018 |
| EP | 3053910 A | 8/2016 |
| EP | 3124466 A | 2/2017 |
| EP | 3401973 A | 11/2018 |
| EP | 3731290 A | 10/2020 |
| JP | 2007-242927 A | 9/2007 |
| JP | 2008-270225 A | 11/2008 |
| JP | 2012-509278 | 4/2012 |
| JP | 2013-051155 A | 3/2013 |
| JP | 2013-124271 A | 6/2013 |

(Continued)

OTHER PUBLICATIONS

Hladka.I et al., "Polymorphism of derivatives of tert-butyl substituted acridan and perfluorobiphenyl as sky-blue OLED emitters exhibiting aggregation induced thermally activated delayed fluorescence", J. Mater. Chem. C(Journal of Materials Chemistry C), Oct. 25, 2018, vol. 6, No. 48, pp. 13179-13189.

International Search Report (Application No. PCT/IB2019/059683) dated Feb. 25, 2020.

Written Opinion (Application No. PCT/IB2019/059683) dated Feb. 25, 2020.

Lee.J et al., "Synergetic electrode architecture for efficient graphene-based flexible organic light-emitting diodes", Nature Communications, Jun. 2, 2016, vol. 7, pp. 11791-1-11791-9.

(Continued)

Primary Examiner — Andrew K Bohaty
(74) Attorney, Agent, or Firm — Fish & Richardson P.C.

(57) ABSTRACT

An object is to provide an organic compound with a low refractive index. Alternatively, a novel organic compound with a low refractive index and an electron-donating property is provided. Alternatively, an EL device with high emission efficiency is provided. An organic compound having an arylamine skeleton including a fluorine atom or an acridine skeleton including a fluorine atom and an EL device using the organic compound are provided. The EL device preferably includes a hole-injection layer containing the organic compound having an arylamine skeleton including a fluorine atom or an acridine skeleton including a fluorine atom and a substance showing an electron-accepting property with respect to the organic compound.

11 Claims, 27 Drawing Sheets

(56) References Cited

FOREIGN PATENT DOCUMENTS

| JP | 2013-172071 A | | 9/2013 | |
|---|---|---|---|---|
| JP | 2014-032851 A | | 2/2014 | |
| JP | 2019-135774 A | | 8/2019 | |
| KR | 2011-0087283 A | | 8/2011 | |
| KR | 2011-0107682 A | | 10/2011 | |
| KR | 2014020208 A | * | 2/2014 | ........... C07D 405/10 |
| KR | 2016-0067925 A | | 6/2016 | |
| KR | 2016-0140763 A | | 12/2016 | |
| KR | 2018-0090363 A | | 8/2018 | |
| TW | 201524955 | | 7/2015 | |
| TW | 201600493 | | 1/2016 | |
| TW | 201736336 | | 10/2017 | |
| WO | WO-2010/059646 | | 5/2010 | |
| WO | WO-2015/050253 | | 4/2015 | |
| WO | WO-2015/146965 | | 10/2015 | |
| WO | WO-2017/119483 | | 7/2017 | |
| WO | WO-2019/124415 | | 6/2019 | |

OTHER PUBLICATIONS

Shin.H et al., "Sky-Blue Phosphorescent OLEDs with 34.1% External Quantum Efficiency Using a Low Refractive Index Electron Transporting Layer", Adv. Mater. (Advanced Materials), Jun. 22, 2016, vol. 28, No. 24, pp. 4920-4925.

Fuchs.C et al., "Enhanced light emission from top-emitting organic light-emitting diodes by optimizing surface plasmon polariton losses", Phys. Rev. B (Physical Review. B), Dec. 11, 2015, vol. 92, pp. 245306-1-245306-10.

* cited by examiner

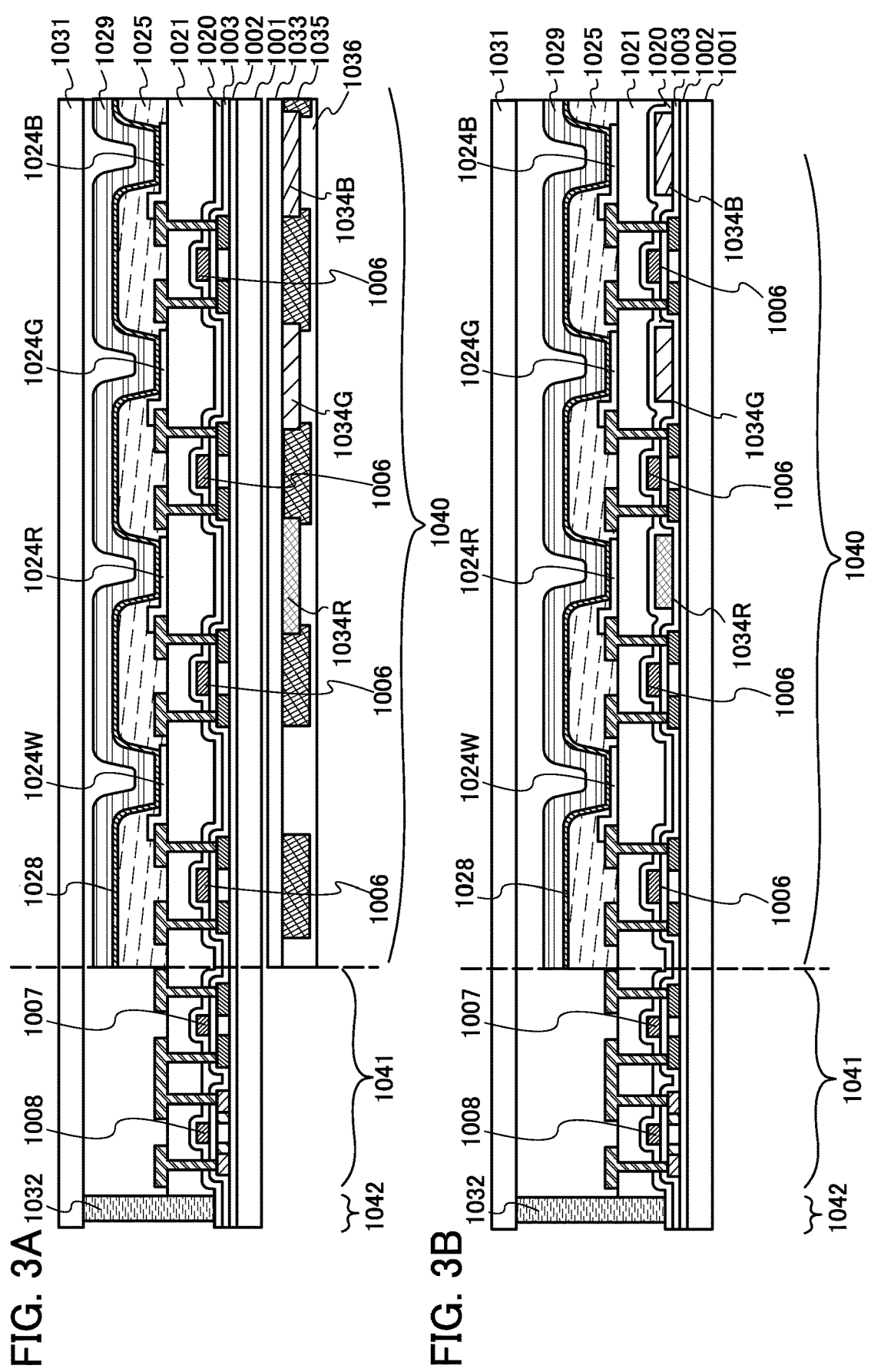

FIG. 7A
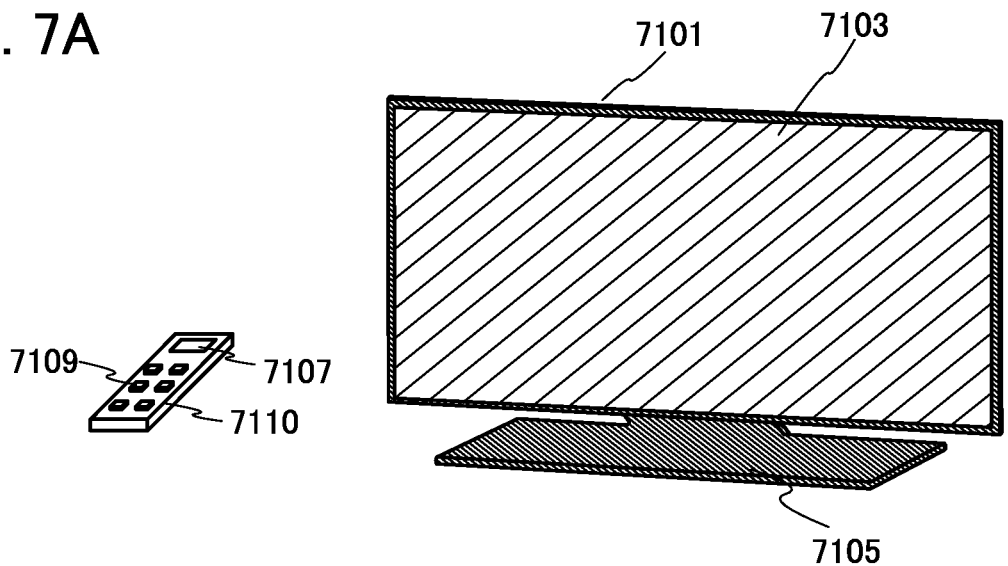
FIG. 7B1
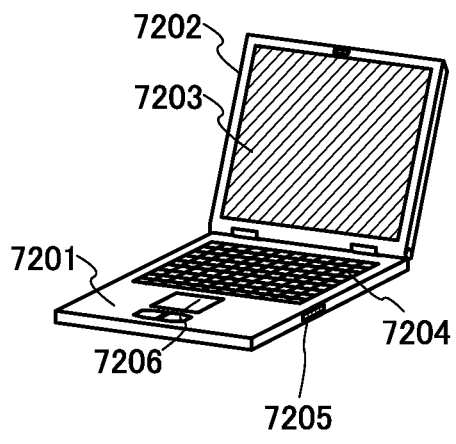
FIG. 7B2
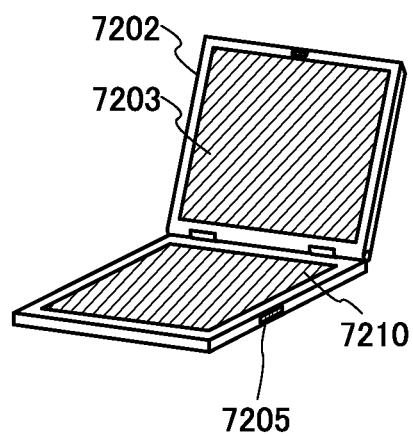
FIG. 7C
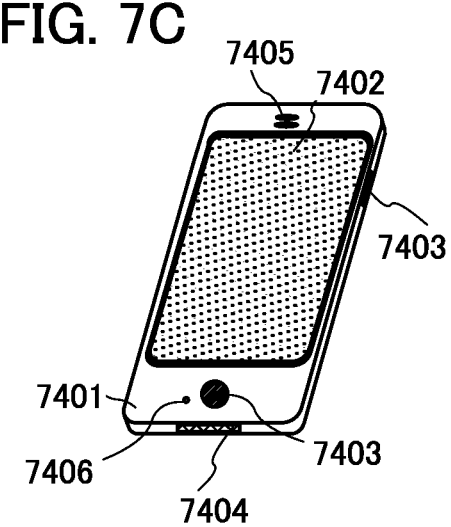

ORGANIC COMPOUND, EL DEVICE, LIGHT-EMITTING APPARATUS, ELECTRONIC APPLIANCE, LIGHTING DEVICE, AND ELECTRONIC DEVICE

CROSS REFERENCE TO RELATED APPLICATIONS

This application is a U.S. National Phase Application under 35 U.S.C. § 371 of International Application PCT/IB2019/059683, filed on Nov. 12, 2019, which is incorporated by reference and claims the benefit of a foreign priority application filed in Japan on Nov. 16, 2018, as Application No. 2018-215717.

TECHNICAL FIELD

One embodiment of the present invention relates to an organic compound, an EL device, a display module, a lighting module, a display device, a light-emitting apparatus, an electronic appliance, a lighting device, and an electronic device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

BACKGROUND ART

Electroluminescence (EL) devices (organic EL devices) including organic compounds and utilizing EL have been put into practical use. In the basic structure of such EL devices, an organic compound layer containing a light-emitting material (an EL layer) is interposed between a pair of electrodes. Carriers are injected by application of voltage to the element, and recombination energy of the carriers is used, whereby light emission can be obtained from the light-emitting material.

Such EL devices are of self-light-emitting type, and have advantages over liquid crystal, such as high visibility and no need for backlight when used for pixels of a display; accordingly, the EL devices are suitable as flat panel display elements. Displays using such EL devices are also highly advantageous in that they can be fabricated thin and lightweight. Moreover, an extremely fast response speed is also a feature.

Since light-emitting layers of such EL devices can be successively formed two-dimensionally, planar light emission can be achieved. This feature is difficult to realize with point light sources typified by incandescent lamps and LEDs or linear light sources typified by fluorescent lamps; thus, the EL devices also have great potential as planar light sources, which can be applied to lighting and the like.

Displays or lighting devices using EL devices can be suitably used for a variety of electronic appliances as described above, and research and development of EL devices have progressed for better characteristics.

Low outcoupling efficiency is often a problem in talking about an organic EL device. In particular, attenuation due to reflection caused by a difference in refractive index is a significant factor in decreasing the efficiency of the element; thus, in order to reduce the influence, a structure in which a layer containing a low refractive index material is formed in an EL layer has been proposed (e.g., see Non-Patent Document 1).

An EL device having this structure can be an EL device having higher emission efficiency than an EL device having a conventional structure; however, it is not easy to form a layer containing a low refractive index material in an EL layer without adversely affecting other critical characteristics of the EL device. This is because a low refractive index and a high carrier-transport property or reliability when the material is used for an EL device have a trade-off relation. This is because the carrier-transport property and reliability of an organic compound largely depend on an unsaturated bond, and an organic compound having many unsaturated bonds tends to have a high refractive index.

REFERENCE

[Patent Document]
[Non-Patent Document 1] Jaeho Lee and 12 others, "Synergetic electrode architecture for efficient graphene-based flexible organic light-emitting diodes", nature COMMUNICATIONS, Jun. 2, 2016, DOI: 10.1038/ncomms 11791.

SUMMARY OF THE INVENTION

Problems to be Solved by the Invention

An object of one embodiment of the present invention is to provide a novel organic compound. Another object of one embodiment of the present invention is to provide an organic compound with a low refractive index. Another object of one embodiment of the present invention is to provide a novel organic compound with a low refractive index and a high electron-donating property.

An object of another embodiment of the present invention is to provide an EL device with high emission efficiency. Another object of one embodiment of the present invention is to provide an EL device, a light-emitting apparatus, an electronic appliance, a display device, and an electronic device each with low power consumption.

Note that the description of the effects does not preclude the existence of other effects. One embodiment of the present invention does not need to have all these effects. Effects other than these will be apparent from the description of the specification, the drawings, the claims, and the like and effects other than these can be derived from the description of the specification, the drawings, the claims, and the like.

It is only necessary that at least one of the above-described objects be achieved in the present invention.

Means for Solving the Problems

One embodiment of the present invention is an EL device including an anode, a cathode, and an EL layer positioned between the anode and the cathode. The EL layer includes a first layer; the first layer contains a first substance and a second substance; the first substance is a substance showing an electron-donating property with respect to the second substance; the first substance has an arylamine skeleton or an acridine skeleton; and a fluorine atom is included in the first substance.

Alternatively, another embodiment of the present invention is an EL device including an anode, a cathode, and an EL layer positioned between the anode and the cathode. The EL layer includes a first layer; the first layer contains a first substance and a second substance; the first substance is a substance showing an electron-donating property with respect to the second substance; the first substance has an arylamine skeleton or an acridine skeleton; the first substance includes one or a plurality of aromatic rings where a lone electron pair of a nitrogen atom in the arylamine skeleton or the acridine skeleton can conjugate; and a fluorine atom is bonded to one or two of the aromatic rings.

Alternatively, another embodiment of the present invention is the EL device in the above structure, in which a fluorine atom is bonded to one of the aromatic rings.

Alternatively, another embodiment of the present invention is the EL device in the above structure, in which the refractive index of the first substance is less than or equal to 1.8.

Alternatively, another embodiment of the present invention is the EL device in the above structure, in which the EL layer includes a hole-injection layer and a light-emitting layer; the light-emitting layer is provided between the hole-injection layer and the cathode; the hole-injection layer is provided in contact with the anode; and the first layer is the hole-injection layer.

Alternatively, another embodiment of the present invention is the EL device in the above structure, in which the EL layer includes a plurality of light-emitting units and a charge-generation layer provided between the plurality of light-emitting units; and the first layer is the charge generation layer.

Alternatively, another embodiment of the present invention is the EL device in the above structure, in which the EL layer further includes a second layer; the second layer contains a third substance and a fourth substance; the third substance is a substance showing an electron-donating property with respect to the fourth substance; the third substance is an organic compound having an arylamine skeleton or an acridine skeleton; and a fluorine atom is included in the third substance.

Alternatively, another embodiment of the present invention is the EL device in the above structure, in which the EL layer further includes a second layer; the second layer contains a third substance and a fourth substance; the third substance is a substance showing an electron-donating property with respect to the fourth substance; the third substance is an organic compound having an arylamine skeleton or an acridine skeleton; the first substance includes one or a plurality of aromatic rings where a lone electron pair of a nitrogen atom in the arylamine skeleton or the acridine skeleton can conjugate; and a fluorine atom is bonded to one or two of the aromatic rings.

Alternatively, another embodiment of the present invention is the EL device in the above structure, in which the refractive index of the third substance is less than or equal to 1.8.

Alternatively, another embodiment of the present invention is the EL device in which among the plurality of light-emitting units, a light-emitting unit closest to the anode side includes a hole-injection layer in contact with the anode; and the second layer is the hole-injection layer.

Alternatively, another embodiment of the present invention is the EL device in the above structure, in which the first substance is the same substance as the third substance; and the second substance is the same substance as the fourth substance.

Alternatively, another embodiment of the present invention is the EL device in the above structure, in which five or more fluorine atoms are included in the organic compound.

Alternatively, another embodiment of the present invention is the EL device in the above structure, in which the proportion of fluorine atoms included in the organic compound is higher than or equal to 7 atomic % and lower than or equal to 40 atomic %.

Alternatively, another embodiment of the present invention is the EL device in the above structure, in which the aromatic ring to which a fluorine atom is bonded is a benzene ring or a naphthalene ring.

Alternatively, another embodiment of the present invention is the EL device in the above structure, in which the aromatic ring to which a fluorine atom is bonded is a perfluoroaryl group.

Alternatively, another embodiment of the present invention is the EL device in the above structure, in which the aromatic ring to which a fluorine atom is bonded is a perfluorophenyl group or a perfluorobiphenyl group.

Alternatively, another embodiment of the present invention is the EL device in the above structure, in which the hole-injection layer has a thickness of greater than or equal to 20 nm.

Alternatively, another embodiment of the present invention is the EL device in the above structure, in which the second substance is molybdenum oxide.

Alternatively, another embodiment of the present invention is an organic compound represented by General Formula (G1) below.

[Chemical Formula 1]

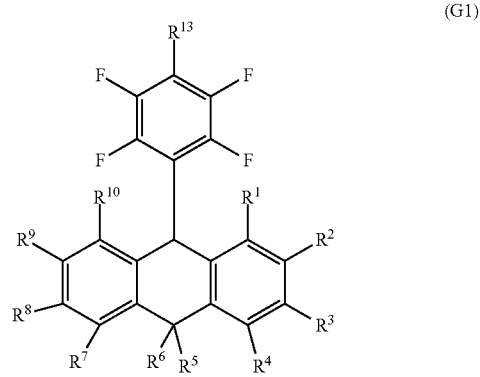

(G1)

Note that in General Formula (G1) above, $R^1$ to $R^4$ and $R^7$ to $R^{10}$ each independently represent any one of hydrogen, an alkyl group having 1 to 6 carbon atoms, and an alkyl fluoride group having 1 to 6 carbon atoms, and $R^5$ and $R^6$ each independently represent any one of hydrogen, an alkyl group having 1 to 6 carbon atoms, an alkyl fluoride group having 1 to 6 carbon atoms, and a substituted or unsubstituted phenyl group. Moreover, $R^{13}$ represents fluorine or any of groups represented by General Formula (g1) below.

[Chemical Formula 2]

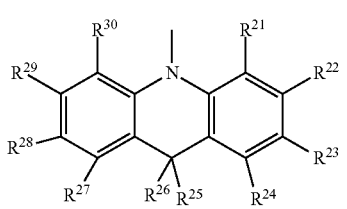

Note that in General Formula (g1) above, $R^{21}$ to $R^{24}$ and $R^{27}$ to $R^{30}$ each independently represent any one of hydrogen, an alkyl group having 1 to 6 carbon atoms, and an alkyl fluoride group having 1 to 6 carbon atoms, and $R^{25}$ and $R^{26}$ each independently represent any one of hydrogen, an alkyl group having 1 to 6 carbon atoms, an alkyl fluoride group having 1 to 6 carbon atoms, and a substituted or unsubstituted phenyl group.

Alternatively, another embodiment of the present invention is the organic compound in the above structure, in which $R^{13}$ is a group represented by the General Formula (g1).

Alternatively, another embodiment of the present invention is an organic compound represented by General Formula (G2) below.

[Chemical Formula 3]

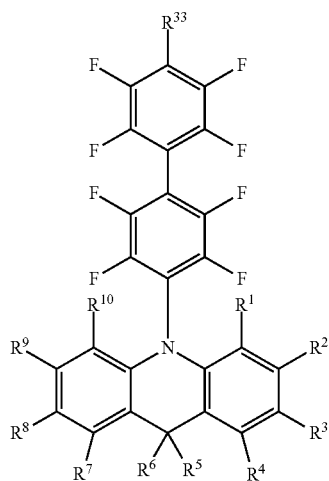

Note that in General Formula (G2) above, $R^1$ to $R^4$ and $R^7$ to $R^{10}$ each independently represent any one of hydrogen, an alkyl group having 1 to 6 carbon atoms, and an alkyl fluoride group having 1 to 6 carbon atoms, and $R^5$ and $R^6$ each independently represent any one of hydrogen, an alkyl group having 1 to 6 carbon atoms, an alkyl fluoride group having 1 to 6 carbon atoms, and a substituted or unsubstituted phenyl group. Moreover, $R^{33}$ represents fluorine or any of groups represented by General Formula (g1) below.

[Chemical Formula 4]

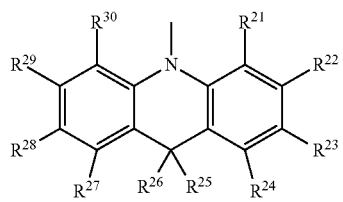

Note that in General Formula (g1) above, $R^{21}$ to $R^{24}$ and $R^{27}$ to $R^{30}$ each independently represent any one of hydrogen, an alkyl group having 1 to 6 carbon atoms, and an alkyl fluoride group having 1 to 6 carbon atoms, and $R^{25}$ and $R^{26}$ each independently represent any one of hydrogen, an alkyl group having 1 to 6 carbon atoms, an alkyl fluoride group having 1 to 6 carbon atoms, and a substituted or unsubstituted phenyl group.

Alternatively, another embodiment of the present invention is the organic compound in the above structure, in which $R^{33}$ is represented by the General Formula (g1).

Alternatively, another embodiment of the present invention is the organic compound in the above structure, in which $R^{25}$ and $R^{26}$ each represent a phenyl group.

Alternatively, another embodiment of the present invention is the organic compound in the above structure, in which $R^{21}$ to $R^{24}$ and $R^{27}$ to $R^{30}$ each represent hydrogen.

Alternatively, another embodiment of the present invention is the organic compound in the above structure, in which $R^5$ and $R^6$ each represent a phenyl group.

Alternatively, another embodiment of the present invention is the organic compound in the above structure, which is represented by Structural Formula (100) below.

[Chemical Formula 5]

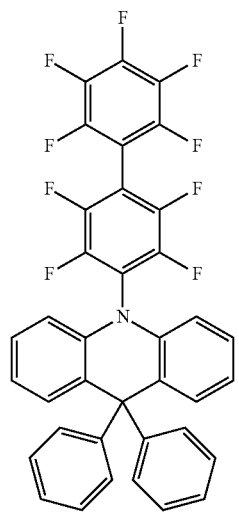

Alternatively, another embodiment of the present invention is the organic compound in the above structure, which is represented by Structural Formula (200) below.

[Chemical Formula 6]

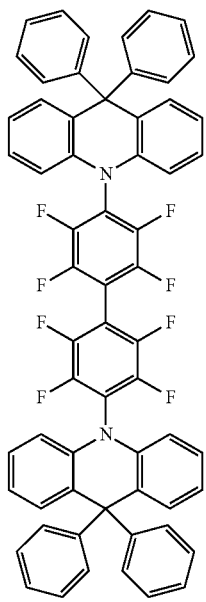

(200)

Alternatively, another embodiment of the present invention is an EL device including the organic compound represented by any one of the above.

Alternatively, another embodiment of the present invention is an EL device including the organic compound represented by any one of the above as a hole-transport material.

Alternatively, another embodiment of the present invention is an EL device including the organic compound represented by any one of the above in a hole-transport layer.

Alternatively, another embodiment of the present invention is an EL device including an anode, a cathode, and an EL layer provided between the anode and the cathode. The EL layer includes a hole-injection layer and a light-emitting layer; the light-emitting layer is positioned between the hole-injection layer and the cathode; the hole-injection layer is provided in contact with the anode; the hole-injection layer includes the organic compound represented by any one of the above and a second substance; and the organic compound is a substance showing an electron-donating property with respect to the second substance.

Alternatively, another embodiment of the present invention is the EL device in the above structure, in which the refractive index of the organic compound is less than or equal to 1.8.

Alternatively, another embodiment of the present invention is the EL device in the above structure, in which the hole-injection layer has a thickness of greater than or equal to 20 nm.

Alternatively, another embodiment of the present invention is the EL device in the above structure, in which the second substance is molybdenum oxide.

Alternatively, another embodiment of the present invention is a light-emitting apparatus including the EL device described in any one of the above, and a transistor or a substrate.

Alternatively, another embodiment of the present invention is an electronic appliance including the light-emitting apparatus, and a sensor, an operation button, a speaker, or a microphone.

Alternatively, another embodiment of the present invention is a lighting device including the light-emitting apparatus and a housing.

Alternatively, another embodiment of the present invention is an electronic device including the organic compound described in any one of the above.

Note that the light-emitting apparatus in this specification includes, in its category, an image display device that uses an EL device. The light-emitting apparatus may be included in a module in which an EL device is provided with a connector such as an anisotropic conductive film or a TCP (Tape Carrier Package), a module in which a printed wiring board is provided at the end of a TCP, and a module in which an IC (integrated circuit) is directly mounted on an EL device by a COG (Chip On Glass) method. Furthermore, in some cases, a light-emitting apparatus may be included in lighting equipment or the like.

Effect of the Invention

One embodiment of the present invention can provide a novel organic compound. Alternatively, one embodiment of the present invention can provide an organic compound with a low refractive index. Alternatively, one embodiment of the present invention can provide an organic compound with a low refractive index and a high electron-donating property.

Another embodiment of the present invention can provide an EL device with high emission efficiency. Alternatively, one embodiment of the present invention can provide an EL device, a light-emitting apparatus, an electronic appliance, a display device, and an electronic device each with low power consumption.

Note that the description of the effects does not preclude the existence of other effects. One embodiment of the present invention does not need to have all these effects. Effects other than these will be apparent from the description of the specification, the drawings, the claims, and the like and effects other than these can be derived from the description of the specification, the drawings, the claims, and the like.

BRIEF DESCRIPTION OF THE DRAWINGS

FIG. 3A and FIG. 3B are conceptual diagrams of an active matrix light-emitting apparatus.
FIG. 7A, FIG. 7B1, FIG. 7B2, and FIG. 7C are diagrams illustrating electronic appliances.

MODE FOR CARRYING OUT THE INVENTION

Figure 1A:
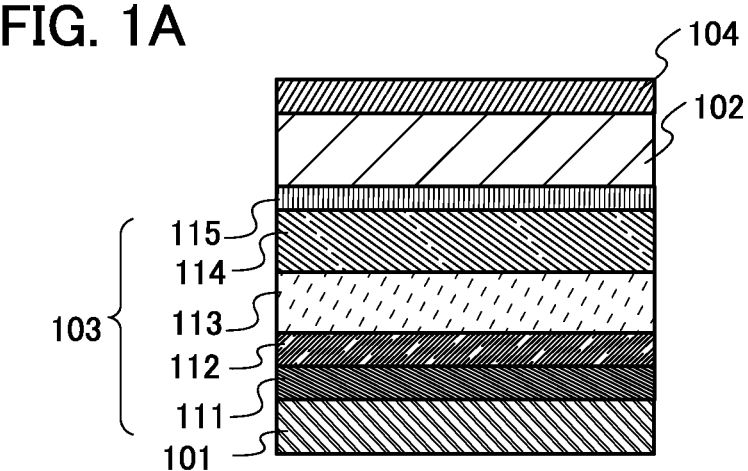
FIG. 1A to FIG. 1C are schematic diagrams of EL devices.

Embodiments of the present invention are described in detail below with reference to drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the description in the following embodiments.

Embodiment 1

An organic EL device (hereinafter, also referred to as an EL device) generally has a structure in which a layer containing an organic compound (also referred to as an EL layer), which consists of a plurality of layers having different functions such as a light-emitting layer, a carrier-transport layer, and a carrier-injection layer, is sandwiched between a pair of electrodes. A hole-injection layer and a hole-transport layer are formed between an anode and the light-emitting layer and have a function of smoothly injecting holes from the electrode into the EL layer and rapidly transporting the holes and injecting the holes into the light-emitting layer.

As reported in Non-Patent Document 1, an organic EL device including a layer having a lower refractive index than peripheral materials can have improved emission efficiency. As its name suggests, an organic EL device is an EL device using an EL layer containing an organic compound, and the refractive index of the organic compound largely depends on the atomic refraction of atoms included in the organic compound. That is, an organic compound in which the proportion of atoms with a small atomic refraction is large in atoms included in the organic compound tends to be an organic compound with a low refractive index, and an organic EL device manufactured using the organic compound can be an EL device with high emission efficiency.

Here, a fluorine atom is given as a typical example of an atom with a small atomic refraction. However, since a fluorine atom has a high electron-withdrawing property, it has been predicted that an organic compound including a large number of fluorine atoms adversely affects a hole-transport property and an electron-donating property, and thus such an organic compound has almost never been used as a hole-transport material or an electron-donating material.

However, the present inventors have found that an organic compound having an arylamine skeleton or an acridine skeleton can be suitably used as an electron-donating material even when including a fluorine atom in its molecular structure. The organic compound including fluorine with a small atomic refraction can be an organic compound with a low refractive index, and a hole-injection layer formed using the organic compound can be a layer with a low refractive index; thus, an EL device with high emission efficiency can be provided.

Note that in the organic compound having an arylamine skeleton or an acridine skeleton, a lone electron pair of nitrogen included in each of the skeletons contributes to an electron-donating property, so that the influence of an electron-withdrawing property becomes large when fluorine is substituted at an aromatic ring in a range where the lone electron pair can conjugate, which has been considered to further decrease the electron-donating property of the organic compound. However, the results of the present inventors revealed that the electron-donating property of the organic compound having an arylamine skeleton or an acridine skeleton is not significantly decreased even when fluorine is substituted at such an aromatic ring, and the organic compound can function as an electron-donating material when used together with an electron-accepting material and can be favorably used for a hole-injection layer of an EL device. Accordingly, an organic compound including a larger number of fluorine atoms in a molecule can be easily used as an electron-donating material, so that a layer with a lower refractive index can be formed in a light-emitting layer. As a result, an EL device with higher emission efficiency can be provided.

In the organic compound in which fluorine is substituted for hydrogen of the aromatic ring that exists in the range where the lone electron pair of nitrogen included in the arylamine skeleton or the acridine skeleton can conjugate, a fluorine atom is preferably bonded to one or two aromatic rings when a plurality of aromatic rings are bonded to the nitrogen, compared to the structure in which fluorine atoms are bonded to all the aromatic rings.

Moreover, the larger the proportion of fluorine atoms included in an organic compound is, the lower a refractive index can be; thus, four or more fluorine atoms are preferably bonded to the aromatic ring. It is further preferable that fluorine atoms be bonded to all positions where the fluorine atoms can be substituted for.

The aromatic ring is preferably a benzene ring or a naphthalene ring, further preferably a benzene ring.

In the organic compound, the aromatic ring that includes a fluorine atom in the range where the lone electron pair of nitrogen included in the arylamine skeleton or the acridine skeleton can conjugate is preferably one ring, in which case the electron-donating property is not too low.

Note that in the organic compound, a substituent including a fluorine atom may be bonded to the outside of the range where the lone electron pair of nitrogen included in the arylamine skeleton or the acridine skeleton can conjugate. Examples of the substituent including a fluorine atom include an alkyl fluoride group and an aryl fluoride group, and the aryl fluoride group is preferable. Among them, an aryl group including five or more fluorine atoms, in particular, a perfluoroaryl group, which includes a large number of fluorine atoms, is favorable because an organic compound with a lower refractive index can be obtained. Note that an organic compound including a fluorine atom in an aromatic ring where a lone electron pair of nitrogen in an arylamine skeleton or an acridine skeleton can conjugate and also including a fluorine atom outside the range is further preferable because the proportion of fluorine atoms in a molecule is high and a refractive index can be further lowered.

It is also a major feature of an EL device using the above organic compound as an electron-donating material that while emission efficiency is improved, main characteristics other than the emission efficiency (e.g., a driving voltage and a lifetime) can be kept favorable as in an EL device using an organic compound not including a fluorine atom.

That is, the present inventors have found an organic compound with a low refractive index, which includes a large amount of fluorine atoms having a high electron-withdrawing property and maintains a favorable electron-donating property, and have achieved an EL device with favorable emission efficiency using the organic compound. In particular, in the case where the organic compound is a first substance and a substance with respect to which the first substance shows an electron-donating property is a second substance, an EL device using a layer containing the first substance and the second substance as a hole-injection layer or an intermediate layer (charge-generation layer) of a tandem element can be an EL device in which not only emission efficiency but also main characteristics other than the emission efficiency (e.g., a driving voltage and a lifetime) are improved.

Note that when the proportion of fluorine atoms in the molecule of the organic compound (the first substance) is higher than 40 atomic %, the electron-donating property is too low and a function of a donor material is lowered; thus, the proportion of fluorine atoms is preferably lower than or equal to 40 atomic %. Furthermore, in order to achieve a low refractive index, the proportion of fluorine atoms included in the organic compound is preferably higher than or equal to 7 atomic %.

A specific example of part of a preferred embodiment of the above organic compound (the first substance) can be represented by the following general formula.

[Chemical Formula 7]

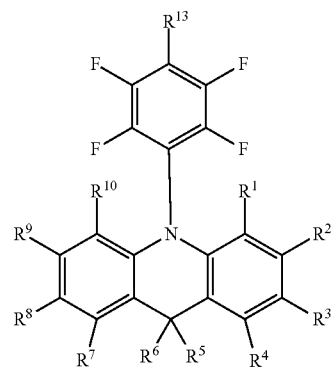

(G1)

Note that in General Formula (G1) above, $R^1$ to $R^4$ and $R^7$ to $R^{10}$ each independently represent any one of hydrogen, an alkyl group having 1 to 6 carbon atoms, and an alkyl fluoride group having 1 to 6 carbon atoms, and $R^5$ and $R^6$ each independently represent any one of hydrogen, an alkyl group having 1 to 6 carbon atoms, an alkyl fluoride group having 1 to 6 carbon atoms, and a substituted or unsubstituted phenyl group. Moreover, $R^{13}$ represents fluorine or any of groups represented by General Formula (g1) below.

[Chemical Formula 8]

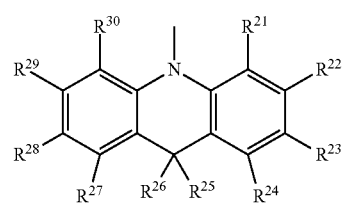

(g1)

Note that in General Formula (g1) above, $R^{21}$ to $R^{24}$ and $R^{27}$ to $R^{30}$ each independently represent any one of hydrogen, an alkyl group having 1 to 6 carbon atoms, and an alkyl fluoride group having 1 to 6 carbon atoms, and $R^{25}$ and $R^{26}$ each independently represent any one of hydrogen, an alkyl group having 1 to 6 carbon atoms, an alkyl fluoride group having 1 to 6 carbon atoms, and a substituted or unsubstituted phenyl group.

Note that in the organic compound represented by General Formula (G1) above, $R^{13}$ preferably represents fluorine to obtain an organic compound with a lower refractive index, or preferably represents the group represented by General Formula (g1) above to add a higher electron-donating property to the organic compound.

The organic compound of one embodiment of the present invention can also be represented by General Formula (G2) below.

[Chemical Formula 9]

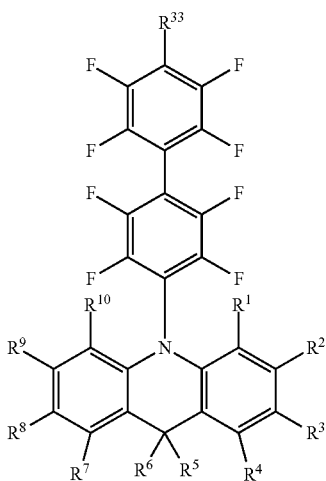

(G2)

Note that in General Formula (G2) above, $R^1$ to $R^4$ and $R^7$ to $R^{10}$ each independently represent any one of hydrogen, an alkyl group having 1 to 6 carbon atoms, and an alkyl fluoride group having 1 to 6 carbon atoms, and $R^5$ and $R^6$ each independently represent any one of hydrogen, an alkyl group having 1 to 6 carbon atoms, an alkyl fluoride group having 1 to 6 carbon atoms, and a substituted or unsubstituted phenyl group. Moreover, $R^{33}$ represents fluorine or any of groups represented by General Formula (g1) above.

[Chemical Formula 10]

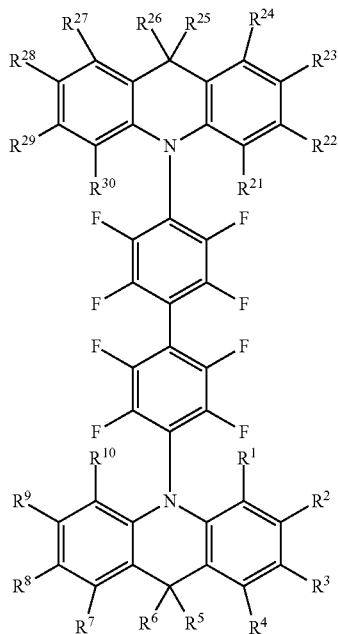

(G3)

Note that in General Formula (G3) above, $R^1$ to $R^4$ and $R^7$ to $R^{10}$ each independently represent any one of hydrogen, an alkyl group having 1 to 6 carbon atoms, and an alkyl fluoride group having 1 to 6 carbon atoms, and $R^5$ and $R^6$ each independently represent any one of hydrogen, an alkyl group having 1 to 6 carbon atoms, an alkyl fluoride group having 1 to 6 carbon atoms, and a substituted or unsubstituted phenyl group. In addition, $R^{21}$ to $R^{24}$ and $R^{27}$ to $R^{30}$ each independently represent any one of hydrogen, an alkyl group having 1 to 6 carbon atoms, and an alkyl fluoride group having 1 to 6 carbon atoms, and $R^{25}$ and $R^{26}$ each independently represent any one of hydrogen, an alkyl group having 1 to 6 carbon atoms, an alkyl fluoride group having 1 to 6 carbon atoms, and a substituted or unsubstituted phenyl group.

Note that in the organic compound represented by General Formula (G2) above, $R^{33}$ preferably represents fluorine to obtain an organic compound with a lower refractive index. That is, one preferred embodiment of the present invention is an organic compound represented by General Formula (G4) below.

[Chemical Formula 11]

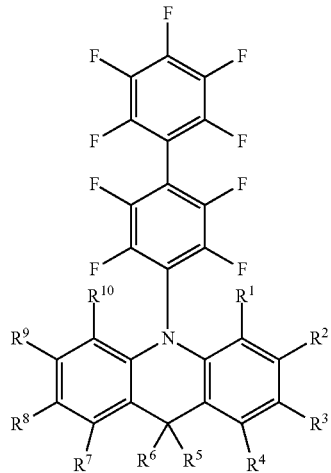

(G4)

Note that in General Formula (G4) above, $R^1$ to $R^4$ and $R^7$ to $R^{10}$ each independently represent any one of hydrogen, an alkyl group having 1 to 6 carbon atoms, and an alkyl fluoride group having 1 to 6 carbon atoms, and $R^5$ and $R^6$ each independently represent any one of hydrogen, an alkyl group having 1 to 6 carbon atoms, an alkyl fluoride group having 1 to 6 carbon atoms, and a substituted or unsubstituted phenyl group.

Note that in the organic compound represented by General Formula (G2) above, $R^{33}$ is preferably represented by General Formula (g1) above to add a higher electron-donating property to the organic compound. That is, one preferred embodiment of the present invention is the organic compound represented by General Formula (G3) above.

Note that in the organic compounds represented by General Formula (G1) to General Formula (G4) above, $R^5$ and $R^6$ each preferably represent a substituted or unsubstituted phenyl group, particularly an unsubstituted phenyl group to increase a glass transition temperature (Tg) and maintain the heat resistance of an EL device. For the same reason, in General Formula (G1) or General Formula (G3) above, $R^{25}$ or $R^{26}$ preferably represents a substituted or unsubstituted phenyl group, particularly an unsubstituted phenyl group.

In the organic compounds represented by General Formula (G1) to General Formula (G4) above, $R^2$ and $R^9$ each preferably represent hydrogen to maintain a low refractive index. For the same reason, in General Formula (G1) or General Formula (G3) above, $R^{22}$ or $R^{29}$ preferably represents hydrogen.

In the organic compounds represented by General Formula (G1) to General Formula (G4) above, $R^1$ to $R^4$ and $R^7$ to $R^{10}$ each preferably represent hydrogen to maintain a low refractive index. For the same reason, in General Formula (G1) or General Formula (G3) above, $R^{21}$ to $R^{24}$ and $R^{27}$ to $R^{30}$ each preferably represent hydrogen.

Specific examples of the alkyl group having 1 to 6 carbon atoms and the alkyl fluoride group having 1 to 6 carbon atoms in each of the organic compounds represented by General Formula (G1) to General Formula (G4) above include groups represented by Formula (1-1) to Formula (1-23) below, and the like. In the case where the substituted or unsubstituted phenyl group has a substituent, a fluoro group, a phenyl group, a dibenzothiophenyl group, a carbazolyl group, a fluorenyl group, a dimethylfluorenyl group, a diphenyltriazinyl group, or the like as well as the group represented by any of Formula (1-1) to Formula (1-23) below can be used as the substituent.

[Chemical Formulae 12]

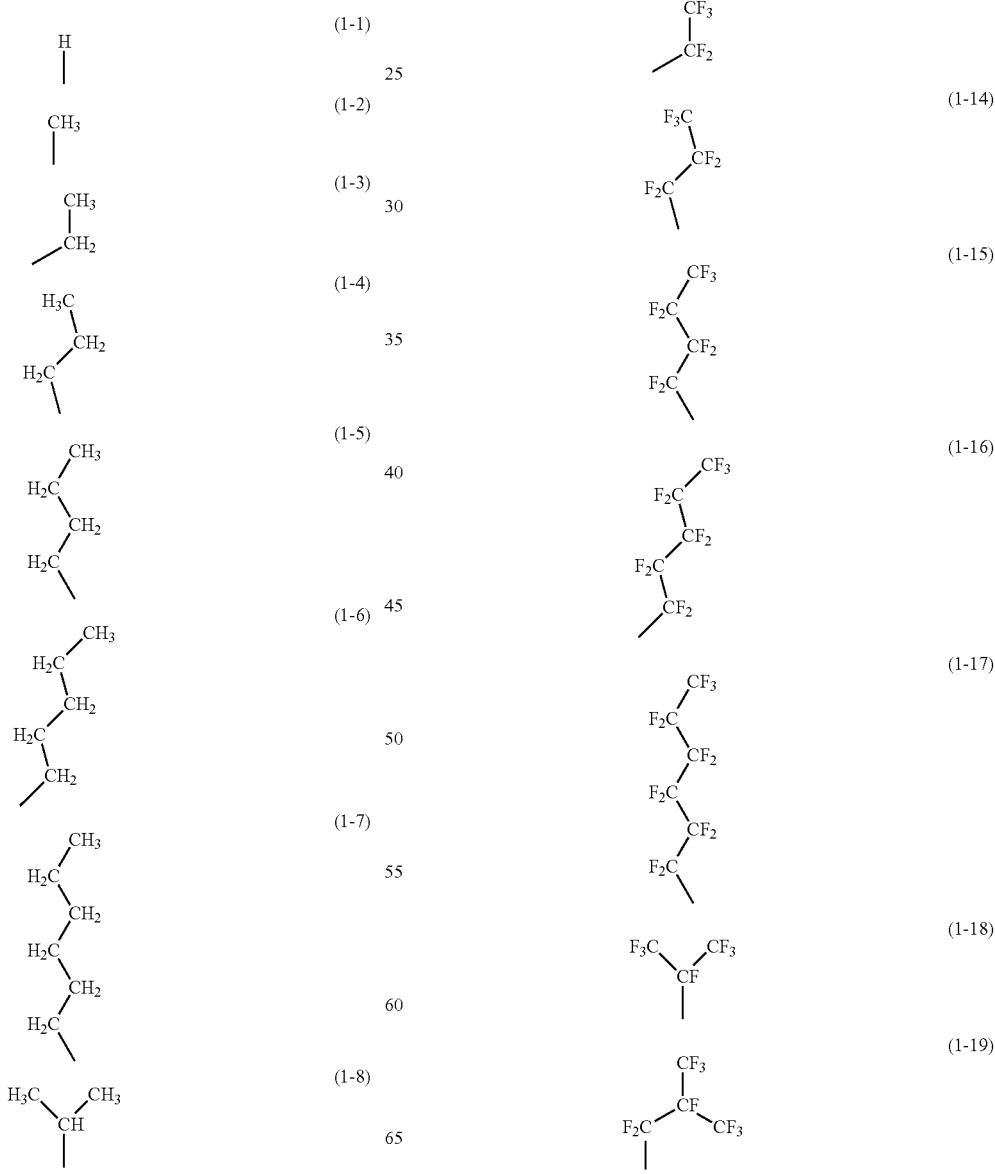

(1-20) 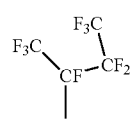
(1-21) 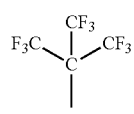
(1-22) 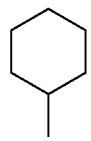
(1-23) 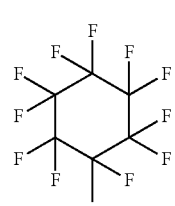
Specific examples of the organic compound having the above structure are shown below.
[Chemical Formulae 13]
(100) 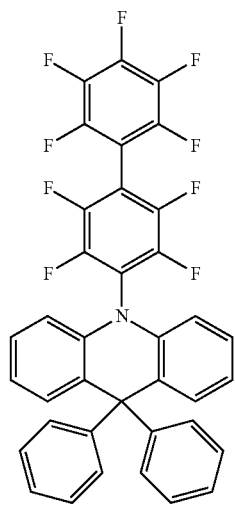
(101) 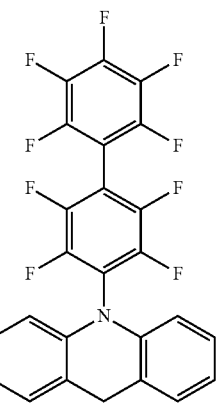
(102) 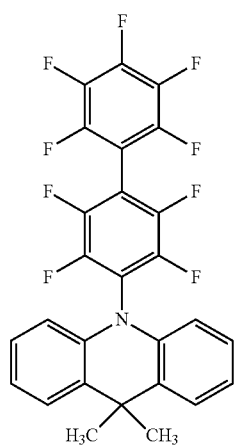
(103) 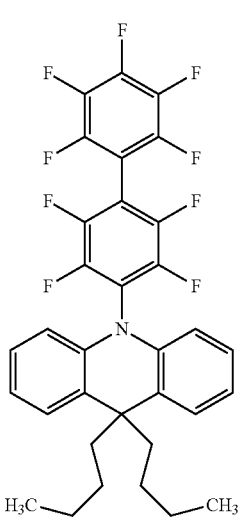

(104)
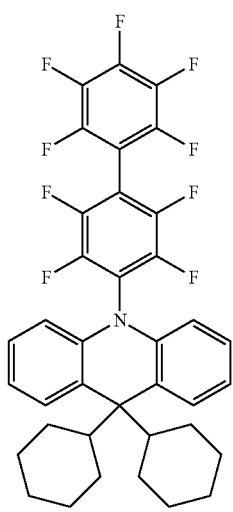
(105)
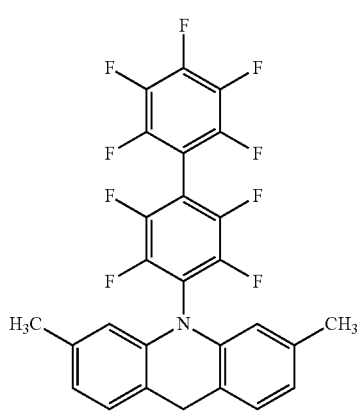
(107)
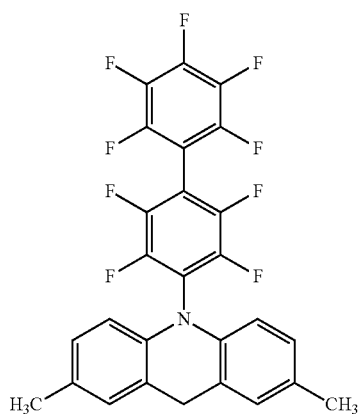
(108)
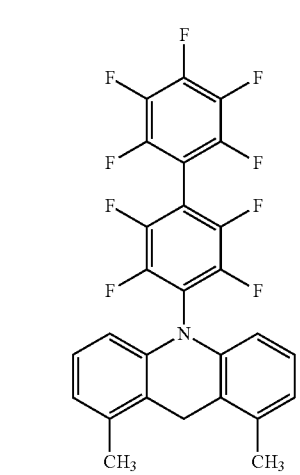
(109)
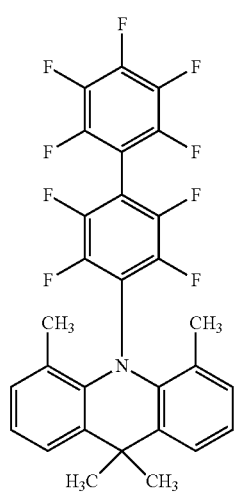

[Chemical Formulae 14]
(110)
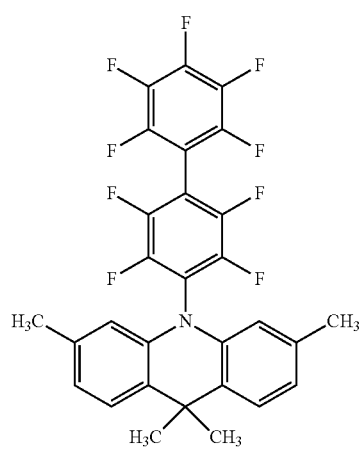
(111)
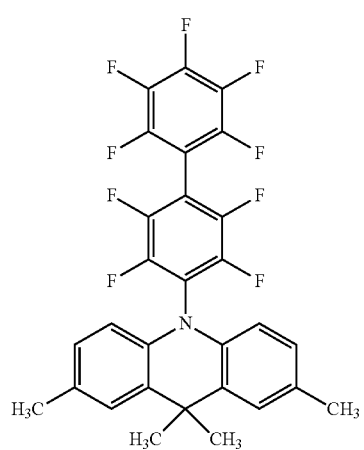
(112)
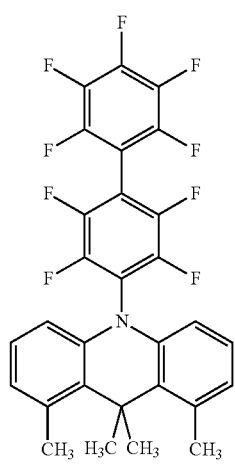
(113)
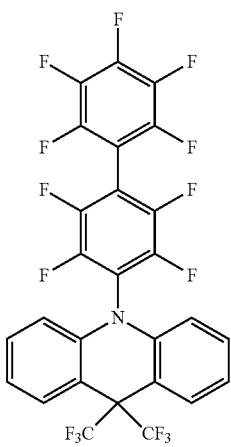
(114)
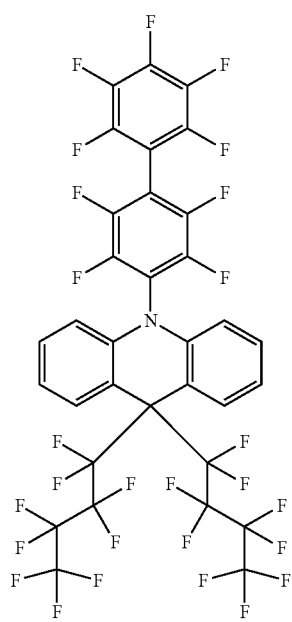
(115)
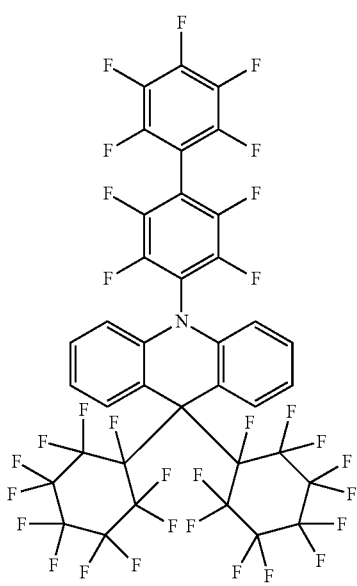

(116)
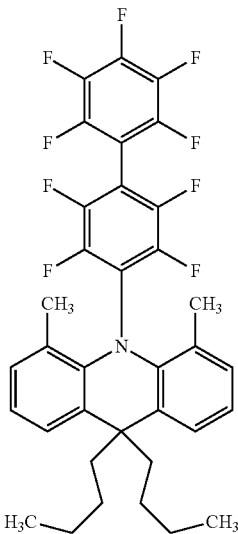
(117)
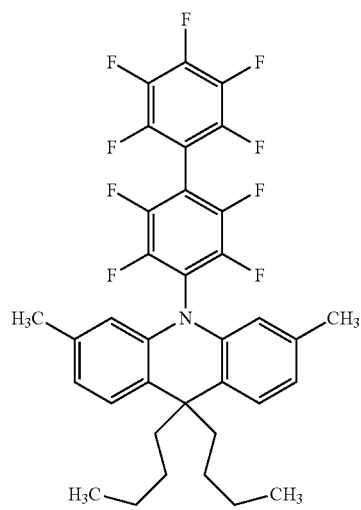
(118)
(119)
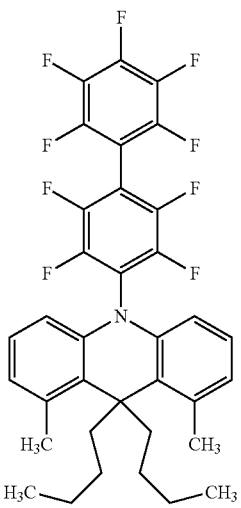
(120)
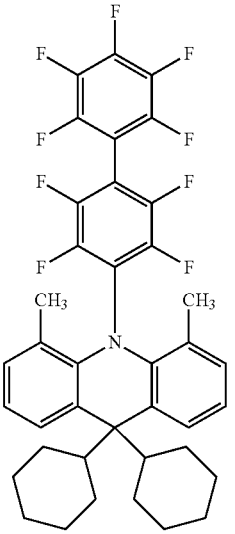
(121)
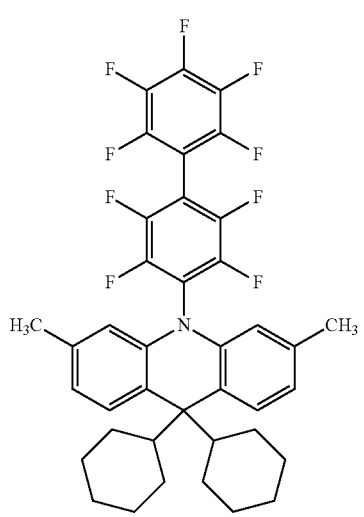

-continued
(122)
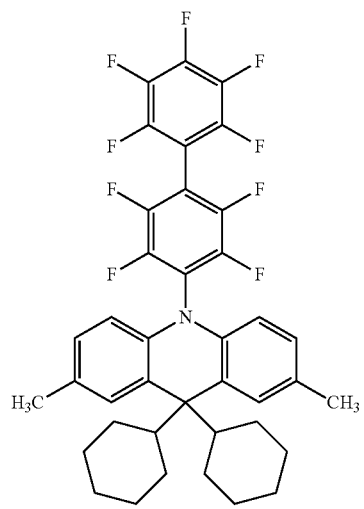
(123)
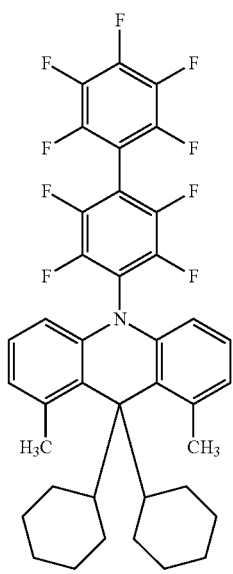
[Chemical Formulae 15]
(124)
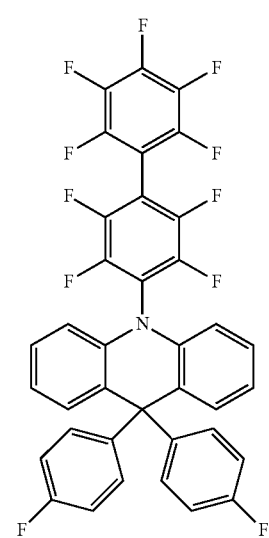
-continued
(125)
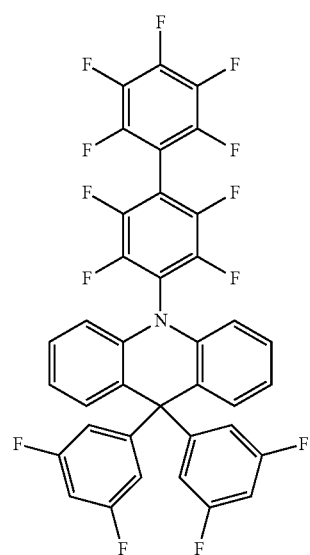
(126)
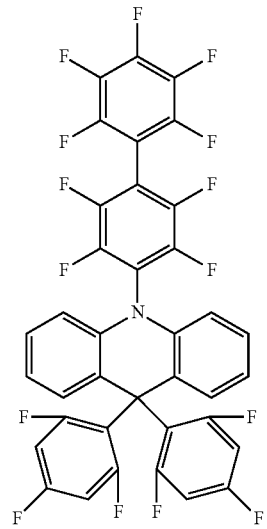
(127)
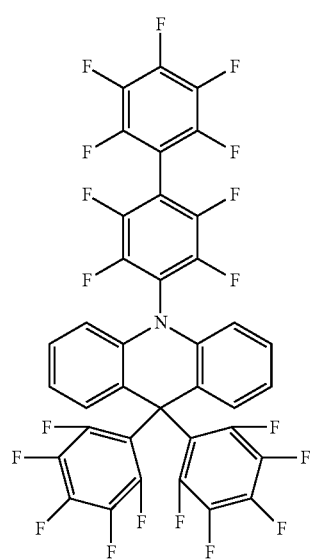

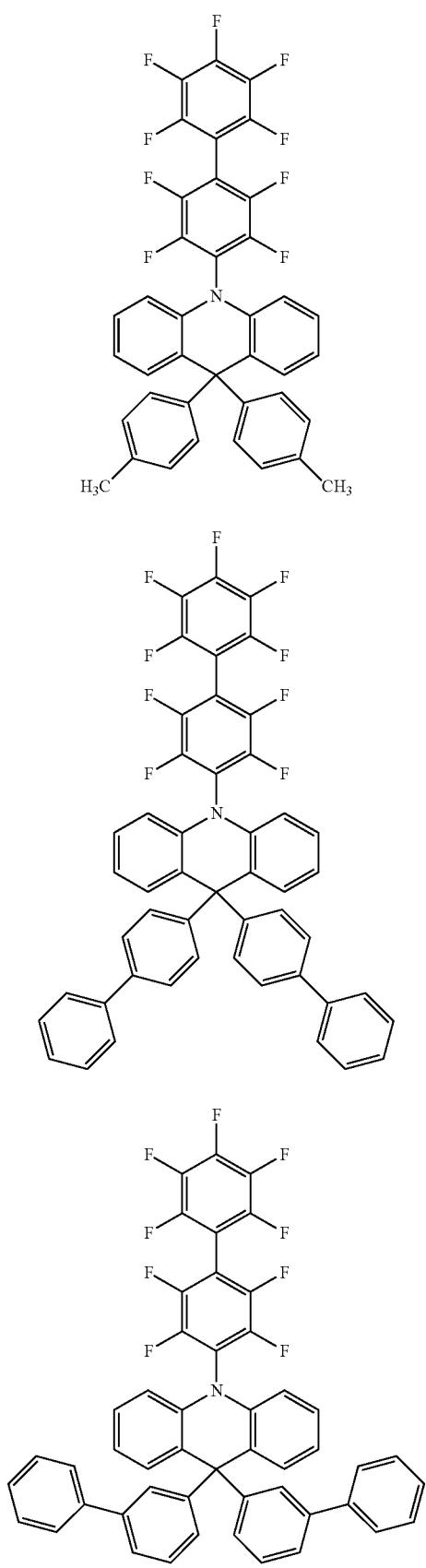
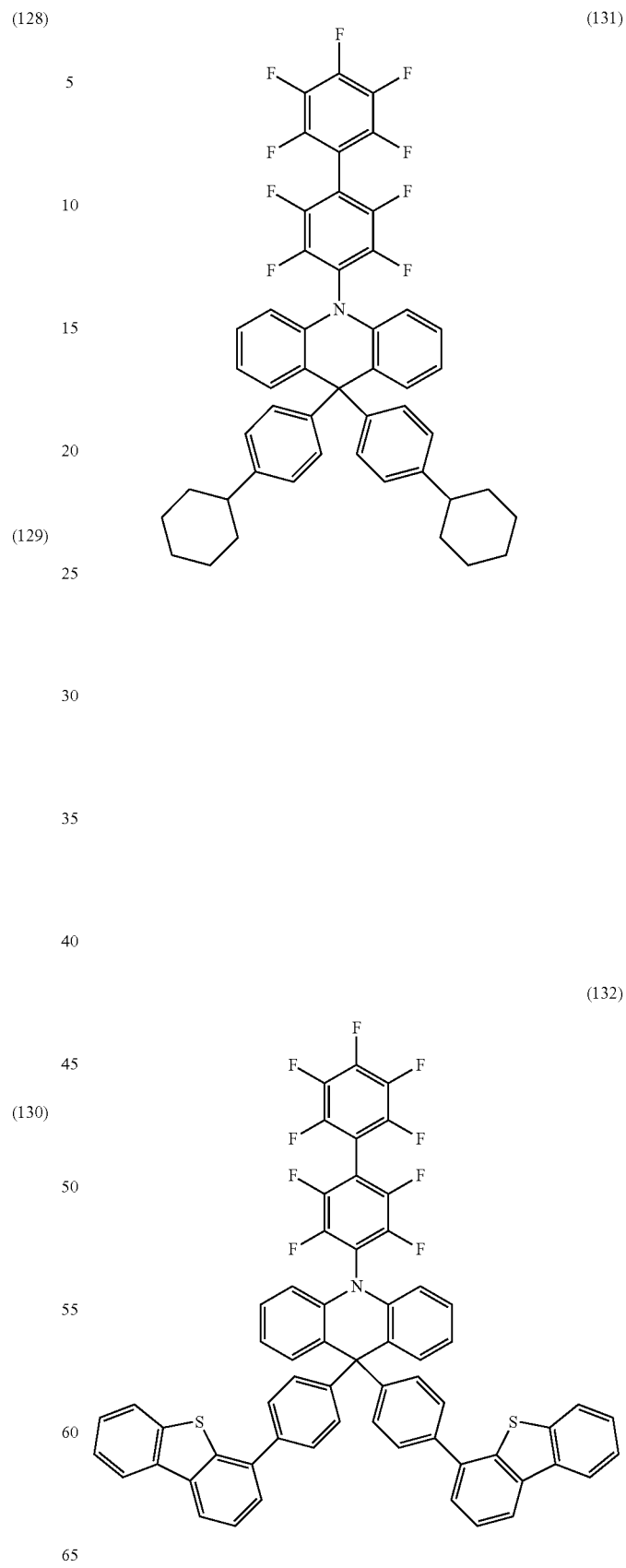

[Chemical Formulae 16]
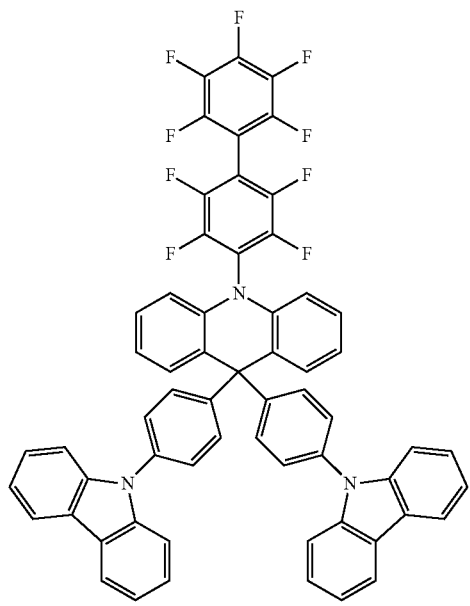
(133)
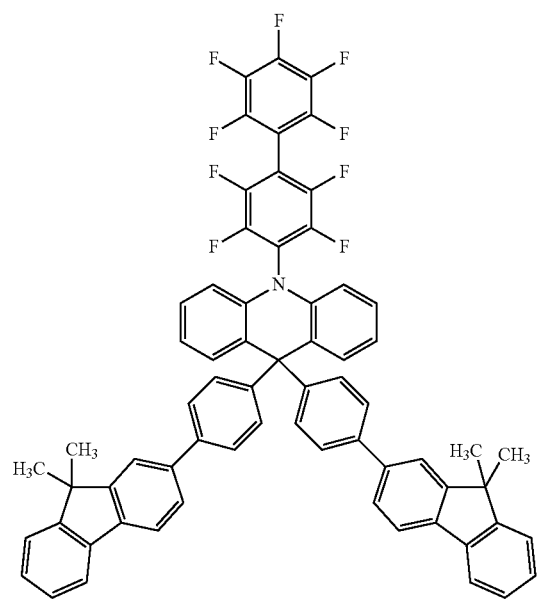
(134)
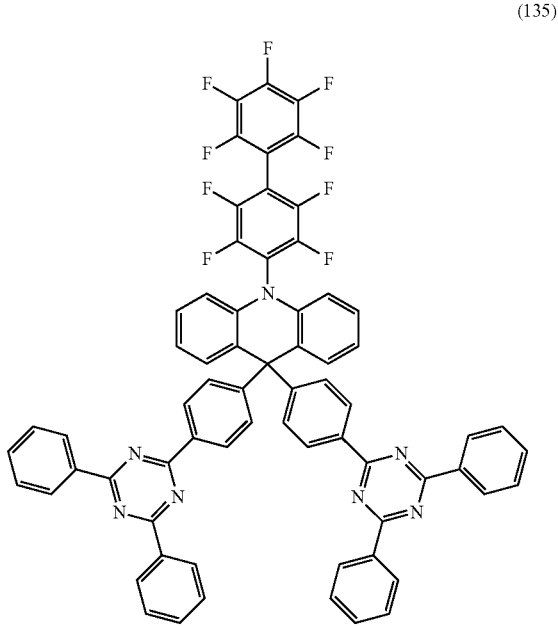
(135)
[Chemical Formulae 17]
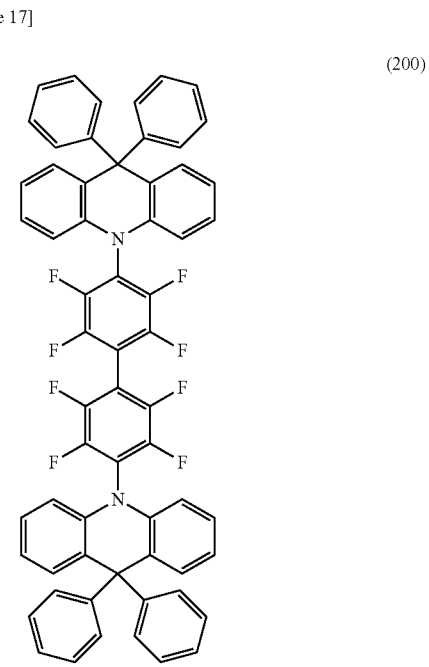
(200)

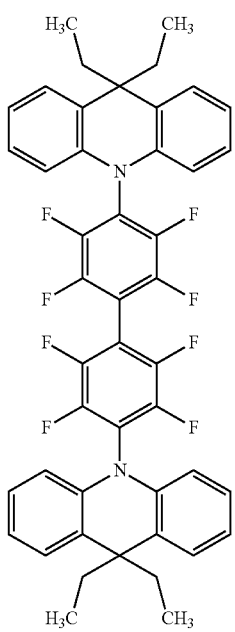
(201)
(202)
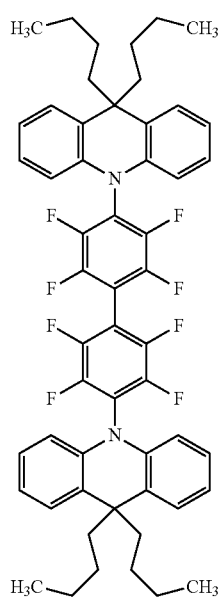
(203)
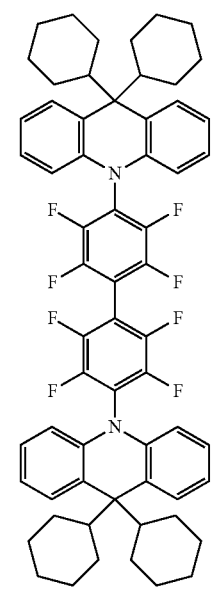
(204)

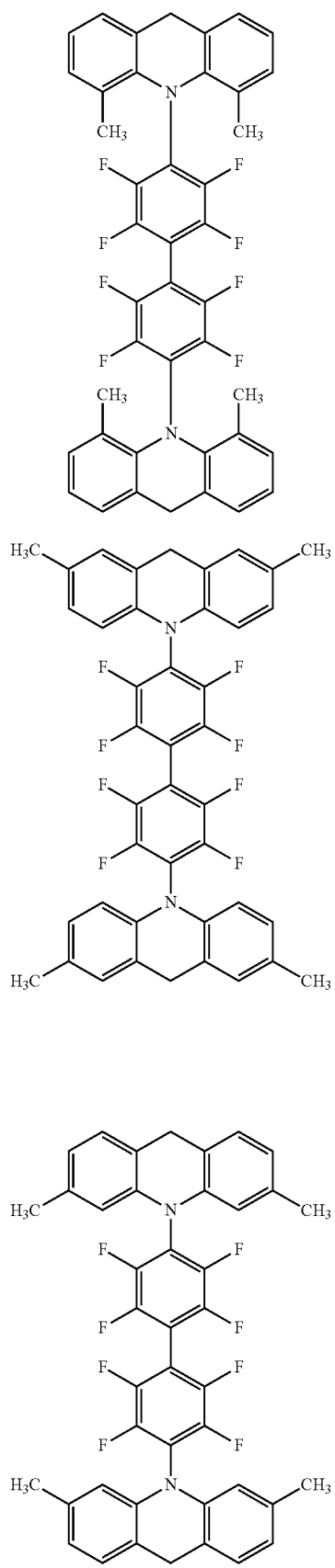
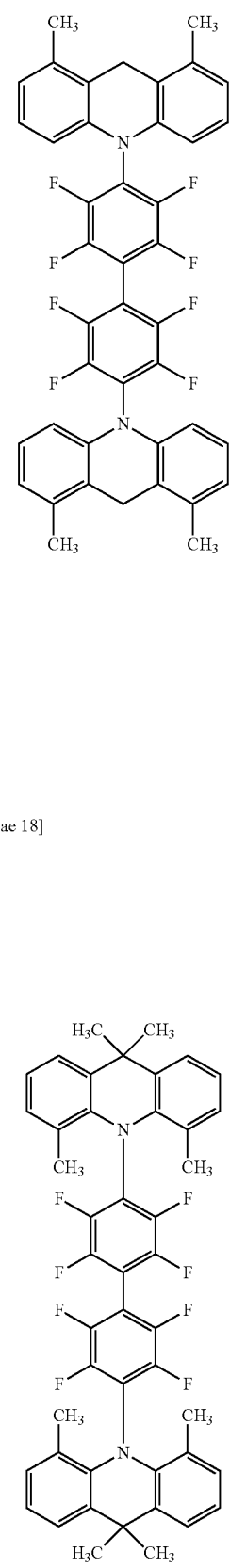
[Chemical Formulae 18]

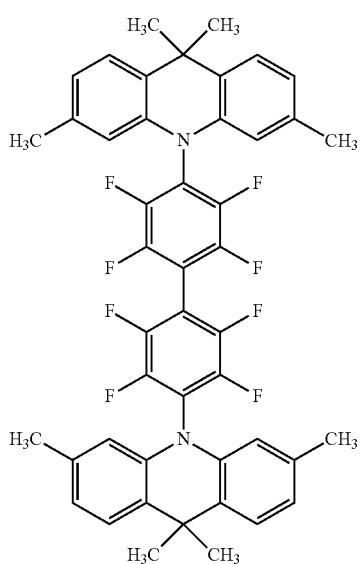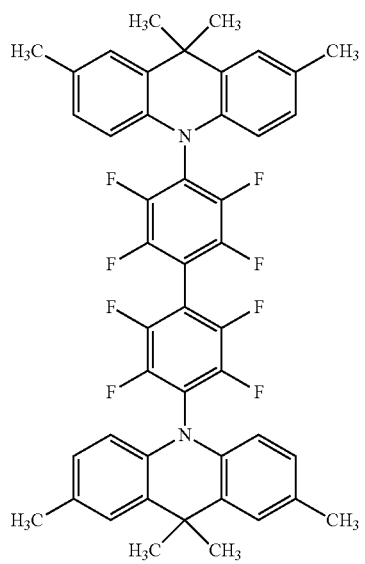

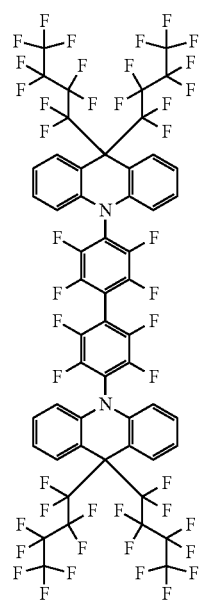
(215)
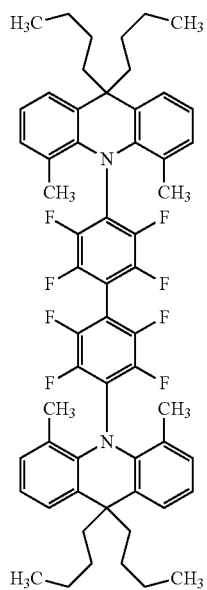
(217)
[Chemical Formulae 19]
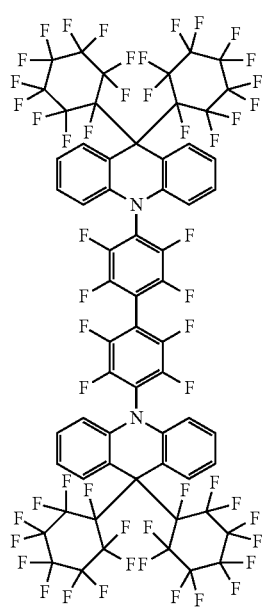
(216)
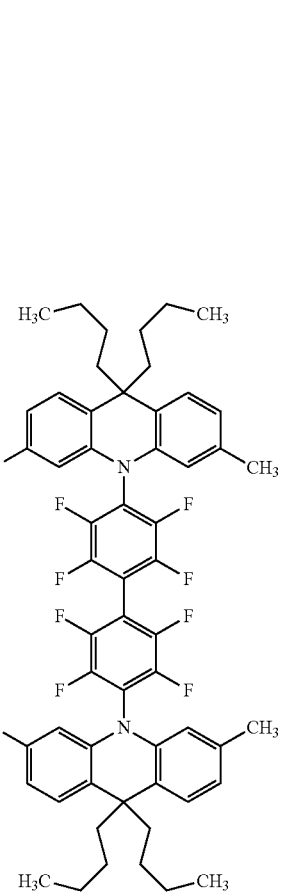
(218)

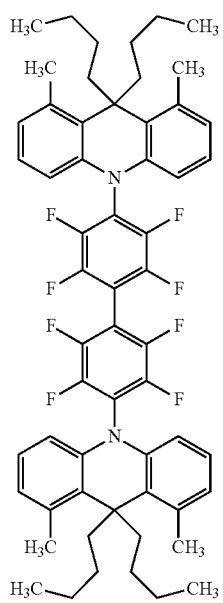
(219)
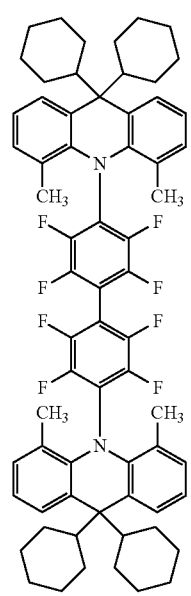
(221)
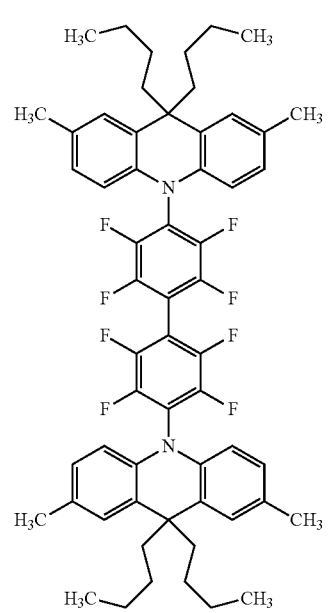
(220)
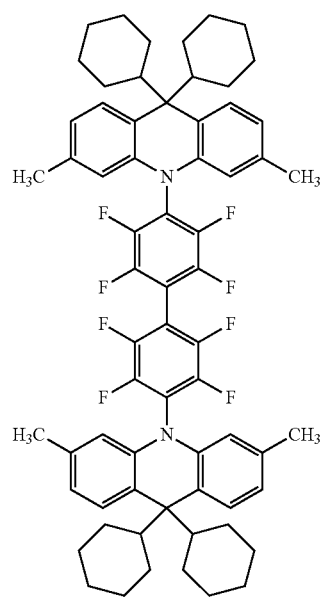
(222)

[Chemical Formulae 20]
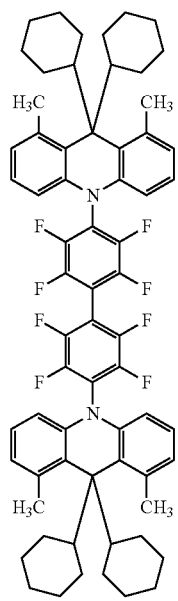
(223)
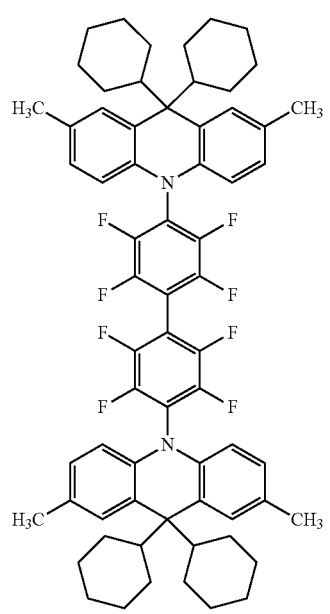
(224)
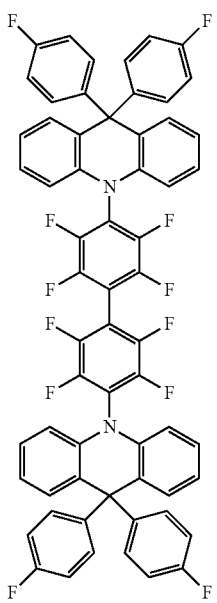
(225)
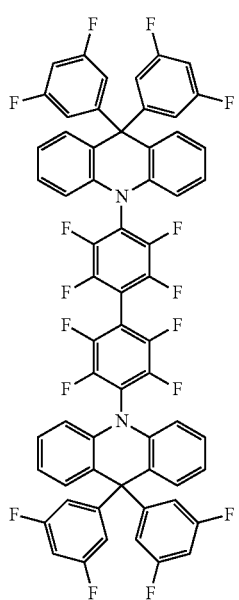
(226)

(227)
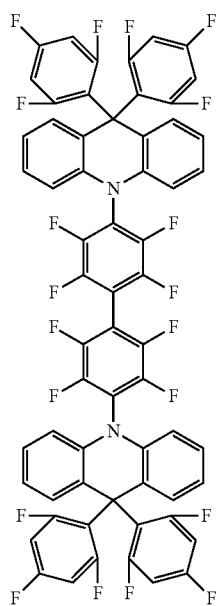
(228)
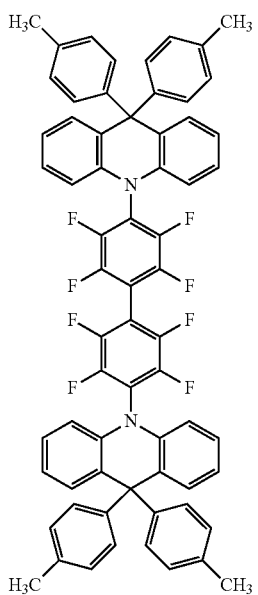
(229)
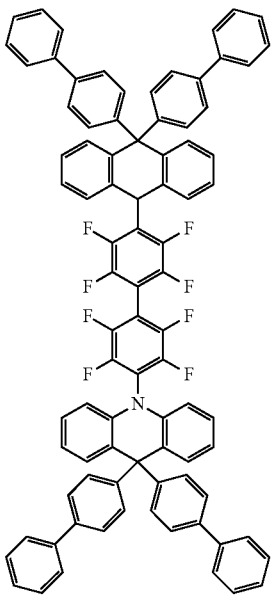
(230)

(231) 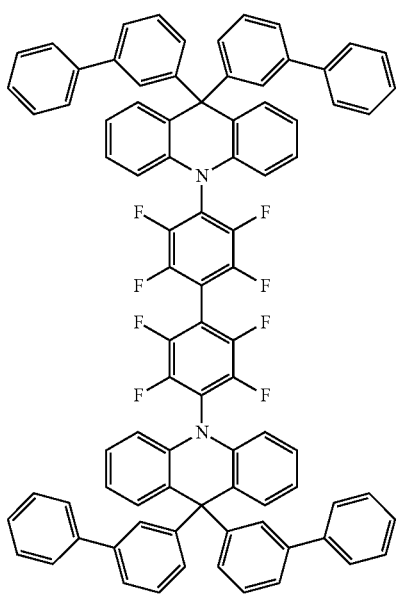
[Chemical Formulae 21]
(233) 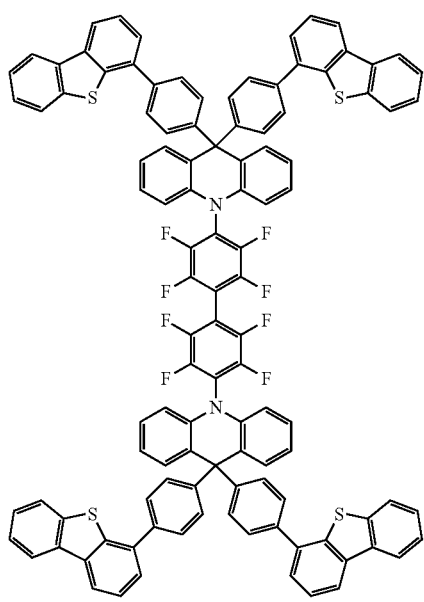
(232) 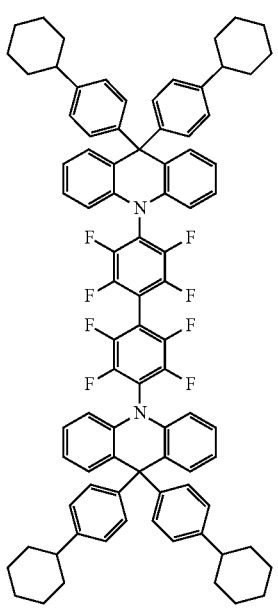
(234) 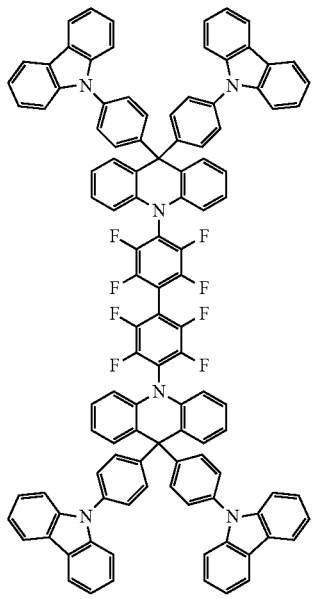

(235)

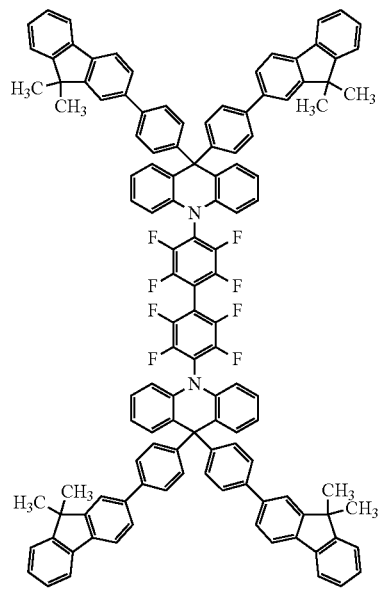

(236)

[Chemical Formula 22]

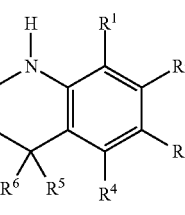

(g1-1)

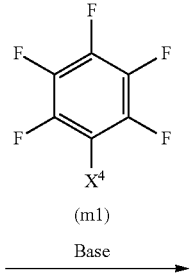

(m1)

Base →

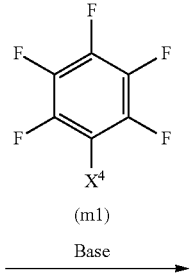

(G1)

[Chemical Formula 23]

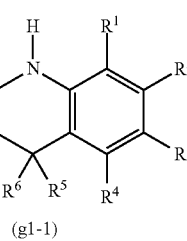

(g1-1)

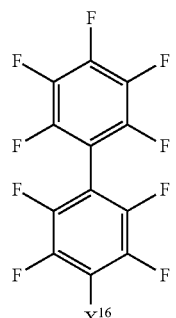

(m2)

Base →

Next, an example of a method for synthesizing the organic compound represented by General Formula (G1) or General Formula (G2) above is described.

The organic compound represented by General Formula (G1) or General Formula (G2) above can be synthesized by action between a derivative of 9,10-dihydroacridine (g1-1) and a fluorinated benzene derivative (m1) or a fluorinated biphenyl derivative (m2) in the presence of a strong base, as shown in the following synthesis schemes.

-continued

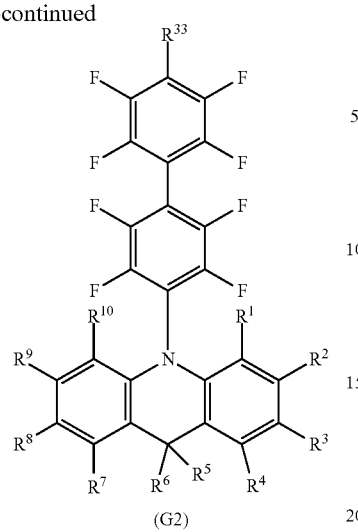

(G2)

[Chemical Formula 25]

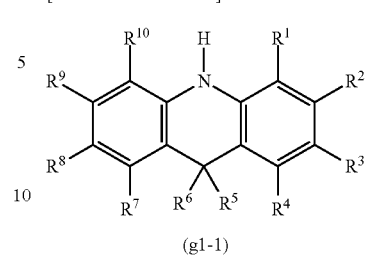

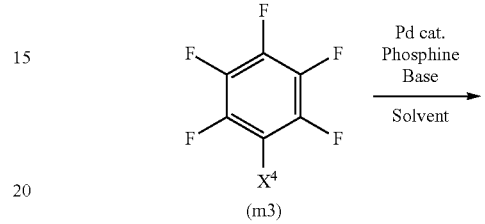

Note that in the above synthesis schemes, $R^1$ to $R^4$ and $R^7$ to $R^{10}$ each independently represent any one of hydrogen, an alkyl group having 1 to 6 carbon atoms, and an alkyl fluoride group having 1 to 6 carbon atoms, and $R^5$ and $R^6$ each independently represent any one of hydrogen, an alkyl group having 1 to 6 carbon atoms, an alkyl fluoride group having 1 to 6 carbon atoms, and a substituted or unsubstituted phenyl group. Moreover, $X^4$ or $X^{16}$ represents fluorine or chlorine and $R^{13}$ or $R^{33}$ represents fluorine or a group represented by General Formula (g1) below.

[Chemical Formula 24]

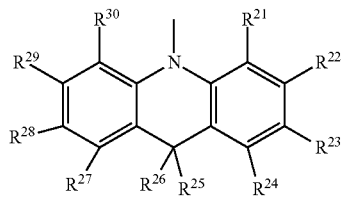

(g1)

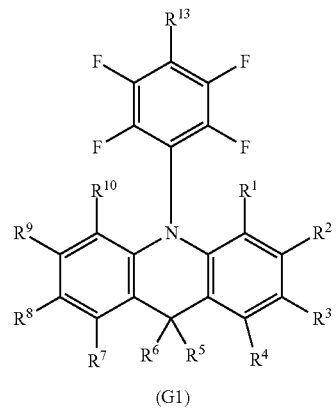

(G1)

[Chemical Formula 26]

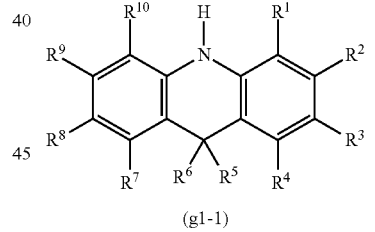

Note that in General Formula (g1) above, $R^{21}$ to $R^{24}$ and $R^{27}$ to $R^{30}$ each independently represent any one of hydrogen, an alkyl group having 1 to 6 carbon atoms, and an alkyl fluoride group having 1 to 6 carbon atoms, and $R^{25}$ and $R^{26}$ each independently represent any one of hydrogen, an alkyl group having 1 to 6 carbon atoms, an alkyl fluoride group having 1 to 6 carbon atoms, and a substituted or unsubstituted phenyl group.

In the case where the synthesis schemes are performed by an electrophilic aromatic substitution reaction, examples of the base include an inorganic base such as lithium amide, sodium amide, sodium hydroxide, or potassium hydroxide and an organic base such as sodium tert-butoxide. In the case where a solvent is used in the reaction, tetrahydrofuran, 1,4-dioxane, dimethoxyethane, formamide, dimethylformamide, dimethyl sulfoxide, or the like can be used.

The organic compound represented by General Formula (G1) or General Formula (G2) above can also be synthesized by action between a derivative of 9,10-dihydroacridine (g1-1) and a fluorinated benzene derivative (m3) or a fluorinated biphenyl derivative (m4) in the presence of a palladium catalyst and a base, as shown in the following synthesis schemes.

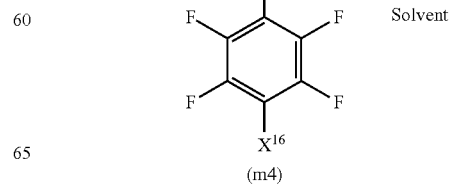

-continued

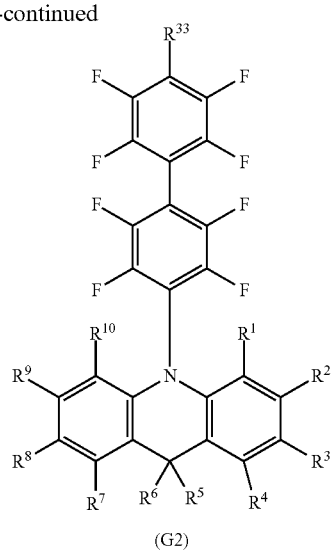

(G2)

Note that in the above synthesis schemes, $R^1$ to $R^4$ and $R^7$ to $R^{10}$ each independently represent any one of hydrogen, an alkyl group having 1 to 6 carbon atoms, and an alkyl fluoride group having 1 to 6 carbon atoms, and $R^5$ and $R^6$ each independently represent any one of hydrogen, an alkyl group having 1 to 6 carbon atoms, an alkyl fluoride group having 1 to 6 carbon atoms, and a substituted or unsubstituted phenyl group. Moreover, $X^4$ or $X^{16}$ represents a halogen or a triflate group. As the halogen, iodine, bromine, or chlorine is preferable. Furthermore, $R^{13}$ or $R^{33}$ represents fluorine or a group represented by General Formula (g1) below.

[Chemical Formula 27]

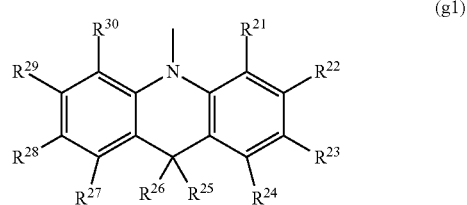

(g1)

Note that in General Formula (g1) above, $R^{21}$ to $R^{24}$ and $R^{27}$ to $R^{30}$ each independently represent any one of hydrogen, an alkyl group having 1 to 6 carbon atoms, and an alkyl fluoride group having 1 to 6 carbon atoms, and $R^{25}$ and $R^{26}$ each independently represent any one of hydrogen, an alkyl group having 1 to 6 carbon atoms, an alkyl fluoride group having 1 to 6 carbon atoms, and a substituted or unsubstituted phenyl group.

Note that in the above synthesis schemes, $X^4$ or $X^{16}$ represents a halogen or a triflate group. As the halogen, iodine, bromine, or chlorine is preferable.

The above synthesis schemes are each preferably performed as a Buchwald-Hartwig reaction. In this reaction, a palladium catalyst including a palladium complex or a palladium compound such as bis(dibenzylideneacetone)palladium(0) or allylpalladium(II) chloride dimer and a ligand that coordinates to the palladium complex or the palladium compound, such as tri(tert-butyl)phosphine, di-tert-butyl(1-methyl-2,2-diphenylcyclopropyl)phosphine, or tricyclohexylphosphine, is used. Examples of the base include an organic base such as sodium tert-butoxide and an inorganic base such as potassium carbonate. In the case where a solvent is used in the reaction, toluene, xylene, 1,3,5-trimethylbenzenebenzene, or the like can be used.

In the above manner, the organic compound represented by General Formula (G1) or General Formula (G2) can be synthesized.

Here, as described above, the organic compound (the first substance) typically represented by General Formula (G1) or General Formula (G2), which has an arylamine skeleton or an acridine skeleton and contains fluorine, can be favorably used for a hole-injection layer or an intermediate layer of an EL device when used with the second substance with respect to which the organic compound can show an electron-donating property. The first substance and the second substance may be mixed to be used or thin films thereof may be stacked; however, it is preferable to use a composite material in which the first substance and the second substance are mixed by co-evaporation.

When one of a pair of substances shows an electron-donating property with respect to the other substance, it can be said that the other substance shows an electron-accepting property with respect to the one substance. Therefore, the second substance can be referred to as a substance having an electron-accepting property with respect to the first substance. As a substance having an electron-accepting property that can be used as the second substance, molybdenum oxide, vanadium oxide, ruthenium oxide, tungsten oxide, manganese oxide, or the like can be given. In particular, molybdenum oxide is a preferred substance among them because it is stable in the air, has a low hygroscopic property, and is easy to handle.

As a substance having an electron-accepting property, an organic compound having an electron-withdrawing group (a halogen group or a cyano group) other than the above-described substances can be given. A [3]radialene derivative including an electron-withdrawing group (in particular, a cyano group or a halogen group such as a fluoro group) is favorably used as an organic compound having an electron-accepting property because it has a very high electron-accepting property. As such an organic compound, for example, 7,7,8,8-tetracyano-2,3,5,6-tetrafluoroquinodimethane (abbreviation: F4-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), or the like, α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], or α,α',α''-1,2,3-cyclopropanetriylidenetris[2,3,4,5,6-pentafluorobenzeneacetonitrile] can be used. As an organic compound having an electron-accepting property, a compound in which electron-withdrawing groups are bonded to a fused aromatic ring having a plurality of heteroatoms, such as HAT-CN, is preferable because it is thermally stable.

Alternatively, it is also possible to use a phthalocyanine-based complex compound such as phthalocyanine (abbreviation: $H_2Pc$) and copper(II) phthalocyanine (CuPC), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or the like.

Note that when a composite material in which an electron-donating material and an electron-accepting material are mixed by co-evaporation is used for a hole-injection layer in contact with an anode, a material used to form an electrode can be selected regardless of its work function. In other words, besides a material having a high work function, a material having a low work function can also be used for the anode.

Embodiment 2

In this embodiment, a detailed embodiment of the EL device described in Embodiment 1 is described. FIG. 1 shows diagrams illustrating EL devices of embodiments of the present invention. The EL device illustrated in FIG. TA includes an anode 101, a cathode 102, and an EL layer 103. The EL device of one embodiment of the present invention includes, in the EL layer 103, the organic compound (the first substance) described in Embodiment 1, which has an arylamine skeleton or an acridine skeleton and contains fluorine. In the EL layer 103, the first substance preferably forms a first layer together with the second substance. Note that the first substance shows an electron-donating property with respect to the second substance.

In FIG. 1, the first layer is preferably used as a hole-injection layer 111. The EL layer 103 includes functional layers typified by a light-emitting layer 113 in addition to the first layer, and may include a hole-transport layer 112, an electron-transport layer 114, an electron-injection layer 115, and the like in addition to the light-emitting layer 113 and the hole-injection layer 111. The light-emitting layer 113 contains a light-emitting material, and light is obtained from the light-emitting material in the EL device of one embodiment of the present invention. The light-emitting layer 113 may contain a host material and another material. The first substance may be contained in any of the light-emitting layer 113, the hole-transport layer 112, and the hole-injection layer; alternatively, the first substance may be contained in all of these layers. Note that the structure of the EL device is not limited to those.

Since the first substance is an organic compound with a low refractive index, the EL device using the first substance in its EL layer can have high external quantum efficiency. In addition, the first layer containing the first substance and the second substance can also be a layer with a low refractive index; similarly, an EL device including the first layer can be an EL device having high external quantum efficiency. Moreover, the first layer favorably functions as a hole-injection layer, and an EL device including the first layer as a hole-injection layer can be an EL device in which emission efficiency such as external quantum efficiency is high and main performance other than the emission efficiency (e.g., a driving voltage and a lifetime) are also favorable.

Next, examples of specific structures and materials of the aforementioned EL device will be described.

The anode 101 is preferably formed using any of metals, alloys, and conductive compounds with a high work function (specifically, higher than or equal to 4.0 eV), mixtures thereof, and the like. Specific examples include indium oxide-tin oxide (ITO: Indium Tin Oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 to 20 wt % of zinc oxide to indium oxide. Furthermore, indium oxide containing tungsten oxide and zinc oxide (IWZO) can be deposited by a sputtering method using a target in which tungsten oxide and zinc oxide are added to indium oxide at 0.5 to 5 wt % and 0.1 to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer that is in contact with the anode 101 in the EL layer 103, an electrode material can be selected regardless of its work function.

Although the EL layer 103 preferably has a stacked structure, there is no particular limitation on the stacked structure, and various layer structures such as a hole-injection layer, a hole-transport layer, an electron-transport layer, an electron-injection layer, a carrier-blocking layer, an exciton-blocking layer, and a charge-generation layer can be employed. Two types of structure are described in this embodiment: the structure shown in FIG. TA, which includes the electron-transport layer 114 and the electron-injection layer 115 in addition to the hole-injection layer 111, the hole-transport layer 112, and the light-emitting layer 113; and the structure shown in FIG. 1B, which includes the electron-transport layer 114, the electron-injection layer 115, and a charge-generation layer 116 in addition to the hole-injection layer 111, the hole-transport layer 112, and the light-emitting layer 113. Materials for forming each layer will be specifically described below.

The EL device of one embodiment of the present invention includes the first layer with a low refractive index, which is described in Embodiment 1, and the first layer is preferably the hole-injection layer 111.

In the case where the hole-injection layer 111 is not the first layer, the first layer can be formed using a substance having an electron-accepting property. As a substance having an electron-accepting property, a high molecule such as poly(3,4-ethylenedioxythiophene)/poly(styrenesulfonic acid) (PEDOT/PSS) as well as the substances given in Embodiment 1 as substances that can be used as the second substance can be used. A substance having an electron-accepting property can extract electrons from an adjacent hole-transport layer (or hole-transport material) when an electric field is applied, and can inject (generate) holes to the adjacent hole-transport layer (or hole-transport material) after the extraction of electrons.

Alternatively, a composite material in which a substance having a hole-transport property contains an electron-accepting substance can be used for the hole-injection layer 111. By using a composite material in which a substance having a hole-transport property contains an electron-accepting substance, a material used to form an electrode can be selected regardless of its work function. In other words, besides a material having a high work function, a material having a low work function can also be used for the anode 101. As the electron-accepting substance, it is possible to use any of the substances given as substances that can be used as the second substance in Embodiment 1.

As the substance having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance having a hole-transport property used for the composite material preferably has a hole mobility of $10^{-6}$ cm$^2$Vs or higher. Organic compounds which can be used as the substance having a hole-transport property in the composite material are specifically given below.

Examples of the aromatic amine compounds that can be used for the composite material include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and 1,1-bis-(4-bis(4-methyl-phenyl)-amino-phenyl)-cyclohexane (abbreviation: TAPC). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD).

The hole-transport layer 112 contains a material having a hole-transport property. The material having a hole-transport property preferably has a hole mobility of $1 \times 10^{-6}$ cm$^2$/Vs or higher.

Examples of the material having a hole-transport property include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. Note that any of the substances given as examples of the material having a hole-transport property that is used in the composite material for the hole-injection layer 111 can also be suitably used as the material included in the hole-transport layer 112.

The light-emitting layer 113 is a layer containing a host material and a light-emitting material. The light-emitting material may be fluorescent substances, phosphorescent substances, substances exhibiting thermally activated delayed fluorescence (TADF), or other light-emitting materials. Furthermore, it may be a single layer or be formed of a plurality of layers including different light-emitting materials.

Examples of a material that can be used as a fluorescent substance in the light-emitting layer 113 are as follows. Fluorescent substances other than those given below can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPm), N,N-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N', N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and N,N'-(pyrene-1,6-diyl)bis[(6,N-diphenylbenzo[b]naphtho[1,2-d]furan)-8-amine](abbreviation: 1,6BnfAPrn-03). Fused aromatic diamine compounds typified by pyrenediamine compounds such as 1,6FLPAPrn, 1,6mMemFLPA-Prn, and 1,6BnfAPrn-03 are particularly preferable because of their high hole-trapping properties, high emission efficiency, and high reliability.

Examples of a material that can be used as a phosphorescent substance in the light-emitting layer 113 include the following materials.

The examples include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIracac). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^2$)iridium(III) acetylacetonate (abbreviation: [Ir(pq)$_2$(acac)]); and a rare earth metal complex such as tris(acetylacetonato) (monophenanthroline)terbium(III) (abbreviation: [Tb(acac)$_3$(Phen)]). These are mainly compounds that emit green phosphorescence and have an emission peak at 500 nm to 600 nm. Note that organometallic iridium complexes having a pyrimidine skeleton have distinctively high reliability and emission efficiency and thus are particularly preferable.

Other examples include organometallic iridium complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: PtOEP); and rare earth metal complexes such as tris(1,3-diphenyl-1,3-propanedionato) (monophenanthroline)europium(III) (abbreviation: [Eu(DBM)$_3$ (Phen)]) and tris[1-(2-thenoyl)-3,3,3-trifluoroacetonato](monophenanthroline)europium(III) (abbreviation: [Eu(TTA)$_3$(Phen)]). These compounds emit red phosphorescence and have an emission peak at 600 nm to 700 nm. Furthermore, the organometallic iridium complexes having a pyrazine skeleton can provide red light emission with favorable chromaticity.

Besides the above-described phosphorescent compounds, other known phosphorescent materials may be selected and used.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octa-ethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP), which are represented by the following structural formulae.

[Chemical Formulae 28]

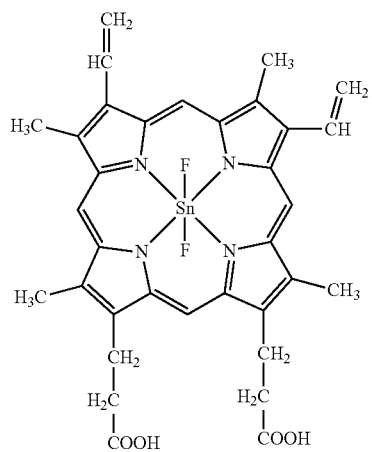

SnF$_2$(Proto IX)

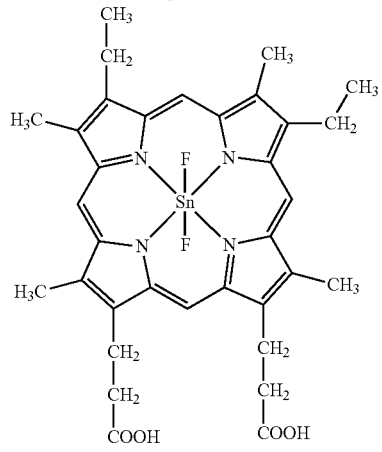

SnF$_2$(Meso IX)

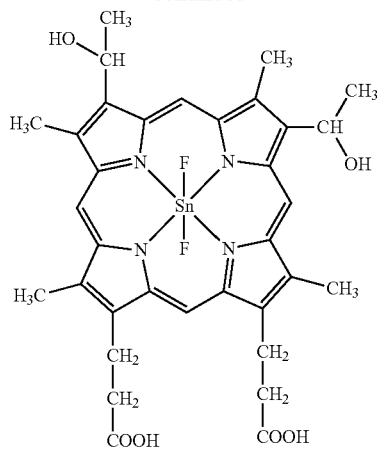

SnF$_2$(Hemato IX)

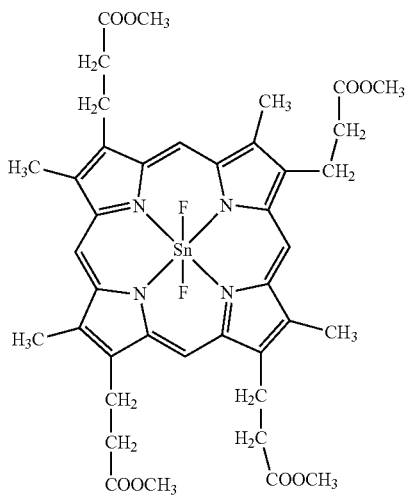

SnF$_2$(Copro III-4Me)

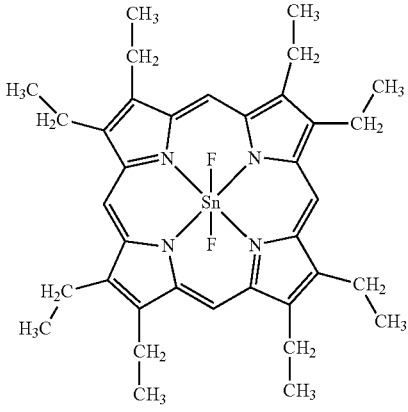

SnF$_2$(OEP)

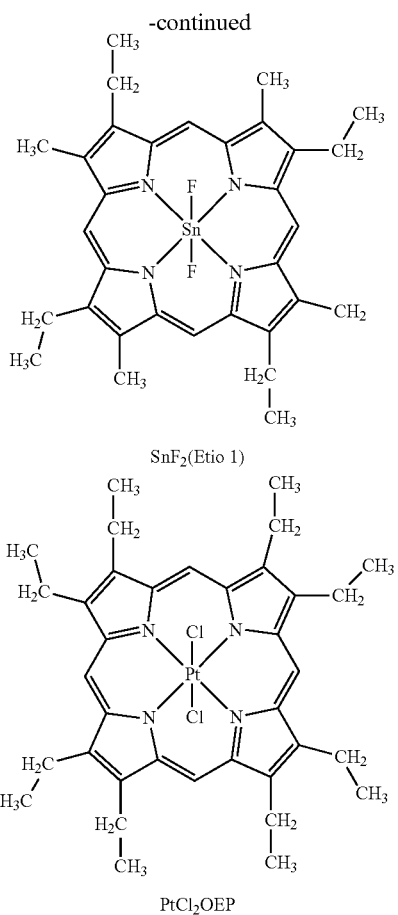

SnF₂(Etio 1)

PtCl₂OEP

Alternatively, a heterocyclic compound having one of both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. The heterocyclic compound is preferable because of having both a high electron-transport property and a high hole-transport property owing to a π-electron rich heteroaromatic ring and a π-electron deficient heteroaromatic ring. Among skeletons having a π-electron deficient heteroaromatic ring, a pyridine skeleton, a diazine skeleton (a pyrimidine skeleton, a pyrazine skeleton, or a pyridazine skeleton) and a triazine skeleton are particularly preferable because of their high stability and reliability. In particular, a benzofuropyrimidine skeleton, a benzothienopyrimidine skeleton, a benzofuropyrazine skeleton, and a benzothienopyrazine skeleton are preferable because of their high acceptor property and reliability. Among skeletons having a π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. Note that a dibenzofuran skeleton and a dibenzothiophene skeleton are preferable as the furan skeleton and the thiophene skeleton, respectively. As the pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which a π-electron rich heteroaromatic ring and a π-electron deficient heteroaromatic ring are directly bonded to each other is particularly preferable because the electron-donating property of the π-electron rich heteroaromatic ring and the electron-accepting property of the π-electron deficient heteroaromatic ring are both increased and the energy difference between the $S_1$ level and the $T_1$ level becomes small, so that thermally activated delayed fluorescence can be obtained efficiently. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a boron-containing skeleton such as phenylborane or boranthrene, an aromatic ring or a heteroaromatic ring having a nitrile group or a cyano group, such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formulae 29]

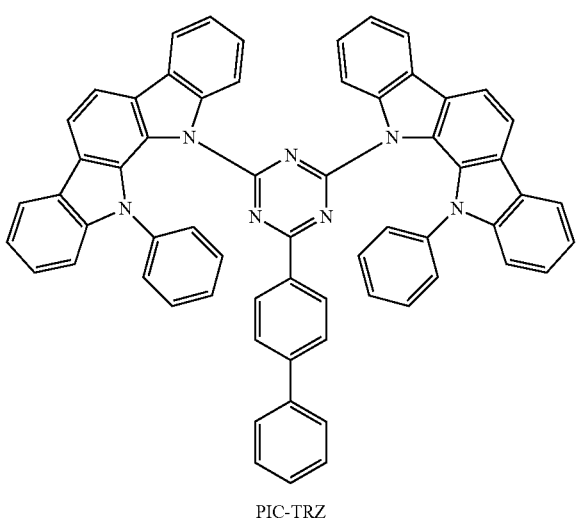

PIC-TRZ

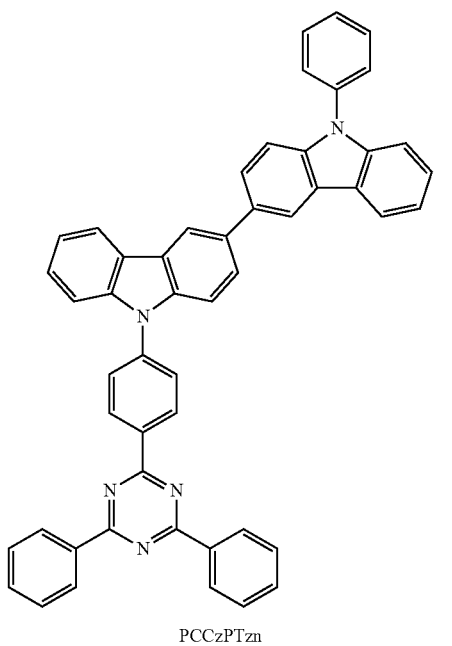

PCCzPTzn

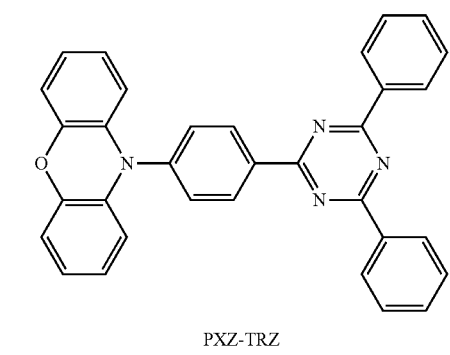

PCCzTzn

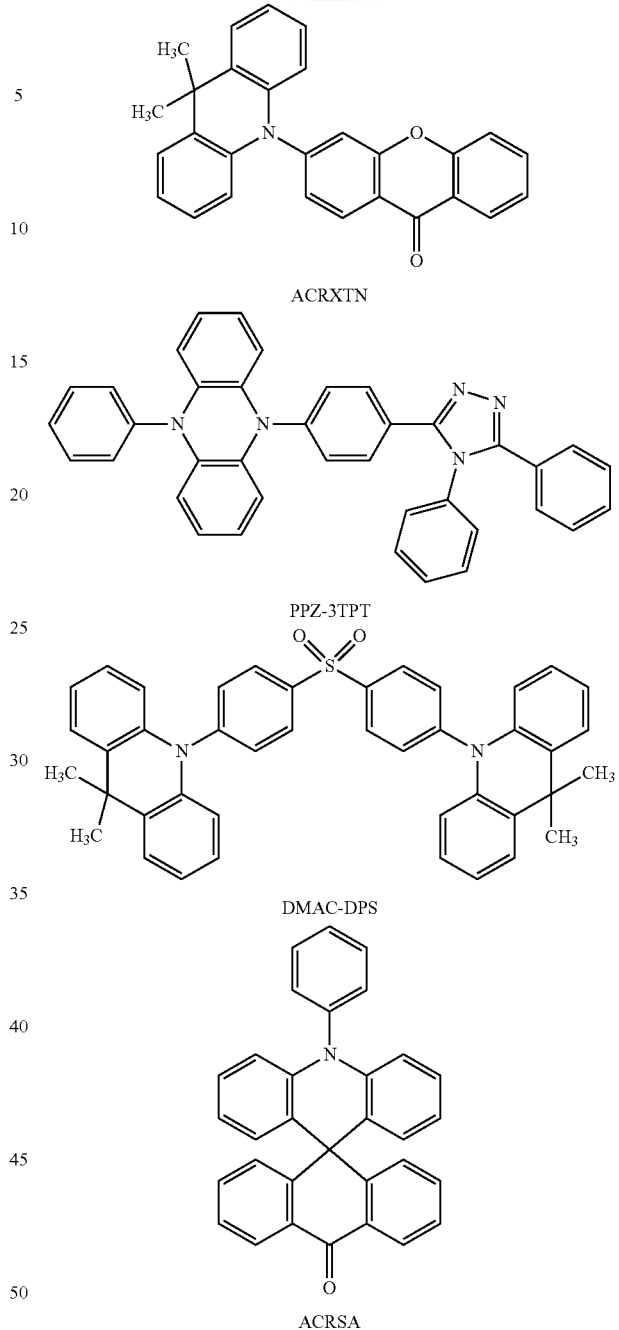

ACRXTN

PPZ-3TPT

DMAC-DPS

ACRSA

PXZ-TRZ

Note that the TADF material is a material that has a small difference between the S1 level and the T1 level and has a function of converting triplet excitation energy into singlet excitation energy by reverse intersystem crossing. Thus, it is possible to upconvert triplet excitation energy into singlet excitation energy (reverse intersystem crossing) using a little thermal energy and to efficiently generate a singlet excited state. In addition, the triplet excitation energy can be converted into luminescence.

An exciplex whose excited state is formed by two kinds of substances has an extremely small difference between the S1 level and the T1 level and functions as a TADF material that can convert triplet excitation energy into singlet excitation energy.

Note that a phosphorescent spectrum observed at low temperatures (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between S1 and T1 of the TADF material is preferably smaller than or equal to 0.3 eV, further preferably smaller than or equal to 0.2 eV.

When the TADF material is used as an emission center material, the S1 level of the host material is preferably higher than the S1 level of the TADF material. In addition, the T1 level of the host material is preferably higher than the T1 level of the TADF material.

As the host material in the light-emitting layer, various carrier-transport materials such as materials having an electron-transport property, materials having a hole-transport property, and the above-described TADF material can be used.

As the material having a hole-transport property, the substance given as the material having a hole-transport property which is contained in the hole-transport layer 112 can be favorably used.

Examples of the material having an electron-transport property include a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ), a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBT-BIm-II), a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II), and a heterocyclic compound having a pyridine skeleton, such as 3,5-bis[3-(9H-carbazol-9-yl)phenyl]pyridine (abbreviation: 35DCzPPy) or 1,3,5-tri[3-(3-pyridyl)-phenyl]benzene (abbreviation: TmPyPB). Among the above, the heterocyclic compound having a diazine skeleton and the heterocyclic compound having a pyridine skeleton are preferable because of having high reliability. In particular, the heterocyclic compound having a diazine (pyrimidine or pyrazine) skeleton has a high electron-transport property and contributes to a reduction in driving voltage.

In the case where a fluorescent substance is used as the light-emitting material, a material having an anthracene skeleton is favorably used as the host material. The use of a substance having an anthracene skeleton as the host material for the fluorescent substance makes it possible to obtain a light-emitting layer with high emission efficiency and high durability. Most of materials having an anthracene skeleton have a deep HOMO level; therefore, one embodiment of the present invention can be suitably used. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further fused to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole skeleton or a dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(N-carbazolyl)]phenyl-10-phenylanthracene (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). In particular, CzPA, cgDBCzPA, 2mBnfPPA, and PCzPA are preferably selected because they exhibit excellent characteristics.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

An exciplex may be formed of these mixed materials. These mixed materials are preferably selected so as to form an exciplex that exhibits light emission whose wavelength overlaps with the wavelength on a lowest-energy-side absorption band of the light-emitting material, in which case energy can be transferred smoothly and light emission can be obtained efficiently. The use of such a structure is preferable because the driving voltage can also be reduced.

The electron-transport layer 114 contains a substance having an electron-transport property. As the substance having an electron-transport property, it is possible to use any of the above-listed substances having electron-transport properties that can be used as the host material.

A layer containing an alkali metal, an alkaline earth metal, or a compound thereof such as lithium fluoride (LiF), cesium fluoride (CsF), or calcium fluoride (CaF$_2$) may be provided as the electron-injection layer 115 between the electron-transport layer 114 and the cathode 102. An electride or a layer that is formed using a substance having an electron-transport property and that includes an alkali metal, an alkaline earth metal, or a compound thereof can be used as the electron-injection layer 115. Examples of the electride include a substance in which electrons are added at high concentration to calcium oxide-aluminum oxide.

Note that as the electron-injection layer 115, it is possible to use a layer that contains a substance having an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, an EL device including the layer can have high external quantum efficiency.

Figure 1B:
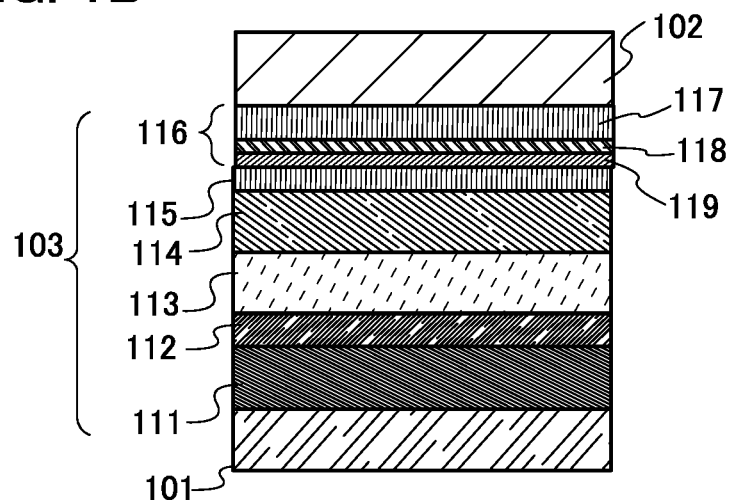

Instead of the electron-injection layer 115, the charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the cathode 102 serving as a cathode; thus, the EL device operates. Alternatively, the first layer can be used as the p-type layer 117. In this case, the p-type layer 117 with a low refractive index can be formed, and thus an EL device with high external quantum efficiency can be obtained.

Note that the charge-generation layer 116 preferably includes one or both of an electron-relay layer 118 and an electron-injection buffer layer 119 in addition to the p-type layer 117.

The electron-relay layer 118 contains at least a substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the electron-accepting substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV. Note that as the substance having an electron-transport property used for the electron-relay layer 118, a phthalocyanine-based material or a metal complex having a metal-oxygen bond and an aromatic ligand is preferably used.

A substance having a high electron-injection property, such as an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)), can be used for the electron-injection buffer layer 119.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

As a substance for forming the cathode 102, a metal, an alloy, an electrically conductive compound, or a mixture thereof each having a low work function (specifically, lower than or equal to 3.8 eV) or the like can be used. Specific examples of such a cathode material are elements belonging to Group 1 or Group 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the cathode 102 and the electron-transport layer, for the cathode 102, a variety of conductive materials such as Al, Ag, ITO, or indium oxide-tin oxide containing silicon or silicon oxide can be used regardless of the work function. Films of these conductive materials can be formed by a dry method such as a vacuum evaporation method or a sputtering method, an ink-jet method, a spin coating method, or the like. Alternatively, a wet method using a sol-gel method or a wet method using a paste of a metal material may be employed.

Furthermore, any of a variety of methods can be used for forming the EL layer 103, regardless of a dry method or a wet method. For example, a vacuum evaporation method, a gravure printing method, an offset printing method, a screen printing method, an ink-jet method, a spin coating method, or the like may be employed.

Different methods may be used to form each of the electrodes or layers described above.

The structure of the layers provided between the anode 101 and the cathode 102 is not limited to the above-described structure. Preferably, a light-emitting region where holes and electrons recombine is positioned away from the anode 101 and the cathode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of an EL device with a structure in which a plurality of light-emitting units are stacked (also referred to as a stacked-type element or a tandem element) will be described with reference to FIG. 1C. This EL device is an EL device including a plurality of light-emitting units between an anode and a cathode. One light-emitting unit has substantially the same structure as that of the EL layer 103, which is shown in FIG. 1A. In other words, the EL device shown in FIG. 1C is an EL device including a plurality of light-emitting units, and the EL device shown in FIG. 1A or FIG. 1B is an EL device including one light-emitting unit.

Figure 1C:
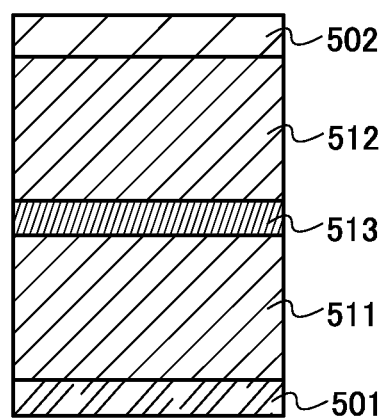

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the anode 101 and the cathode 102 in FIG. TA, and the materials given in the description for FIG. TA can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when voltage is applied between the anode 501 and the cathode 502. That is, in FIG. 1C, the charge-generation layer 513 injects electrons into the first light-emitting unit 511 and holes into the second light-emitting unit 512 when voltage is applied so that the potential of the anode becomes higher than the potential of the cathode.

The charge-generation layer 513 preferably has a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side and thus, an electron-injection layer is not necessarily formed in the light-emitting unit on the anode side.

The EL device having two light-emitting units is described with reference to FIG. 1C; however, one embodiment of the present invention can also be applied to an EL device in which three or more light-emitting units are stacked. With a plurality of light-emitting units partitioned by the charge-generation layer 513 between a pair of electrodes as in the EL device of this embodiment, it is possible to provide a long-life element which can emit light with high luminance at a low current density. A light-emitting apparatus which can be driven at a low voltage and has low power consumption can be achieved.

When the emission colors of the light-emitting units are different, light emission of a desired color can be obtained from the EL device as a whole. For example, in an EL device having two light-emitting units, the emission colors of the first light-emitting unit may be red and green and the emission color of the second light-emitting unit may be blue, so that the EL device can emit white light as the whole.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting apparatus using the EL device described in Embodiment 2 will be described.

Figure 2A:
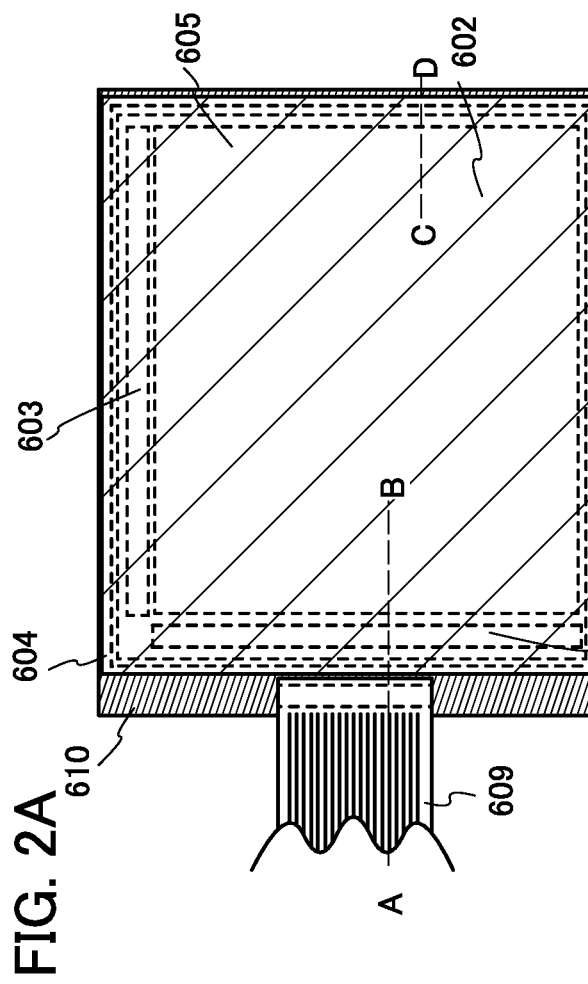
FIG. 2A and FIG. 2B are conceptual diagrams of an active matrix light-emitting apparatus.
Figure 2B:
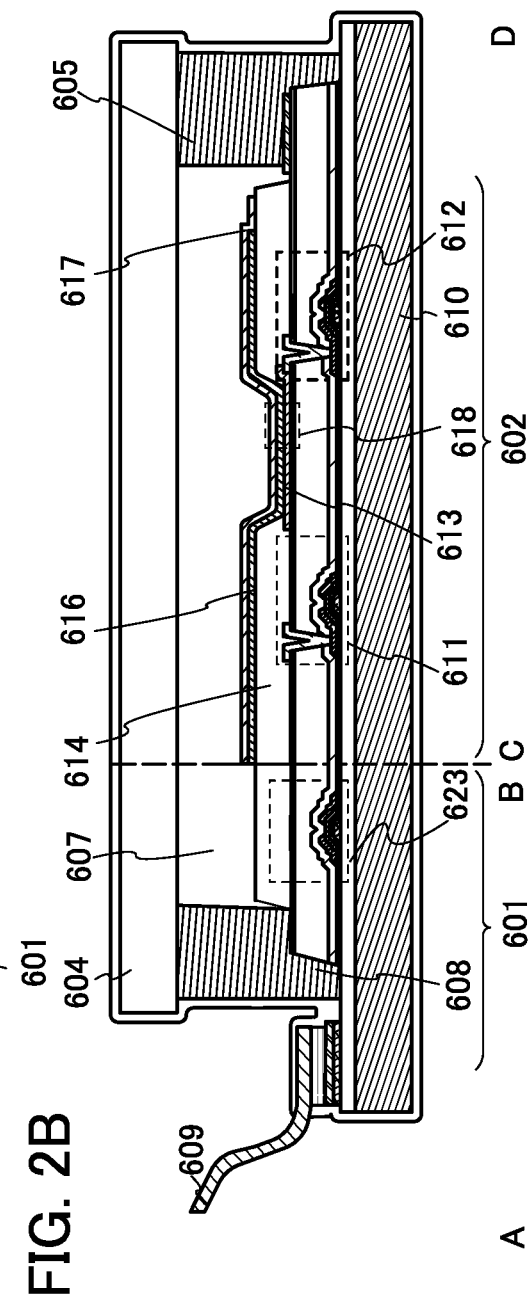

In this embodiment, a light-emitting apparatus fabricated using the EL device described in Embodiment 2 will be described with reference to FIG. 2. Note that FIG. 2A is a top view showing the light-emitting apparatus, and FIG. 2B is a cross-sectional view taken along the lines A-B and C-D in FIG. 2A. This light-emitting apparatus includes a driver circuit portion (source line driver circuit) 601, a pixel portion 602, and a driver circuit portion (gate line driver circuit) 603, which are for controlling light emission of an EL device and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting apparatus in this specification includes not only the light-emitting apparatus itself but also the apparatus provided with the FPC or the PWB.

Next, a cross-sectional structure will be described with reference to FIG. 2B. The driver circuit portion and the pixel portion are formed over an element substrate 610; here, the source line driver circuit 601, which is the driver circuit portion, and one pixel in the pixel portion 602 are shown.

The element substrate 610 may be fabricated using a substrate containing glass, quartz, an organic resin, a metal, an alloy, a semiconductor, or the like, or a plastic substrate formed of FRP (Fiber Reinforced Plastics), PVF (polyvinyl fluoride), polyester, an acrylic resin, or the like.

There is no particular limitation on the structure of transistors used in pixels and driver circuits. For example, an inverted staggered transistor or a staggered transistor may be used. Furthermore, top-gate transistors or bottom-gate transistors may be used. There is no particular limitation on a semiconductor material used for the transistors, and for example, silicon, germanium, silicon carbide, gallium nitride, or the like can be used. Alternatively, an oxide semiconductor containing at least one of indium, gallium, and zinc, such as In—Ga—Zn-based metal oxide, may be used.

There is no particular limitation on the crystallinity of a semiconductor material used for the transistors, and any of an amorphous semiconductor and a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. The use of an oxide semiconductor having a wider band gap than silicon can reduce the off-state current of the transistors.

The oxide semiconductor preferably contains at least indium (In) or zinc (Zn). Further preferably, the oxide semiconductor contains an oxide represented by an In-M-Zn-based oxide (M is a metal such as Al, Ti, Ga, Ge, Y, Zr, Sn, La, Ce, or Hf).

An oxide semiconductor that can be used in one embodiment of the present invention is described below.

Oxide semiconductors can be classified into a single crystal oxide semiconductor and a non-single-crystal oxide semiconductor. Examples of the non-single-crystal oxide semiconductor include a CAAC-OS (c-axis aligned crystalline oxide semiconductor), a polycrystalline oxide semiconductor, an nc-OS (nano crystalline oxide semiconductor), an amorphous-like oxide semiconductor (a-like OS), and an amorphous oxide semiconductor.

The CAAC-OS has c-axis alignment, a plurality of nanocrystals are connected in the a-b plane direction, and its crystal structure has distortion. Note that the distortion refers to a portion where the direction of a lattice arrangement changes between a region with a regular lattice arrangement and another region with a regular lattice arrangement in a region where the plurality of nanocrystals are connected.

The nanocrystal is basically a hexagon but is not always a regular hexagon and is a non-regular hexagon in some cases. Furthermore, a pentagonal or heptagonal lattice arrangement, for example, is included in the distortion in some cases. Note that it is difficult to observe a clear crystal grain boundary (also referred to as grain boundary) even in the vicinity of distortion in the CAAC-OS. That is, formation of a crystal grain boundary is found to be inhibited by the distortion of a lattice arrangement. This is because the CAAC-OS can tolerate distortion owing to a low density of arrangement of oxygen atoms in the a-b plane direction, an interatomic bond length changed by substitution of a metal element, and the like.

The CAAC-OS tends to have a layered crystal structure (also referred to as a layered structure) in which a layer containing indium and oxygen (hereinafter, an In layer) and a layer containing the element M, zinc, and oxygen (hereinafter, an (M,Zn) layer) are stacked. Note that indium and the element M can be replaced with each other, and when the element M in the (M,Zn) layer is replaced with indium, the layer can also be referred to as an (In,M,Zn) layer. Furthermore, when indium in the In layer is replaced with the element M, the layer can be referred to as an (In,M) layer.

The CAAC-OS is an oxide semiconductor with high crystallinity. On the other hand, a clear crystal grain boundary is difficult to observe in the CAAC-OS; thus, it can be said that a reduction in electron mobility due to the crystal grain boundary is less likely to occur. Entry of impurities, formation of defects, or the like might decrease the crystallinity of an oxide semiconductor; thus, it can be said that the CAAC-OS is an oxide semiconductor that has small amounts of impurities and defects (e.g., oxygen vacancies (also referred to as Vo)). Thus, an oxide semiconductor including the CAAC-OS is physically stable. Therefore, the oxide semiconductor including the CAAC-OS is resistant to heat and has high reliability.

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. Furthermore, there is no regularity of crystal orientation between different nanocrystals in the nc-OS. Thus, the orientation in the whole film is not observed. Accordingly, the nc-OS cannot be distinguished from an a-like OS or an amorphous oxide semiconductor by some analysis methods.

Note that indium-gallium-zinc oxide (hereinafter referred to as IGZO) that is a kind of oxide semiconductor containing indium, gallium, and zinc has a stable structure in some cases by being formed of the above-described nanocrystals. In particular, crystals of IGZO tend not to grow in the air and thus, a stable structure is obtained when IGZO is formed of smaller crystals (e.g., the above-described nanocrystals) rather than larger crystals (here, crystals with a size of several millimeters or several centimeters).

The a-like OS is an oxide semiconductor having a structure between those of the nc-OS and the amorphous oxide semiconductor. The a-like OS includes a void or a low-density region. That is, the a-like OS has low crystallinity compared with the nc-OS and the CAAC-OS.

An oxide semiconductor has various structures with different properties. Two or more of the amorphous oxide semiconductor, the polycrystalline oxide semiconductor, the a-like OS, the nc-OS, and the CAAC-OS may be included in an oxide semiconductor of one embodiment of the present invention.

As an oxide semiconductor other than the above, a CAC (Cloud-Aligned Composite)-OS may be used.

A CAC-OS has a conducting function in part of the material and has an insulating function in another part of the material; as a whole, the CAC-OS has a function of a semiconductor. Note that in the case where the CAC-OS is used in an active layer of a transistor, the conducting function is a function that allows electrons (or holes) serving as carriers to flow, and the insulating function is a function that does not allow electrons serving as carriers to flow. By the complementary action of the conducting function and the insulating function, a switching function (On/Off function) can be given to the CAC-OS. In the CAC-OS, separation of the functions can maximize each function.

In addition, the CAC-OS includes conductive regions and insulating regions. The conductive regions have the above-described conducting function, and the insulating regions have the above-described insulating function. Furthermore, in some cases, the conductive regions and the insulating regions in the material are separated at the nanoparticle level. Furthermore, in some cases, the conductive regions and the insulating regions are unevenly distributed in the material. Furthermore, in some cases, the conductive regions are observed to be coupled in a cloud-like manner with their boundaries blurred.

In the CAC-OS, the conductive regions and the insulating regions each have a size greater than or equal to 0.5 nm and less than or equal to 10 nm, preferably greater than or equal to 0.5 nm and less than or equal to 3 nm, and are dispersed in the material, in some cases.

The CAC-OS is composed of components having different band gaps. For example, the CAC-OS is composed of a component having a wide gap due to the insulating region and a component having a narrow gap due to the conductive region. In the case of the structure, when carriers flow, carriers mainly flow in the component having a narrow gap. Furthermore, the component having a narrow gap complements the component having a wide gap, and carriers also flow in the component having a wide gap in conjunction with the component having a narrow gap. Therefore, in the case where the above-described CAC-OS is used in a channel formation region of a transistor, the transistor in the on state can achieve high current driving capability, that is, high on-state current and high field-effect mobility.

In other words, the CAC-OS can also be referred to as a matrix composite or a metal matrix composite.

The use of the aforementioned oxide semiconductor material for the semiconductor layer makes it possible to achieve a highly reliable transistor in which a change in the electrical characteristics is reduced.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, an electronic apparatus with significantly reduced power consumption can be achieved.

For stable characteristics of the transistor, a base film is preferably provided. The base film can be formed to be a single layer or a stacked layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the driver circuit portion 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and a positive electrode 613 electrically connected to a drain of the current control FET 612; however, without being limited thereto, a pixel portion in which three or more FETs and a capacitor are combined may be employed.

Note that an insulator 614 is formed to cover an end portion of the positive electrode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where a positive photosensitive acrylic resin is used as a material for the insulator 614, only the upper end portion of the insulator 614 preferably has a curved surface with a curvature radius (0.2 µm to 3 µm). For the insulator 614, either a negative photosensitive resin or a positive photosensitive resin can be used.

An EL layer 616 and a negative electrode 617 are formed over the positive electrode 613. Here, as a material used for the positive electrode 613 functioning as a positive electrode, a material with a high work function is desirably used. For example, a single-layer film of an ITO film, an indium tin oxide film containing silicon, an indium oxide film containing zinc oxide at 2 to 20 wt %, a titanium nitride film, a chromium film, a tungsten film, a Zn film, a Pt film, or the like, a stacked layer of a titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. Alternatively, a material included in the EL layer 616 may be a low molecular compound or a high molecular compound (including an oligomer or a dendrimer).

As a material used for the negative electrode 617 functioning as a negative electrode, which is formed over the EL layer 616, a material with a low work function (e.g., Al, Mg, Li, Ca, or an alloy or a compound thereof (MgAg, MgIn, AlLi, or the like)) is preferably used. Note that in the case where light generated in the EL layer 616 passes through the negative electrode 617, it is preferable to use, for the negative electrode 617, a stacked layer of a thin metal film and a transparent conductive film (e.g., ITO, indium oxide containing zinc oxide at 2 to 20 wt %, indium tin oxide containing silicon, or zinc oxide (ZnO)).

Note that an EL device 618 is formed with the positive electrode 613, the EL layer 616, and the negative electrode 617. The EL device 618 is the EL device described in Embodiment 2. A plurality of EL devices are formed in the pixel portion, and the light-emitting apparatus of this embodiment may include both the EL device described in Embodiment 2 and an EL device having a different structure.

The sealing substrate 604 and the element substrate 610 are attached to each other using the sealant 605, achieving a structure in which the EL device 618 is provided in the space 607 surrounded by the element substrate 610, the sealing substrate 604, and the sealant 605. The space 607 is filled with a filler; it is filled with an inert gas (e.g., nitrogen or argon) in some cases, and filled with the sealant in some cases. The sealing substrate in which a recessed portion is formed and a desiccant is provided therein is preferable because deterioration due to the influence of moisture can be inhibited.

Note that an epoxy-based resin or glass frit is preferably used for the sealant 605. Furthermore, these materials are preferably materials that transmit moisture or oxygen as little as possible. For the sealing substrate 604, in addition to a glass substrate and a quartz substrate, a plastic substrate formed of FRP (Fiber Reinforced Plastics), PVF (polyvinyl fluoride), polyester, an acrylic resin, or the like can be used.

Although not shown in FIG. 2, a protective film may be provided over the cathode. As the protective film, an organic resin film or an inorganic insulating film can be formed. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is less likely to transmit an impurity such as water can be used. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, or indium oxide; or a material containing aluminum nitride, hafnium nitride, silicon nitride, tantalum nitride, titanium nitride, niobium nitride, molybdenum nitride, zirconium nitride, or gallium nitride; a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks and pinholes or with a uniform thickness can be formed. Furthermore, damage caused to a process member in forming the protective film can be reduced.

For example, by an ALD method, a uniform protective film with few defects can be formed even on a surface with a complex uneven shape or an upper surface, a side surface, and a lower surface of a touch panel.

The light-emitting apparatus fabricated using the EL device described in Embodiment 2 can be obtained in the above manner.

The light-emitting apparatus in this embodiment uses the EL device described in Embodiment 2 and thus has favorable characteristics. Specifically, since the light-emitting apparatus using the EL device described in Embodiment 2 has favorable emission efficiency, the light-emitting apparatus can achieve low power consumption.

FIG. 3 shows examples of a light-emitting apparatus which achieves full color display by formation of an EL device exhibiting white light emission and provision of coloring layers (color filters) and the like. FIG. 3A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, anodes 1024W, 1024R, 1024G, and 1024B of the EL devices, a partition 1025, an EL layer 1028, a negative electrode 1029 of the EL devices, a sealing substrate 1031, a sealant 1032, and the like.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3A, there is a light-emitting layer from which light is extracted to the outside without passing through the coloring layers and a light-emitting layer from which light is extracted to the outside after passing through the coloring layers of the respective colors, and the light that does not pass through the coloring layers is white, and the light that passes through the coloring layers is red, green, and blue, so that an image can be expressed with the pixels of four colors.

FIG. 3B shows an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 4:
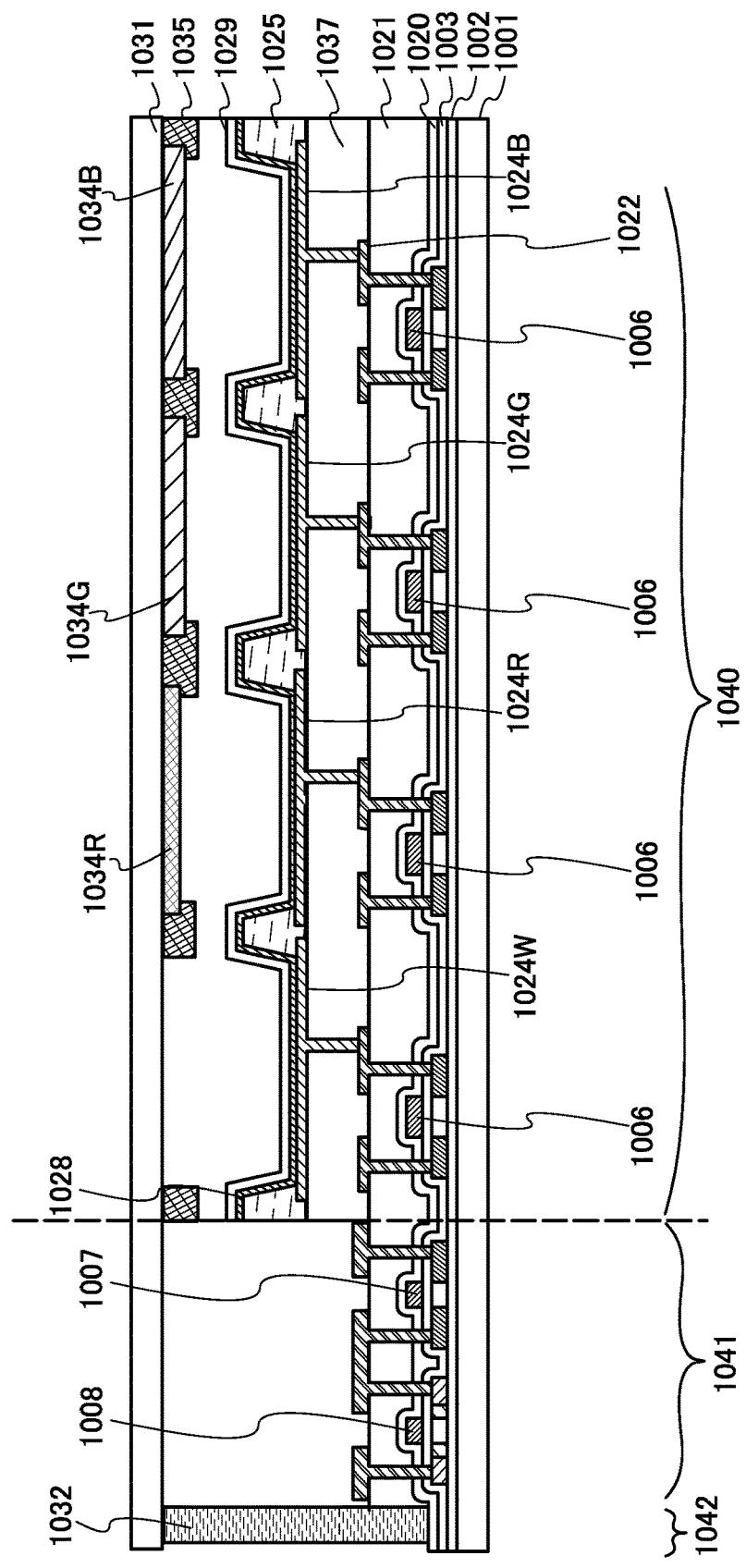
FIG. 4 is a conceptual diagram of an active matrix light-emitting apparatus.

The above-described light-emitting apparatus is a light-emitting apparatus having a structure in which light is extracted to the substrate 1001 side where the FETs are formed (a bottom-emission type), but may be a light-emitting apparatus having a structure in which light emission is extracted to the sealing substrate 1031 side (a top-emission type). FIG. 4 shows a cross-sectional view of a top-emission light-emitting apparatus. In this case, a substrate that does not transmit light can be used as the substrate 1001. The top-emission light-emitting apparatus is formed in a manner similar to that of the bottom-emission light-emitting apparatus until a connection electrode which connects the FET and the anode of the EL device is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The anodes 1024W, 1024R, 1024G, and 1024B of the EL devices may each be a cathode though they are anodes here. Furthermore, in the case of the top-emission light-emitting apparatus shown in FIG. 4, the anodes are preferably reflective electrodes. The EL layer 1028 has a structure similar to the structure of the EL layer 103 described in Embodiment 1, with which white light emission can be obtained.

In the top-emission structure as shown in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission light-emitting apparatus, a microcavity structure can be favorably employed. An EL device with a microcavity structure can be obtained with the use of a reflective electrode as the anode and a semi-transmissive and semi-reflective electrode as the cathode. At least an EL layer is provided between the reflective electrode and the semi-transmissive and semi-reflective electrode, and the EL layer includes at least a light-emitting layer functioning as a light-emitting region.

Note that the reflective electrode is a film having a visible light reflectance of 40% to 100%, preferably 70% to 100%, and a resistivity of $1 \times 10^{-2}$ Ωcm or lower. The semi-transmissive and semi-reflective electrode is a film having a visible light reflectance of 20% to 80%, preferably 40% to 70%, and a resistivity of $1 \times 10^{-2}$ Ωcm or lower.

Light emitted from the light-emitting layer included in the EL layer is reflected and resonated by the reflective electrode and the semi-transmissive and semi-reflective electrode.

In the EL device, by changing the thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to $(2n-1)\lambda/4$ (n is a natural number of 1 or larger and $\lambda$ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer; for example, in combination with the structure of the above-described tandem EL device, a plurality of EL layers each including a single or a plurality of light-emitting layer(s) may be provided in one EL device with a charge-generation layer interposed between the EL layers.

With the microcavity structure, emission intensity with a particular wavelength in the front direction can be increased, whereby power consumption can be reduced. Note that in the case of a light-emitting apparatus which displays images with subpixels of four colors of red, yellow, green, and blue, the light-emitting apparatus can have favorable characteristics because the luminance can be increased owing to yellow light emission and each subpixel can employ a microcavity structure suitable for the wavelength of the corresponding color.

The light-emitting apparatus in this embodiment uses the EL device described in Embodiment 2 and thus has favorable characteristics. Specifically, since the EL device described in Embodiment 2 has favorable emission efficiency, the light-emitting apparatus can achieve low power consumption.

Figure 5A:
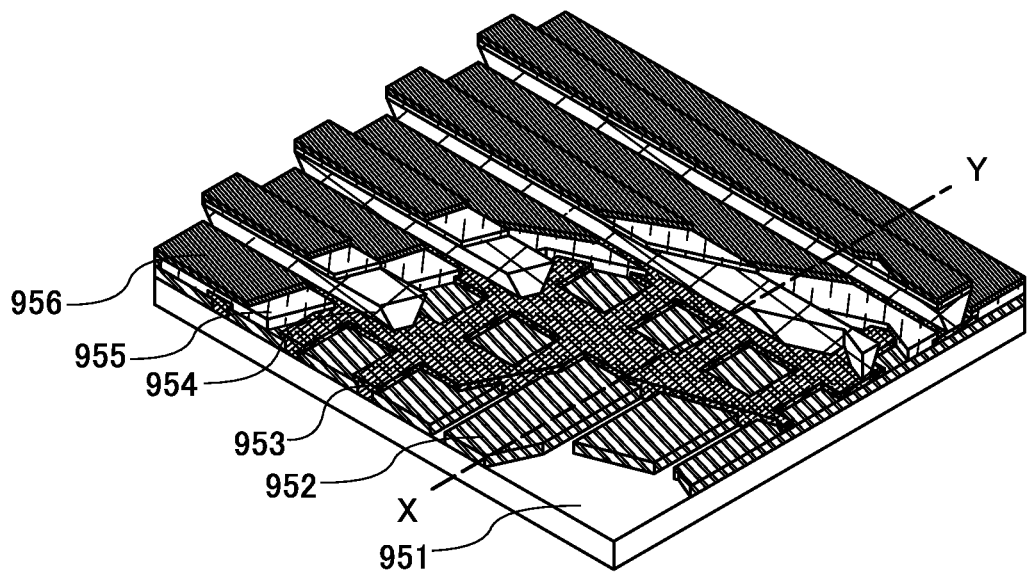
FIG. 5A and FIG. 5B are conceptual diagrams of a passive matrix light-emitting apparatus.
Figure 5B:
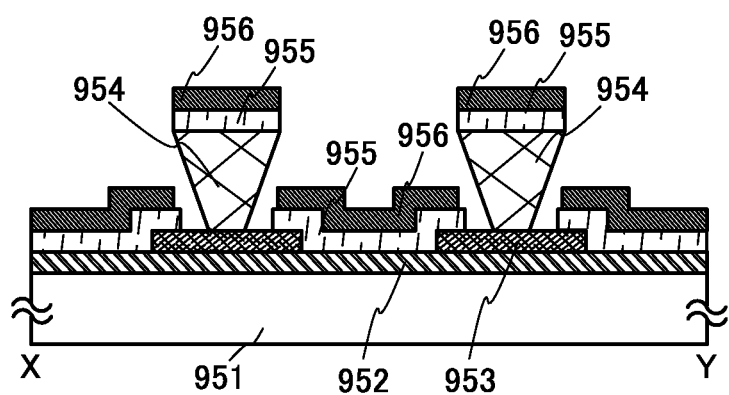

The active matrix light-emitting apparatus is described above, whereas a passive matrix light-emitting apparatus is described below. FIG. 5 illustrates a passive matrix light-emitting apparatus fabricated using the present invention. Note that FIG. 5A is a perspective view showing the light-emitting apparatus, and FIG. 5B is a cross-sectional view taken along the line X-Y in FIG. 5A. In FIG. 5, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). Providing the partition layer 954 in this manner can prevent defects of the EL device due to static charge or the like. The passive-matrix light-emitting apparatus also uses the EL device described in Embodiment 2; thus, the light-emitting apparatus can have favorable reliability or low power consumption.

Since many minute EL devices arranged in a matrix can be controlled in the above-described light-emitting apparatus, the light-emitting apparatus can be suitably used as a display device for expressing images.

This embodiment can be freely combined with any of the other embodiments.

Embodiment 4

Figure 6A:
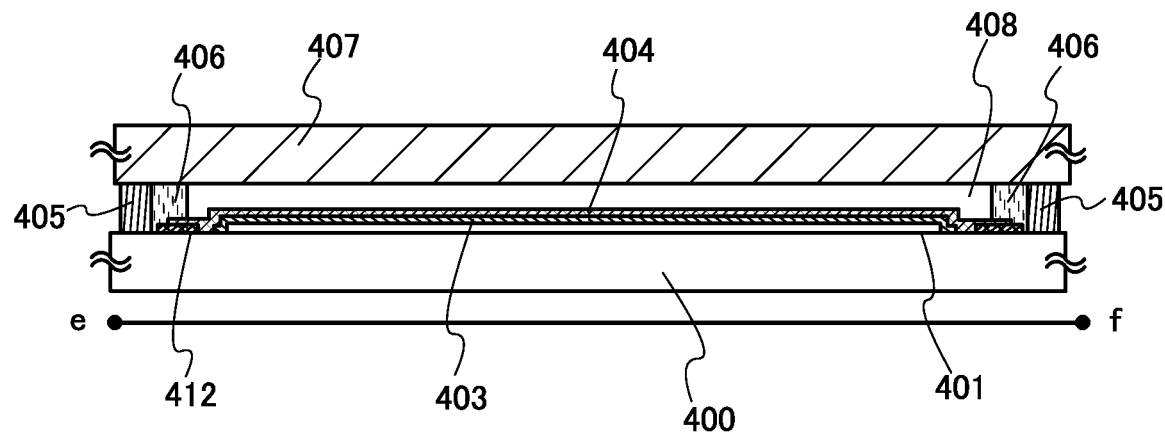
FIG. 6A and FIG. 6B are diagrams illustrating a lighting device.
Figure 6B:
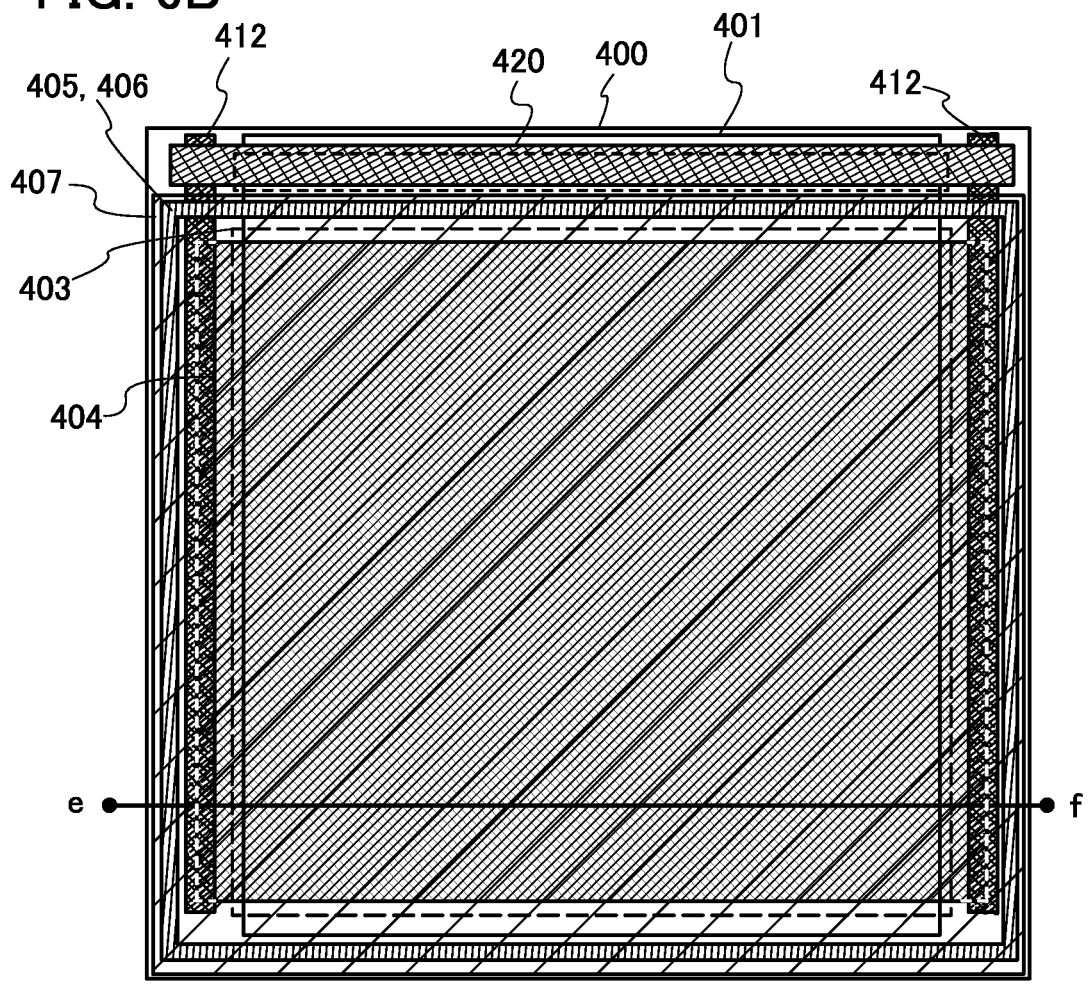

In this embodiment, an example in which the EL device described in Embodiment 2 is used for a lighting device will be described with reference to FIG. 6. FIG. 6B is a top view of the lighting device, and FIG. 6A is a cross-sectional view taken along the line e-f in FIG. 6B.

In the lighting device in this embodiment, an anode 401 is formed over a substrate 400 which is a support and has a light-transmitting property. The anode 401 corresponds to the anode 101 in Embodiment 1. When light is extracted through the anode 401 side, the anode 401 is formed of a material having a light-transmitting property.

A pad 412 for applying voltage to a cathode 404 is provided over the substrate 400.

An EL layer 403 is formed over the anode 401. The EL layer 403 has a structure corresponding to that of the EL layer 103 in Embodiment 1, or the structure in which the light-emitting units 511 and 512 are combined with the charge-generation layer 513. Note that for these structures, the corresponding description can be referred to.

The cathode 404 is formed to cover the EL layer 403. The cathode 404 corresponds to the cathode 102 in Embodiment 2. The cathode 404 is formed of a material having high reflectance when light is extracted through the anode 401 side. The cathode 404 is connected to the pad 412, whereby voltage is applied.

As described above, the lighting device described in this embodiment has an EL device having the anode 401, the EL layer 403, and the cathode 404. Since the EL device is an EL device with high emission efficiency, the lighting device in this embodiment can be a lighting device with low power consumption.

The substrate 400 over which the EL device having the above structure is formed is fixed to a sealing substrate 407 with sealants 405 and 406 and sealing is performed, whereby the lighting device is completed. It is possible to use only either the sealant 405 or 406. In addition, the inner sealant 406 (not illustrated in FIG. 6B) can be mixed with a desiccant, which enables moisture to be adsorbed, resulting in improved reliability.

When parts of the pad 412 and the anode 401 are extended to the outside of the sealants 405 and 406, those can serve as external input terminals. An IC chip 420 or the like mounted with a converter or the like may be provided over the external input terminals.

The lighting device described in this embodiment uses the EL device described in Embodiment 2 as an EL device; thus, the light-emitting apparatus can have low power consumption.

Embodiment 5

In this embodiment, examples of electronic appliances each partly including the EL device described in Embodiment 2 are described. The EL device described in Embodiment 2 has high emission efficiency and is an EL device with low power consumption. Thus, the electronic appliances described in this embodiment can be electronic appliances including light-emitting portions with low power consumption.

Examples of electronic appliances to which the EL device is applied include television devices (also referred to as TV or television receivers), monitors for computers and the like, digital cameras, digital video cameras, digital photo frames, cellular phones (also referred to as portable telephones or portable telephone devices), portable game machines, portable information terminals, audio playback devices, and large game machines such as pin-ball machines. Specific examples of these electronic appliances are shown below.

FIG. 7A shows an example of a television device. In the television device, a display portion 7103 is incorporated in a housing 7101. Here, a structure in which the housing 7101 is supported by a stand 7105 is shown. Images can be displayed on the display portion 7103, and the EL devices described in Embodiment 2 are arranged in a matrix in the display portion 7103.

The television device can be operated with an operation switch of the housing 7101 or a separate remote controller 7110. With operation keys 7109 of the remote controller 7110, channels and volume can be adjusted and images displayed on the display portion 7103 can be adjusted. Furthermore, a structure may be employed in which the remote controller 7110 is provided with a display portion 7107 for displaying data output from the remote controller 7110.

Note that the television device has a structure including a receiver, a modem, and the like. With the use of the receiver, a general television broadcast can be received, and when the television device is further connected to a communication network with or without a wire via the modem, one-way (from a sender to a receiver) or two-way (between a sender and a receiver or between receivers) data communication can be performed.

FIG. 7B1 is a computer which includes a main body 7201, a housing 7202, a display portion 7203, a keyboard 7204, an external connection port 7205, a pointing device 7206, and the like. Note that this computer is fabricated using the EL devices described in Embodiment 2 arranged in a matrix in the display portion 7203. The computer in FIG. 7B1 may be such a mode as in FIG. 7B2. The computer in FIG. 7B2 is provided with a second display portion 7210 instead of the keyboard 7204 and the pointing device 7206. The second display portion 7210 is of a touch-panel type, and input can be performed by adjusting display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

FIG. 7C shows an example of a portable terminal. A cellular phone includes operation buttons 7403, an external connection port 7404, a speaker 7405, a microphone 7406, and the like in addition to a display portion 7402 incorporated in a housing 7401. Note that the mobile phone includes the display portion 7402 which is fabricated by arranging the EL devices described in Embodiment 2 in a matrix.

The portable terminal shown in FIG. 7C may have a structure in which data can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting data such as text. The third one is a display+input mode in which the two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation (vertical or horizontal) of the portable terminal.

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, when a backlight which emits near-infrared light or a sensing light source which emits near-infrared light is used in the display portion, an image of a finger vein, a palm vein, or the like can be taken.

Note that the structures described in this embodiment can be combined with any of the structures described in Embodiment 1 to Embodiment 4 as appropriate.

As described above, the application range of the light-emitting apparatus including the EL device described in Embodiment 2 is wide so that this light-emitting apparatus can be applied to electronic appliances in a variety of fields. With the use of the EL device described in Embodiment 2, an electronic appliance with low power consumption can be obtained.

Figure 8A:
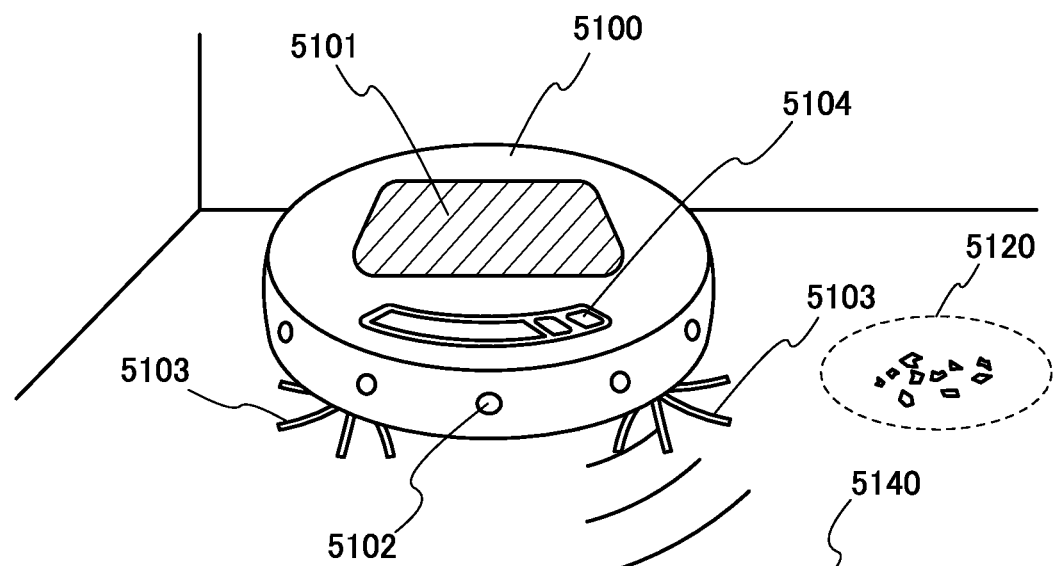
FIG. 8A to FIG. 8C are diagrams illustrating electronic appliances.

FIG. 8A is a schematic diagram showing an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. The cleaning robot 5100 also includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can analyze images taken by the cameras 5102 to judge whether there is an obstacle such as a wall, furniture, or a step. When an object such as a wire that is likely to be caught in the brush 5103 is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic appliance 5140 such as a smartphone. The portable electronic appliance 5140 can display images taken by the cameras 5102. Accordingly, an owner of the cleaning robot 5100 can monitor the room even from the outside. The display on the display 5101 can be checked by the portable electronic appliance such as a smartphone.

The light-emitting apparatus of one embodiment of the present invention can be used for the display 5101.

Figure 8B:
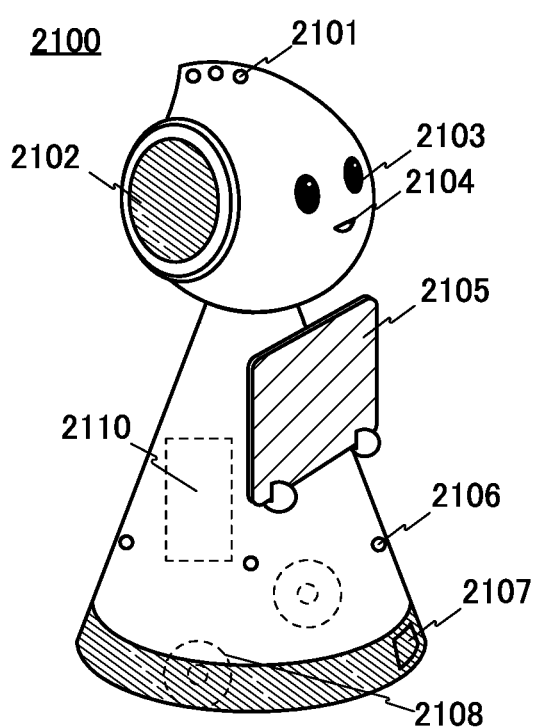

A robot 2100 illustrated in FIG. 8B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of data. The robot 2100 can display data desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
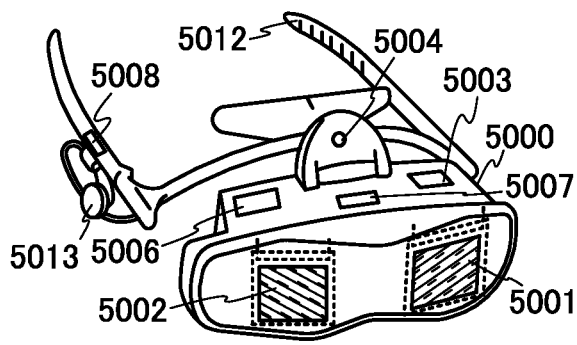

FIG. 8C shows an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone 5008, a display portion 5002, a support 5012, and an earphone 5013.

The light-emitting apparatus of one embodiment of the present invention can be used for the display portion 5001 and the second display portion 5002.

Figure 9:
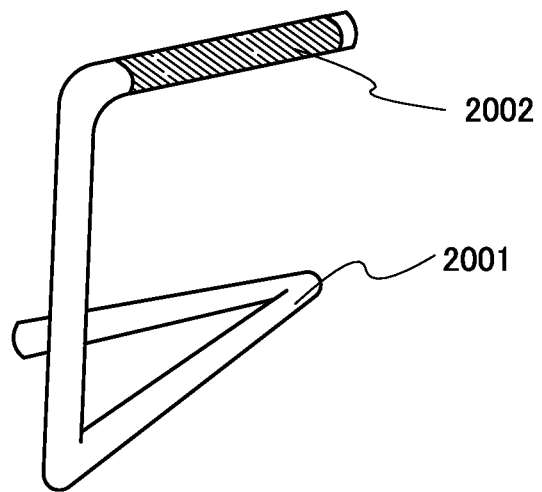
FIG. 9 is a diagram illustrating a lighting device.

FIG. 9 shows an example in which the EL device described in Embodiment 2 is used for a table lamp which is a lighting device. The table lamp shown in FIG. 9 includes a housing 2001 and a light source 2002, and the lighting device described in Embodiment 3 may be used for the light source 2002.

Figure 10:
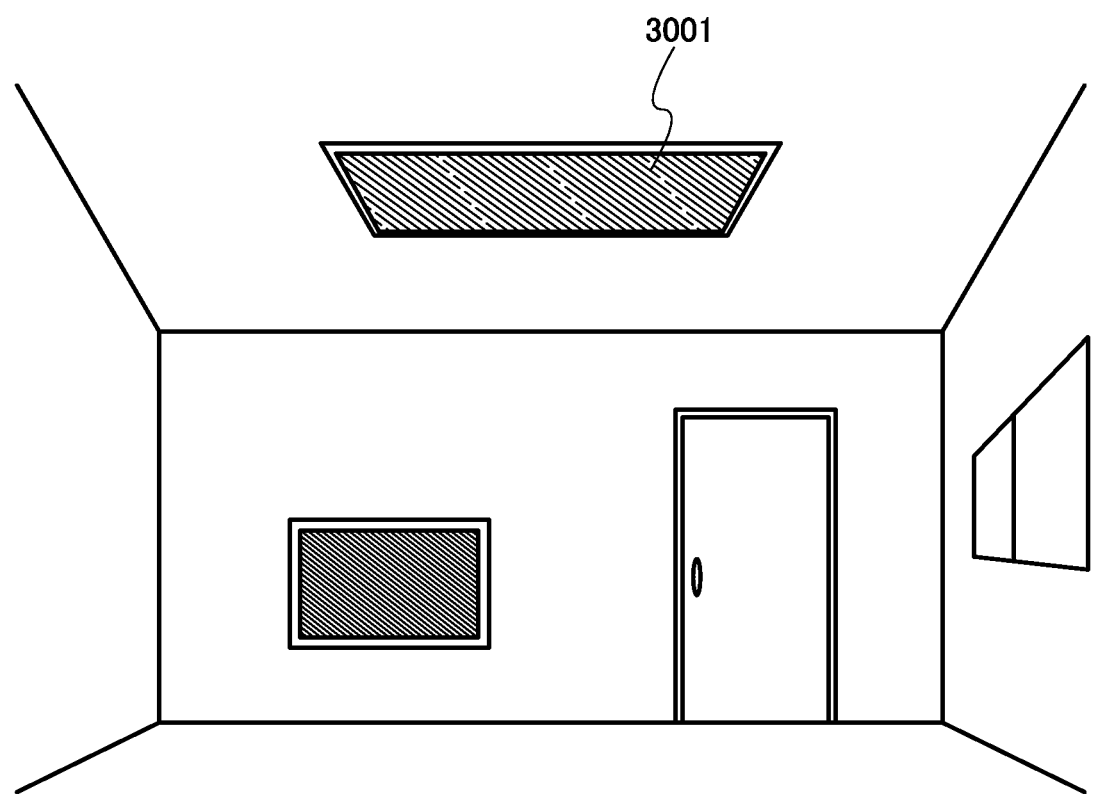
FIG. 10 is a diagram illustrating a lighting device.

FIG. 10 shows an example in which the EL device described in Embodiment 2 is used for an indoor lighting device 3001. Since the EL device described in Embodiment 2 is an EL device having high emission efficiency, the lighting device can have low power consumption. Furthermore, the EL device described in Embodiment 2 can have a larger area, and thus can be used for a large-area lighting device. Furthermore, the EL device described in Embodiment 2 is thin, and thus can be used for a lighting device having a reduced thickness.

Figure 11:
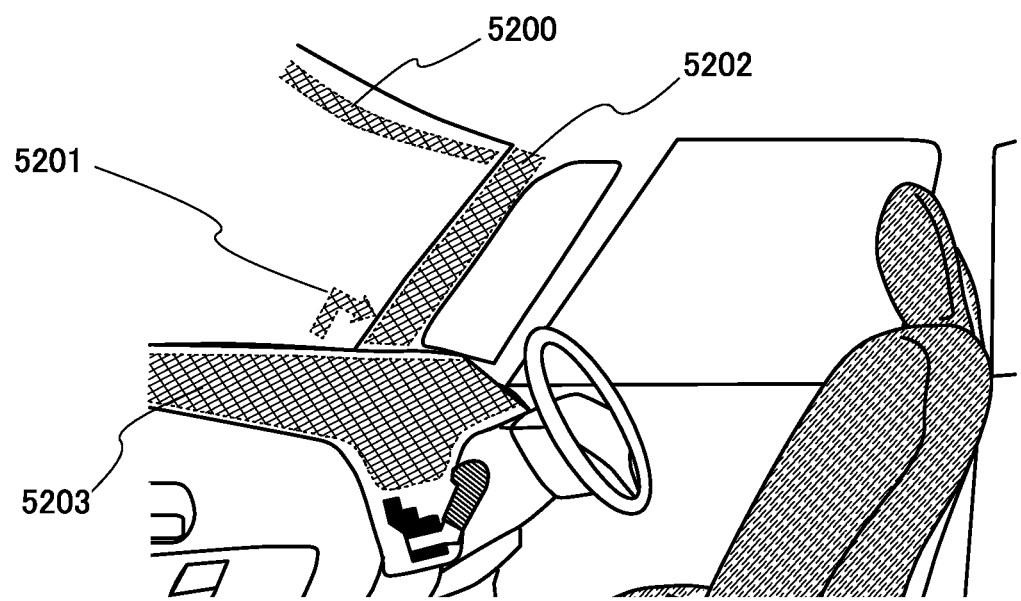
FIG. 11 is a diagram illustrating in-vehicle display devices and lighting devices.

The EL device described in Embodiment 2 can also be incorporated in a windshield or a dashboard of an automobile. FIG. 11 illustrates one mode in which the EL device described in Embodiment 2 is used for a windshield and a dashboard of an automobile. The EL device described in Embodiment 2 is used for each of a display region 5200 to a display region 5203.

The display region 5200 and the display region 5201 are display devices provided in the windshield of the automobile, in which the EL devices described in Embodiment 2 are incorporated. When the EL devices described in Embodiment 2 are fabricated using electrodes having light-transmitting properties as an anode and a cathode, what is called see-through display devices, through which the opposite side can be seen, can be obtained. See-through display can be provided even in the windshield of the automobile without hindering the vision. Note that in the case where a driving transistor or the like is provided, it is preferable to use a transistor having a light-transmitting property, such as an organic transistor using an organic semiconductor material or a transistor using an oxide semiconductor.

The display region 5202 is a display device provided in a pillar portion, in which the EL devices described in Embodiment 2 are incorporated. The display region 5202 can display an image taken by an imaging means provided on the automobile body to compensate for the view hindered by the pillar. Similarly, the display region 5203 provided in the dashboard portion can display an image taken by an imaging means provided on the outside of the automobile, so that the view hindered by the car body can be compensated for to avoid blind areas and enhance the safety. Showing an image so as to compensate for the area that cannot be seen makes it possible to confirm safety more naturally and comfortably.

The display region 5203 can provide a variety of kinds of information by displaying navigation data, a speedometer, a tachometer, a mileage, a fuel meter, a gearshift state, air-condition setting, and the like. The content or layout of the display can be changed freely in accordance with the preference of a user. Note that such information can also be displayed on the display region 5200 to the display region 5202. The display region 5200 to the display region 5203 can also be used as lighting devices.

Figure 12A:
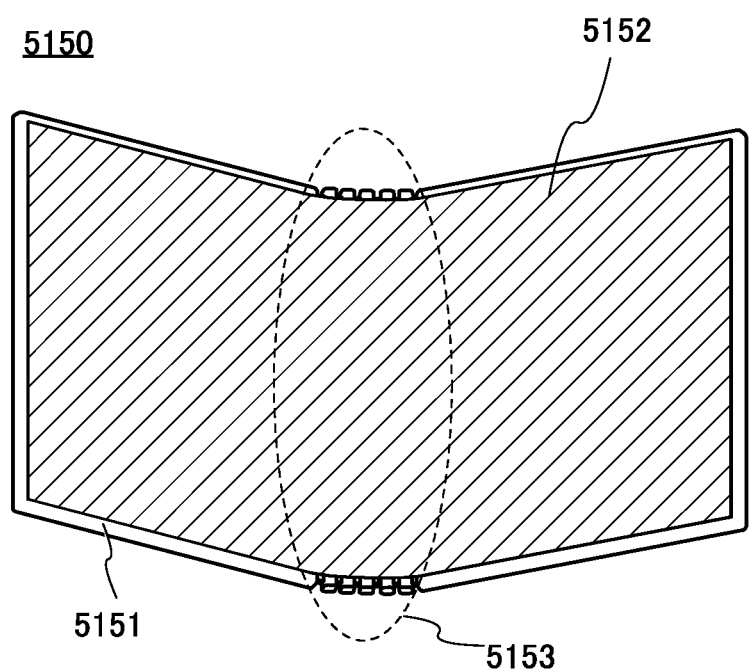
FIG. 12A and FIG. 12B are diagrams illustrating electronic appliances.
Figure 12B:
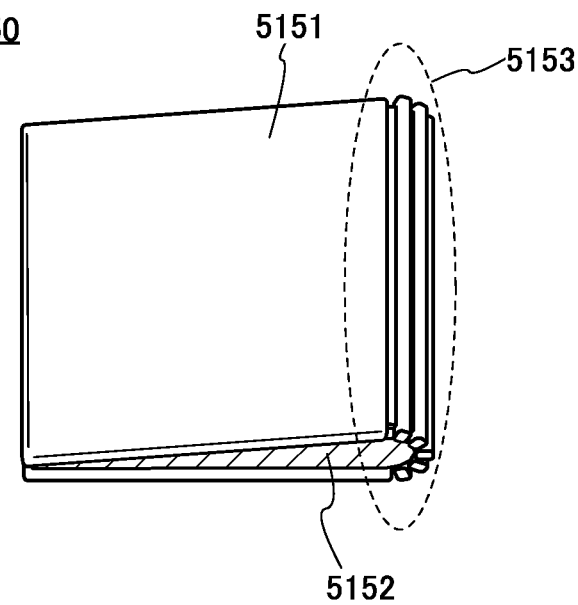

FIG. 12A and FIG. 12B illustrate a foldable portable information terminal 5150. The foldable portable information terminal 5150 includes a housing 5151, a display region 5152, and a bend portion 5153. FIG. 12A illustrates the portable information terminal 5150 that is opened. FIG. 12B illustrates the portable information terminal 5150 that is folded. The portable information terminal 5150 is compact in size and has excellent portability when folded, despite its large display region 5152.

The display region 5152 can be folded in half with the bend portion 5153. The bend portion 5153 is made up of a flexible member and a plurality of supporting members, and when the display region 5152 is folded, the flexible member is stretched. The bend portion 5153 has a radius of curvature of greater than or equal to 2 mm, preferably greater than or equal to 3 mm when folded.

Note that the display region 5152 may be a touch panel (an input/output device) including a touch sensor (an input device). The light-emitting apparatus of one embodiment of the present invention can be used for the display region 5152.

Figure 13A:
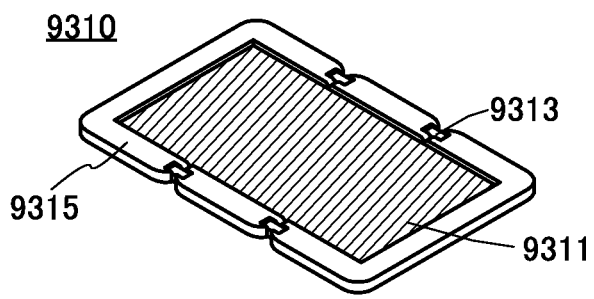
FIG. 13A to FIG. 13C are diagrams illustrating an electronic appliance.
Figure 13B:
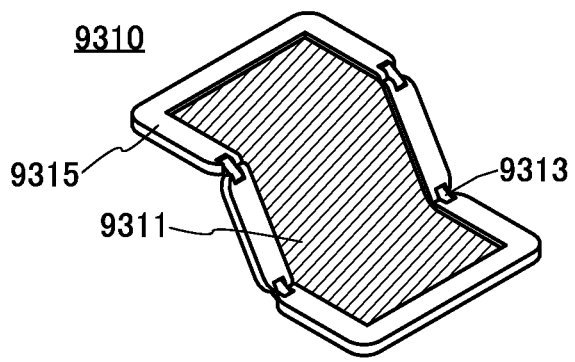
Figure 13C:
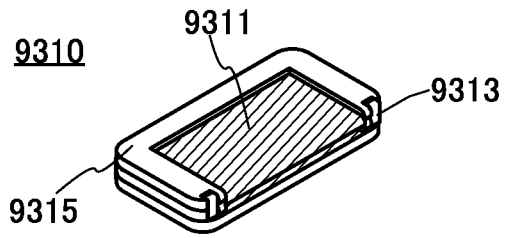

FIG. 13A to FIG. 13C illustrate a foldable portable information terminal 9310. FIG. 13A illustrates the portable information terminal 9310 that is opened. FIG. 13B illustrates the portable information terminal 9310 which is in the state of being changed from one of an opened state and a folded state to the other. FIG. 13C illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting apparatus of one embodiment of the present invention can be used for the display panel 9311.

Example 1

<<Synthesis Example 1>>

In this example, a synthesis method of 10-(2,2',3,3',4',5,5',6,6'-nonafluoro-4-biphenylyl)9,9-diphenyl-9H,10H-acridine (abbreviation: F9BPPad) and 10,10'-(2,2',3,3',5,5',6,6'-octafluorobiphenylen-4,4'-diyl)bis(9,9-diphenyl-9H,10H-acridine) (abbreviation: Pad2F8BP), which are organic compounds of embodiments of the present invention, will be described. The structures of F9BPPad and Pad2F8BP are shown below.

[Chemical Formulae 30]

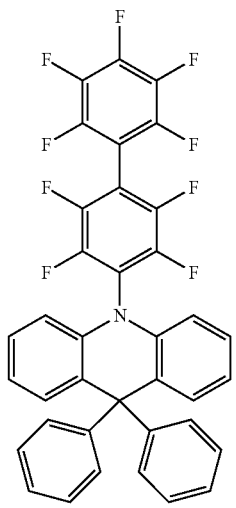

(100)

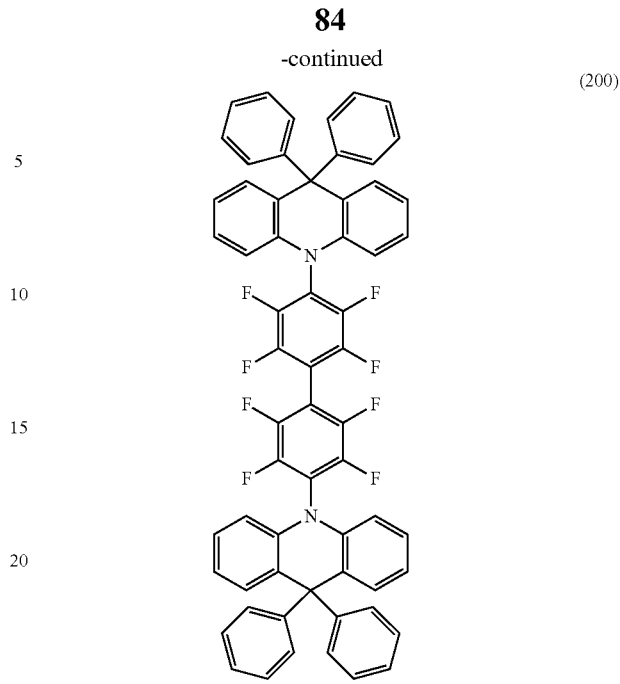

(200)

<Step 1: Synthesis of 10-(2,2',3,3',4',5,5',6,6'-nonafluoro-4-biphenylyl)9,9-diphenyl-9H,10H-acridine and 10,10'-(2,2',3,3',5,5',6,6'-octafluorobiphenylen-4,4'-diyl)bis(9,9-diphenyl-9H,10H-acridine)>

Into a three-neck flask, 0.41 g (16.5 mmol) of lithium amide was put, pressure reducing operation was performed once, and then the air in the flask was replaced with nitrogen. Into this flask, 15 mL of dehydrated THF was added, and stirring was performed. Into this suspension, 45 mL of a THF solution of 5.0 g (15 mmol) of 9,9-diphenyl-10H-acridine was dropped with use of a syringe. This mixed suspension was stirred at room temperature for approximately three hours to cause reaction. This mixture was cooled to −78° C. After the cooling, 15 mL of a THF solution of 5.0 g (15 mmol) of decafluorobiphenyl was dropped into this mixture with use of a syringe to cause reaction for approximately two hours. The temperature of this mixture was raised to room temperature, and stirring was performed overnight. After the stirring, approximately 50 mL of water was added to this mixture, and the mixture was separated. The obtained aqueous layer was extracted with ethyl acetate. The organic layer obtained by the separation and the ethyl acetate obtained by the extraction were mixed, washed with a saturated aqueous solution of sodium hydrogen carbonate, and then separated. The obtained organic layer was dried with magnesium sulfate and then separated by filtration, and the solvent was distilled off by an evaporator. The obtained mixture was separated and purified by silica gel column chromatography to give two kinds of white solids. One of the obtained two kinds of white solids was 3.2 g (4.95 mmol) of 10-(2,2',3,3',4',5,5',6,6'-nonafluoro-4-biphenylyl)9,9-diphenyl-9H,10H-acridine (abbreviation: F9BPPad) (in a yield of 33%), and the other was 3.1 g (3.20 mmol) of 10,10'-(2,2',3,3',5,5',6,6'-octafluorobiphenylen-4,4'-diyl)bis(9,9-diphenyl-9H,10H-acridine) (abbreviation: Pad2F8BP) (in a yield of 43%). The synthesis scheme of Step 1 is shown below.

[Chemical Formula 31]

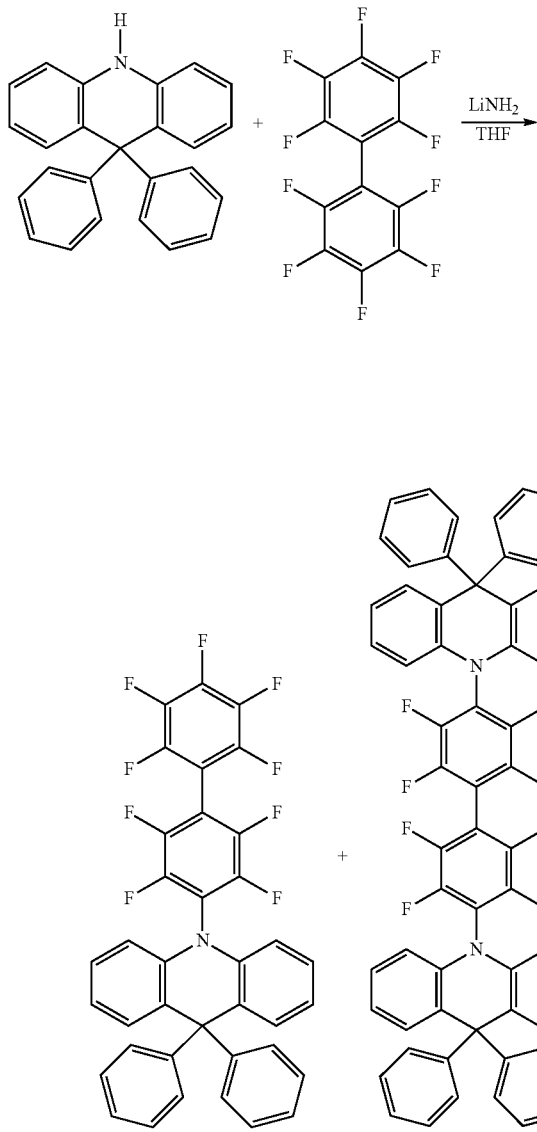

Figure 14A:
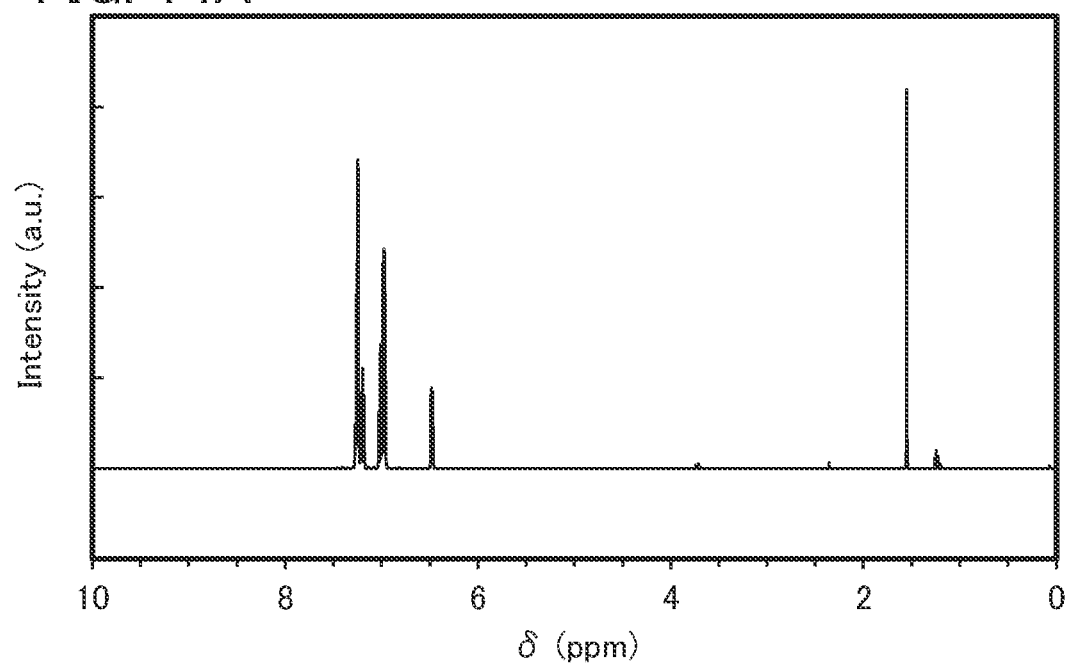
FIG. 14A and FIG. 14B are $^1$H NMR charts of F9BPPad.
Figure 14B:
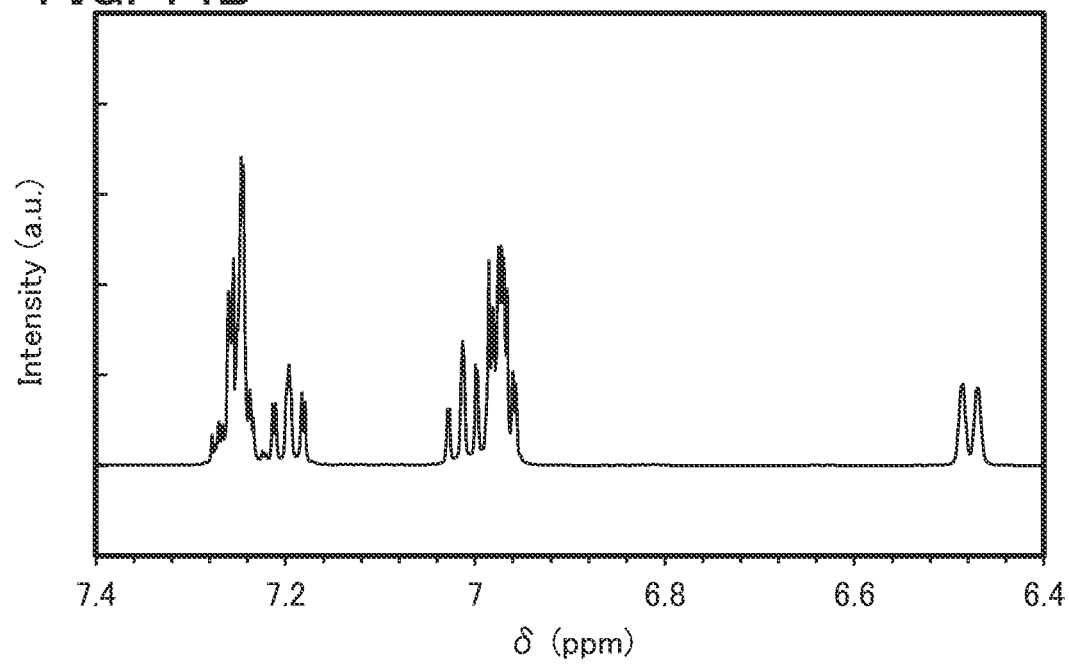
Figure 15A:
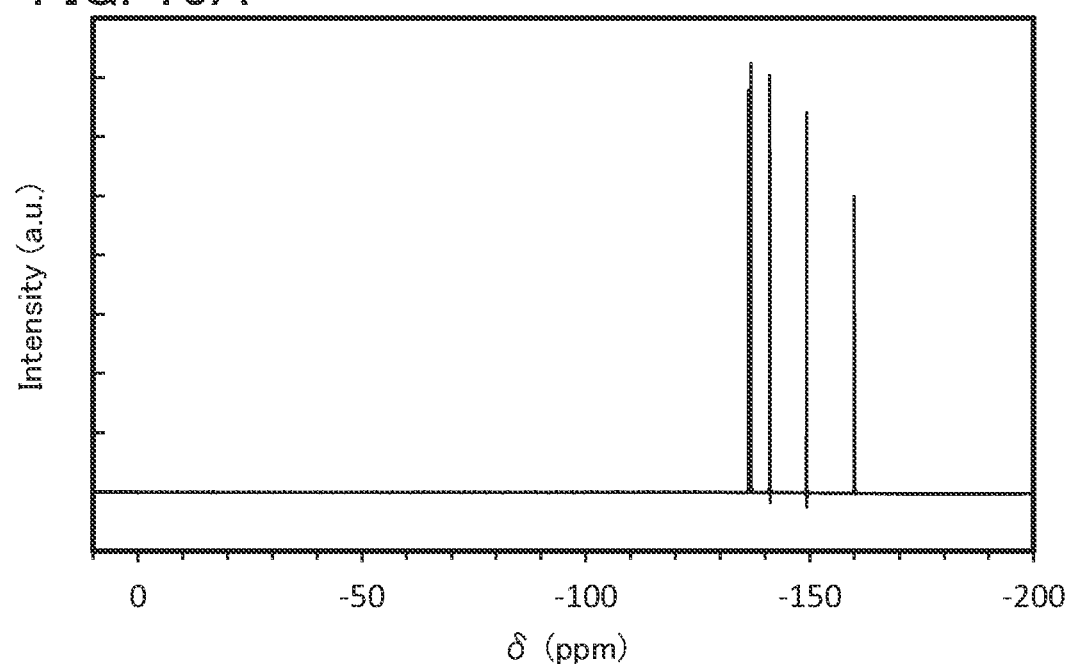
FIG. 15A and FIG. 15B are $^{19}$F-NMR charts of F9BPPad.
Figure 15B:
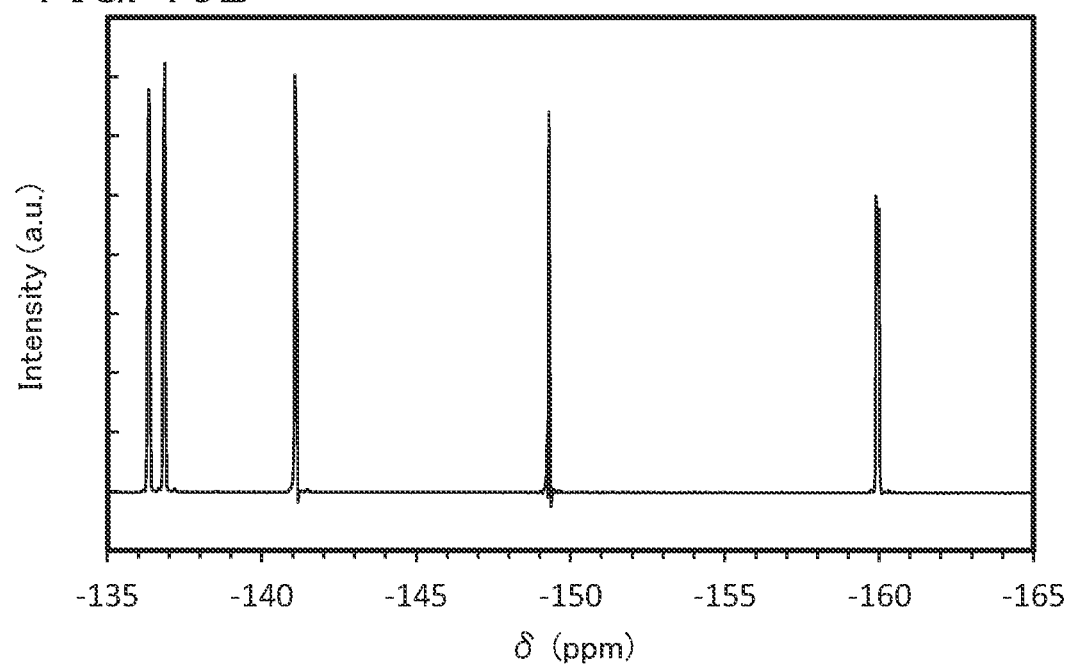
Figure 16A:
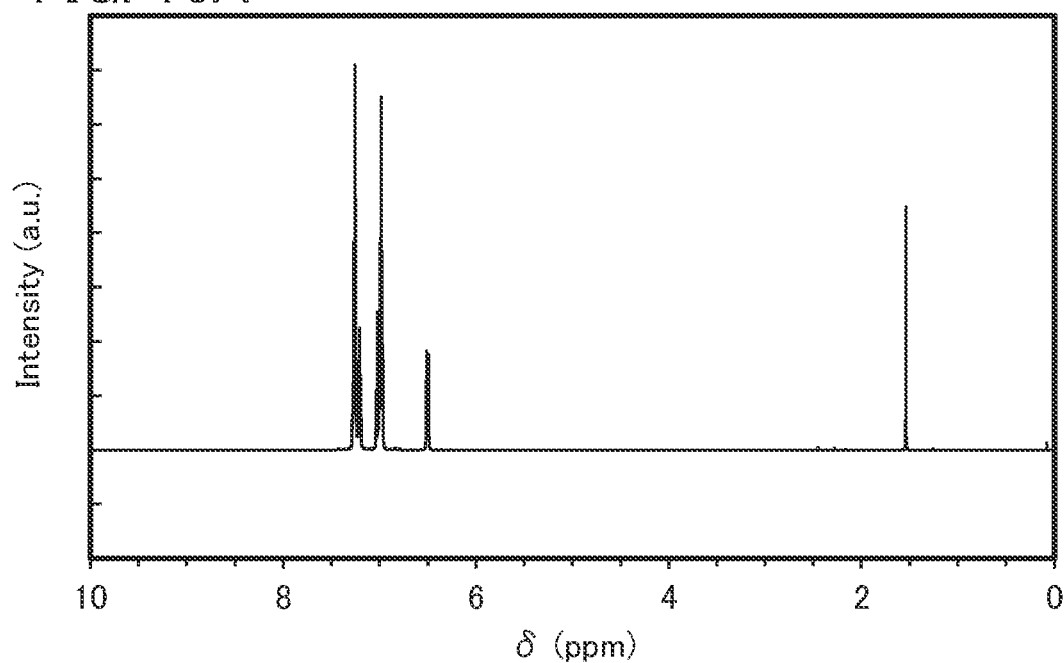
FIG. 16A and FIG. 16B are $^1$H NMR charts of Pad2F8BP.
Figure 16B:
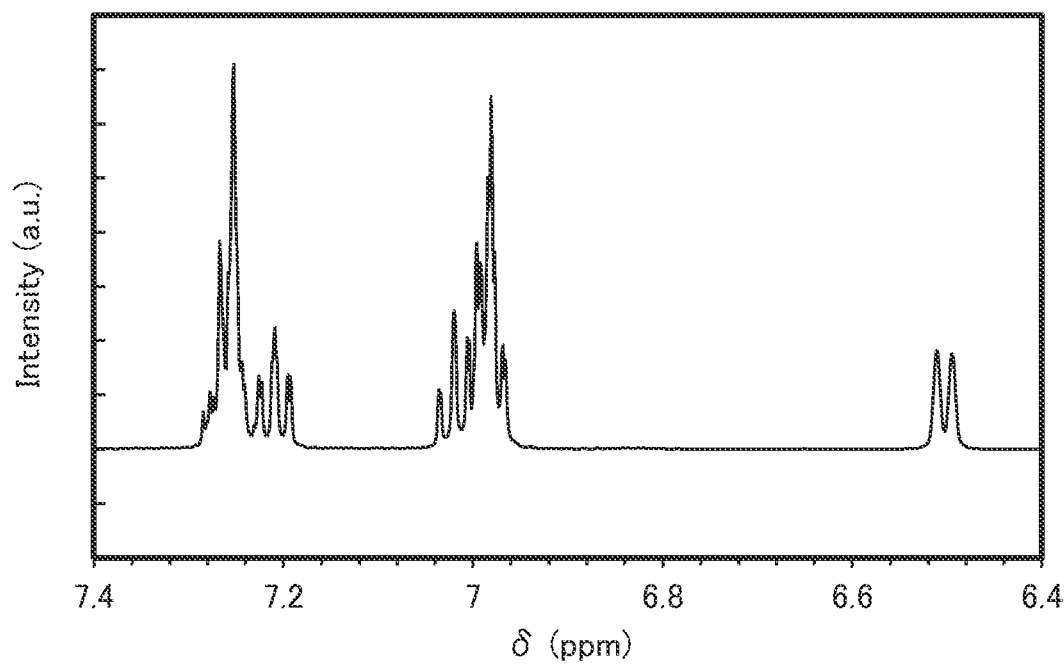
Figure 17A:
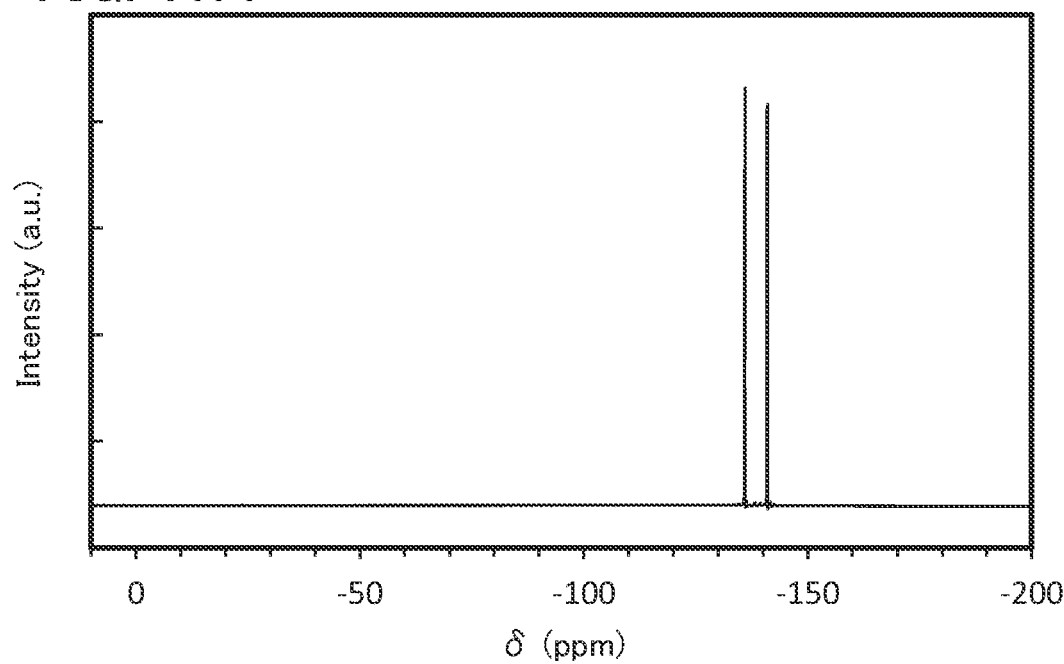
FIG. 17A and FIG. 17B are $^{19}$F-NMR charts of Pad2F8BP.
Figure 17B:
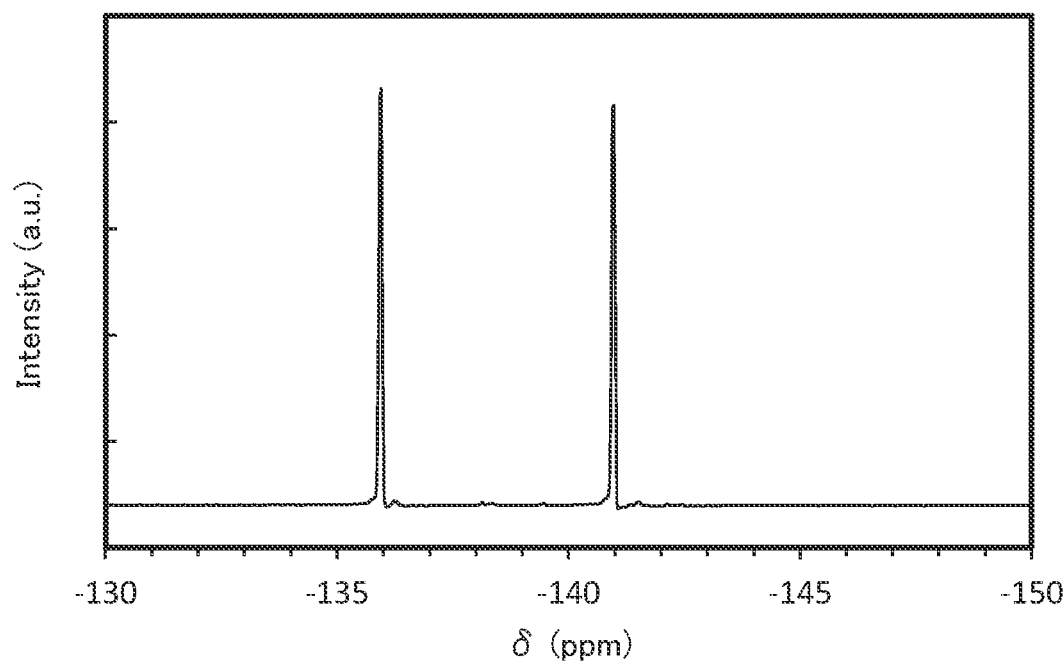

The white solids obtained in Step 1 described above were subjected to analyses by nuclear magnetic resonance spectroscopy ($^1$H-NMR and $^{19}$F-NMR). Numerical data is shown below. In addition, FIG. 14A and FIG. 14B show $^1$H-NMR charts of F9BPPad, FIG. 15A and FIG. 15B show $^{19}$F-NMR charts, FIG. 16A and FIG. 16B show $^1$H-NMR charts of Pad2F8BP, and FIG. 17A and FIG. 17B show $^{19}$F-NMR charts. The results show that 10-(2,2',3,3',4',5,5',6,6'-nonafluoro-4-biphenylyl)9,9-diphenyl-9H,10H-acridine and 10,10'-(2,2',3,3',5,5',6,6'-octafluorobiphenylen-4,4'-diyl)bis(9,9-diphenyl-9H,10H-acridine) were synthesized by the synthesis method of Step 1.

F9BPPad $^1$H-NMR. δ (CDCl$_3$): 7.17-7.28 (m, 8H), 6.94-7.04 (m, 8H), 6.48 (d, 2H, J=7.5 Hz).

$^{19}$F-NMR. δ (CDCl$_3$): −159.9, −149.3, −141.7, −136.9, −136.3.

Pad2F8BP $^1$H-NMR. δ (CDCl$_3$): 7.18-7.29 (m, 16H), 6.95-7.05 (m, 16H), 6.50 (d, 4H, J=8.0 Hz).

$^{19}$F-NMR. δ (CDCl$_3$): −141.0, −136.0.

Next, by a train sublimation method, the obtained solids were sublimated and purified. The sublimation purification was performed by heating 3.1 g of the solid of F9BPPad at 195° C. under the conditions where the pressure was 3.0 Pa and the argon flow rate was 17.9 mL/min, whereby 2.9 g of a white crystalline solid was obtained at a collection rate of 94%. In addition, the sublimation purification was performed by heating 3.0 g of the solid of Pad2F8BP at 290° C. under the conditions where the pressure was 3.0 Pa and the argon flow rate was 18.8 mL/min, whereby 2.6 g of a white solid was obtained at a collection rate of 89%.

Figure 19:
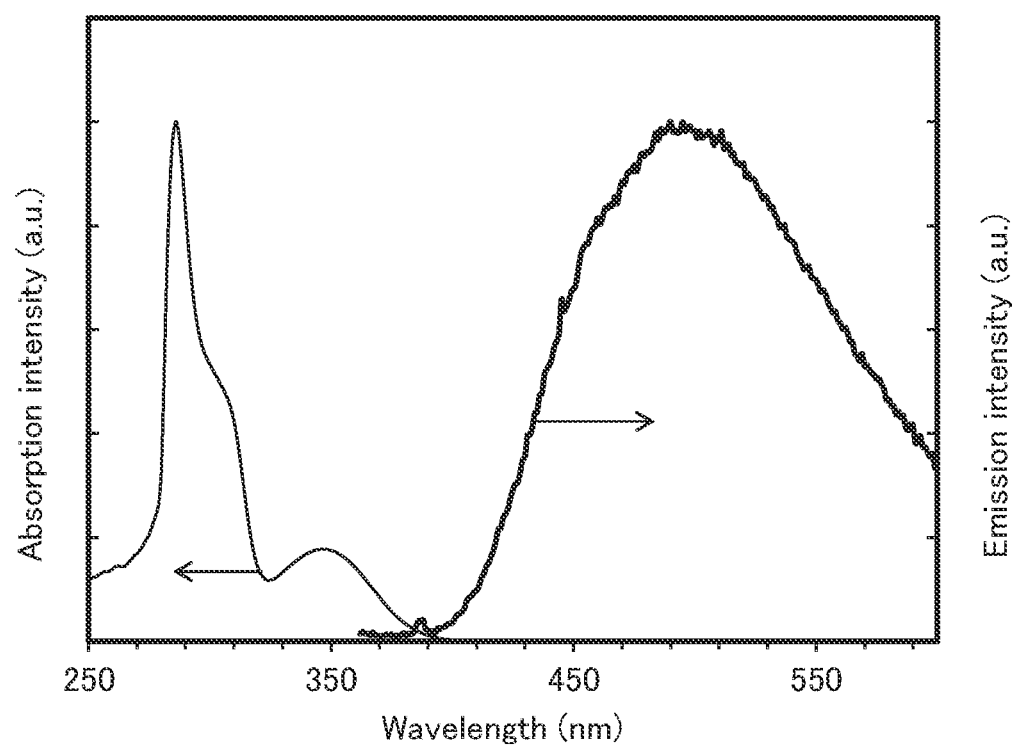
FIG. 19 shows an absorption spectrum and an emission spectrum of F9BPPad in a toluene solution.
Figure 20:
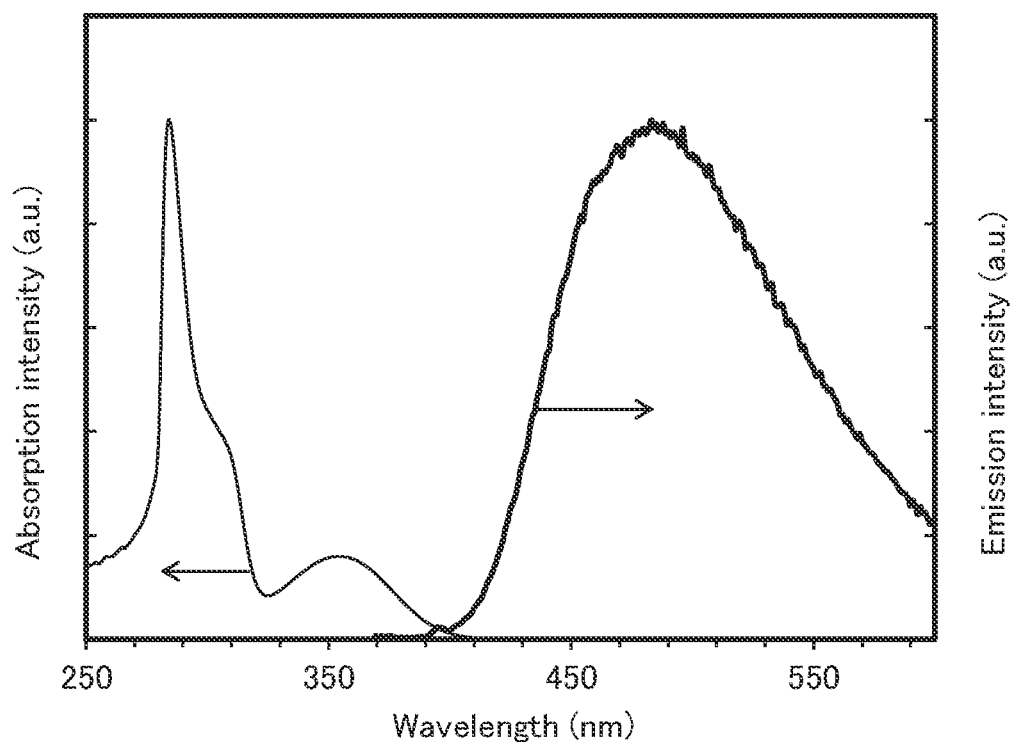
FIG. 20 shows an absorption spectrum and an emission spectrum of Pad2F8BP in a toluene solution.

Next, FIG. 19 shows an absorption spectrum and an emission spectrum of F9BPPad in a toluene solution and FIG. 20 shows an absorption spectrum and an emission spectrum of Pad2F8BP in a toluene solution.

Then, F9BPPad and Pad2F8BP obtained in this example were analyzed by liquid chromatography mass spectrometry (abbreviation: LC/MS analysis).

In the LC/MS analysis, LC (liquid chromatography) separation was carried out with Ultimate 3000 produced by Thermo Fisher Scientific K.K., and the MS analysis (mass analysis) was carried out with Q Exactive produced by Thermo Fisher Scientific K.K.

In the LC separation, a given column was used at a column temperature of 40° C., and the solution sending conditions were that an appropriate solvent was selected, the sample was adjusted by dissolving F9BPPad and Pad2F8BP in an organic solvent at a given concentration, and the injection amount was 5.0 μL.

Figure 29:
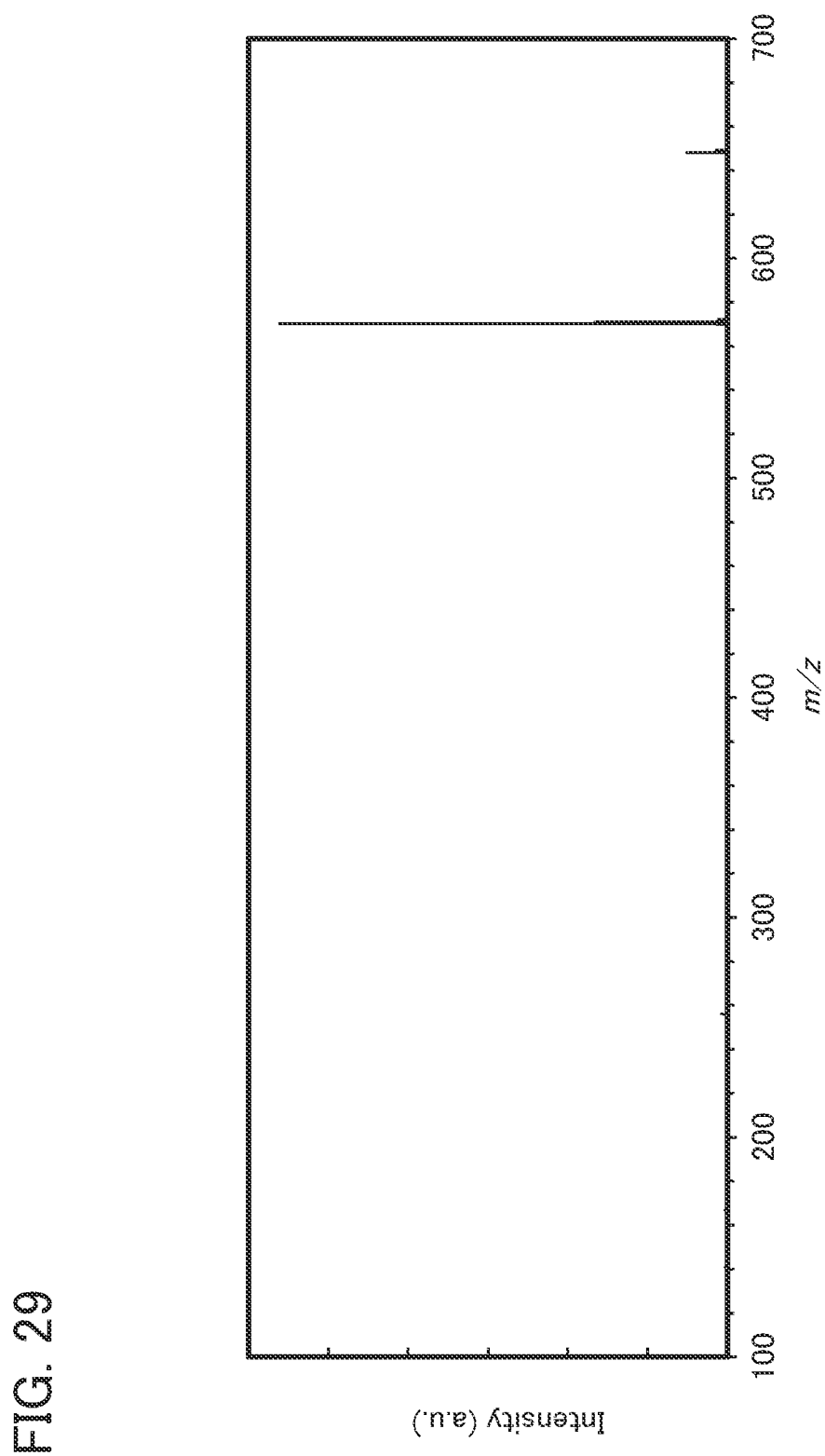
FIG. 29 shows an MS spectrum of F9BPPad.

By a PRM method, MS$^2$ measurement of m/z=648.13, which is an ion derived from F9BPPad, was performed. For setting of the PRM, the mass range of a target ion was set to m/z=648.13±2.0 (isolation window=4) and detection was performed in a positive mode. The measurement was performed with energy NCE (Normalized Collision Energy) for accelerating a target ion in a collision cell set to 20. The obtained MS spectrum is shown in FIG. 29.

Figure 30:
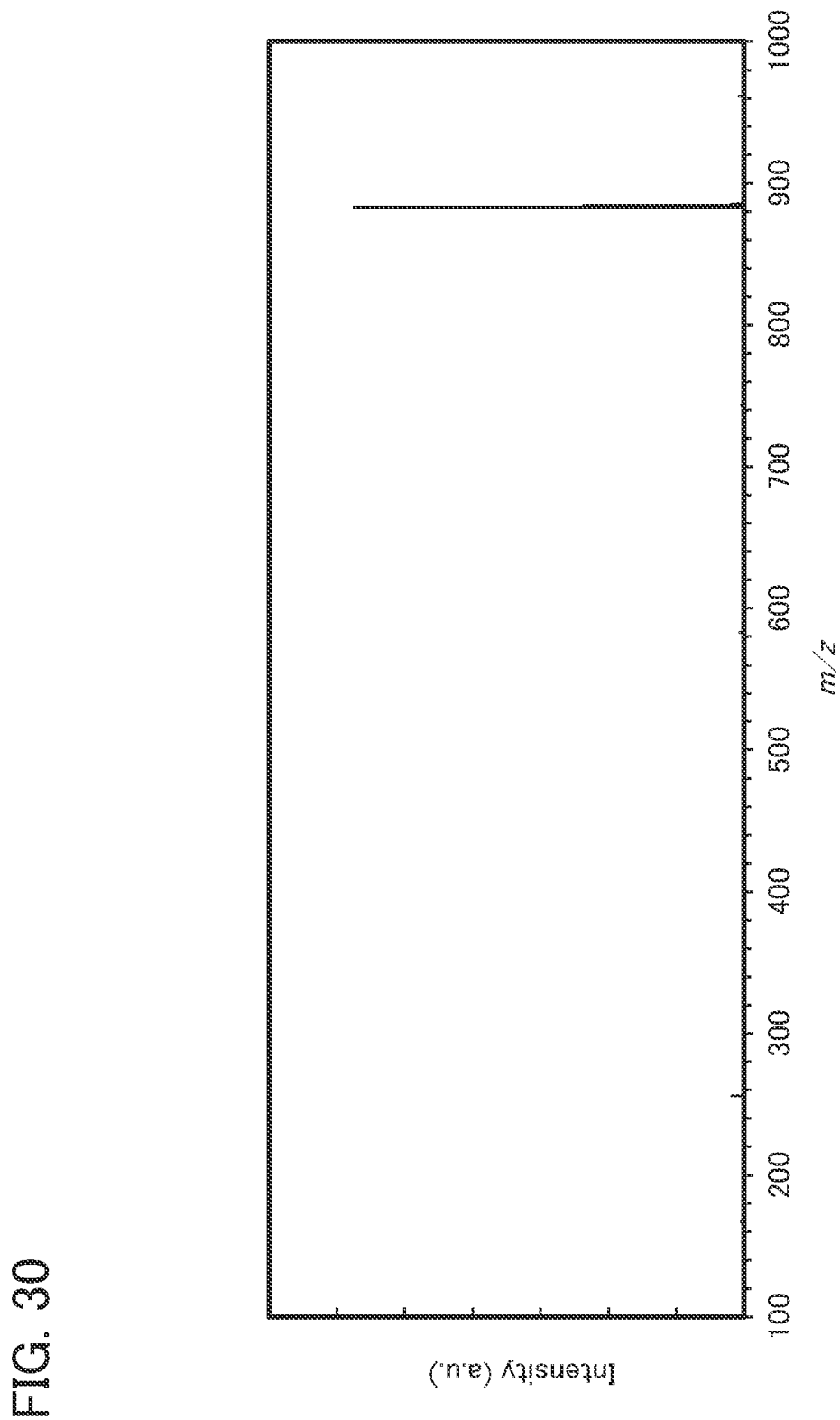
FIG. 30 shows an MS spectrum of Pad2F8BP.

By a PRM method, MS$^2$ measurement of m/z=961.28, which is an ion derived from Pad2F8BP, was performed. For setting of the PRM, the mass range of a target ion was set to m/z=961.28±2.0 (isolation window=4) and detection was performed in a positive mode. The measurement was performed with energy NCE (Normalized Collision Energy) for accelerating a target ion in a collision cell set to 30. The obtained MS spectrum is shown in FIG. 30.

Example 2

In this example, an EL device of one embodiment of the present invention described in the above embodiments and a comparative EL device are described. The structural formulae of organic compounds used in this example are shown below.

[Chemical Formulae 32]
(100)
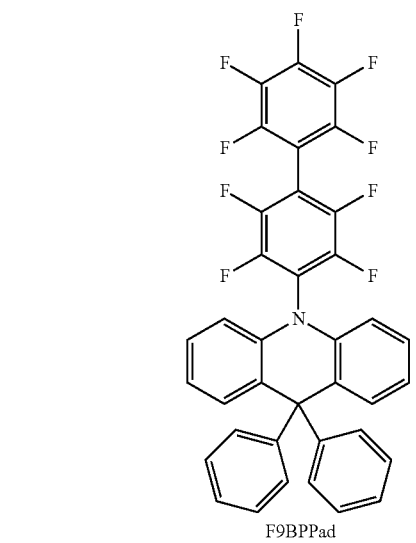
F9BPPad
(i)
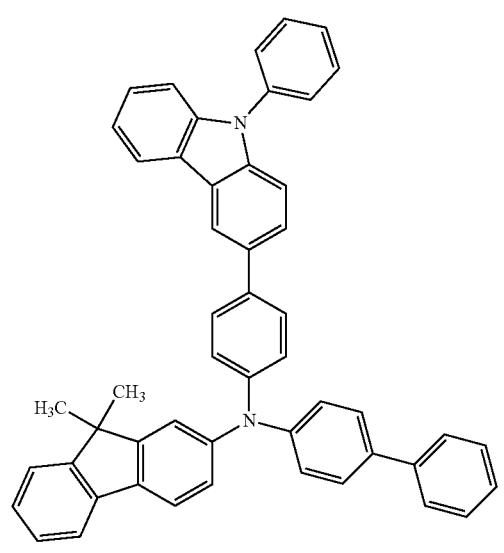
PCBBiF
(ii)
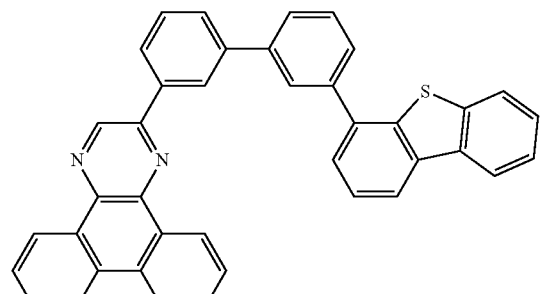
2mDBTBPDBq-II
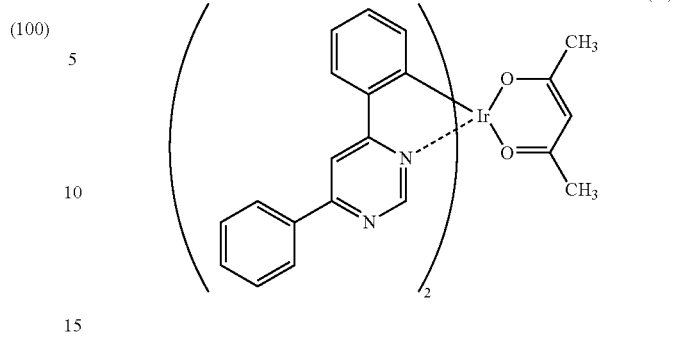
[Ir(dppm)$_2$(acac)]
(iii)
(200)
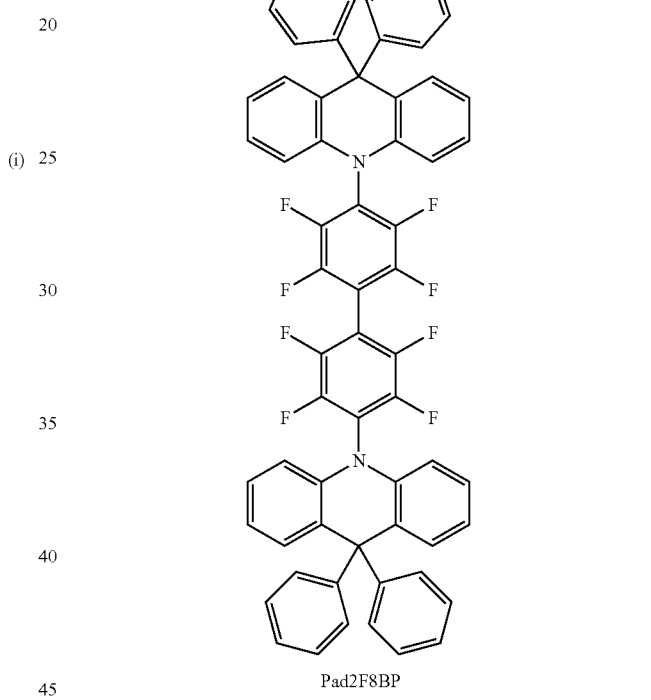
Pad2F8BP
(iv)
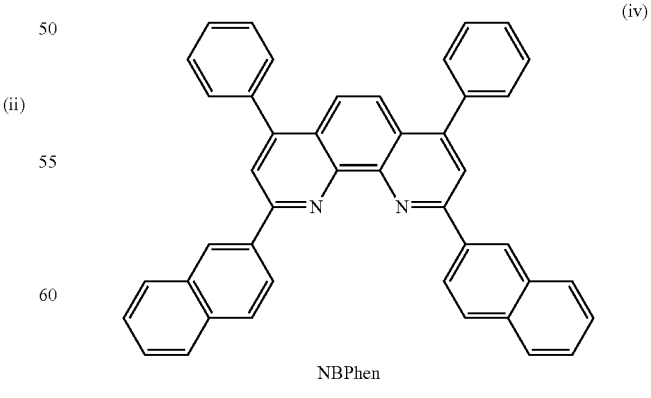
NBPhen

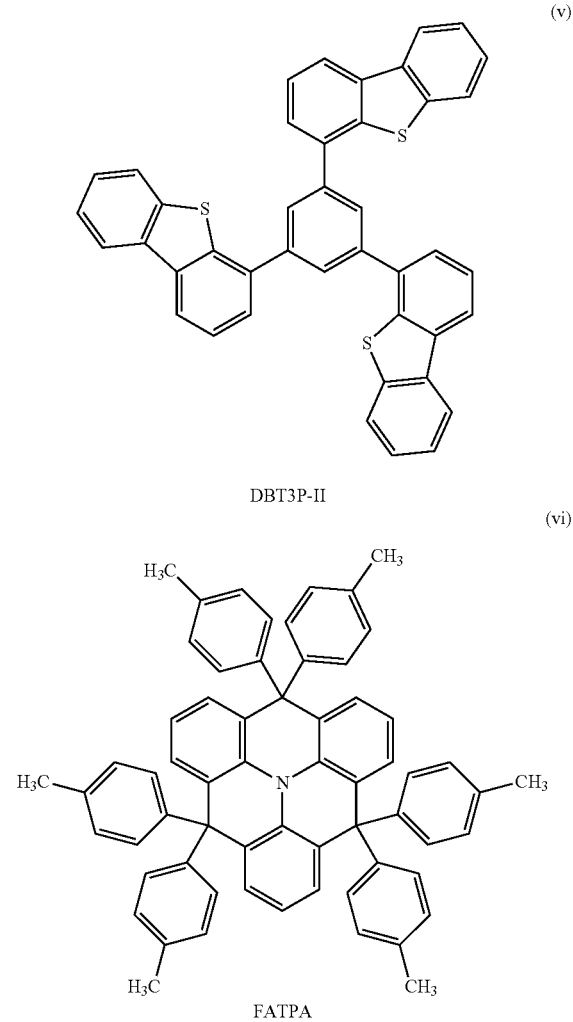

(v) DBT3P-II (vi) FATPA (Method for Fabricating EL Device 1-0)

First, indium tin oxide containing silicon oxide (ITSO) was deposited on a glass substrate by a sputtering method to form the anode 101. Note that the film thickness was 70 nm and the area of the electrode was 2 mm×2 mm.

Next, in pretreatment for forming the EL device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate on which the anode 101 was formed was fixed to a substrate holder provided in the vacuum evaporation apparatus such that the side on which the anode 101 was formed faced downward, and 10-(2,2',3,3',4',5,5',6,6'-nonafluoro-4-biphenylyl)9,9-diphenyl-9H,10H-acridine (abbreviation: F9BPPad) represented by Structural Formula (100) above and molybdenum(VI) oxide were deposited by co-evaporation on the anode 101 to have a weight ratio of 2:0.5 (=F9BPPad: MoOx) to a thickness of 50 nm by an evaporation method using resistance heating, whereby the hole-injection layer 111 was formed.

Next, on the hole-injection layer 111, N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (i) above was deposited by evaporation to a thickness of 20 nm, whereby the hole-transport layer 112 was formed.

Subsequently, 2-[3'-(dibenzothiophen-4-yl)biphenyl-3-yl]dibenzo[f,h]quinoxaline (abbreviation: 2mDBTBPDBq-II) represented by Structural Formula (ii) above, PCBBiF, and (acetylacetonato)bis(4,6-diphenylpyrimidinato)iridium(III) (abbreviation: [Ir(dppm)$_2$(acac)]) represented by Structural Formula (iii) above were deposited by co-evaporation to a thickness of 20 nm at a weight ratio of 0.7:0.3:0.06 (=2mDBTBPDBq-II: PCBBiF: [Ir(dppm)$_2$(acac)]), and then deposited by co-evaporation to a thickness of 20 nm at a weight ratio of 0.8:0.2:0.06 (=2mDBTBPDBq-II: PCBBiF: [Ir(dppm)$_2$(acac)]), whereby the light-emitting layer 113 was formed.

After that, on the light-emitting layer 113, 2mDBTBPDBq-II was deposited by evaporation to a thickness of 30 nm, and then 2,9-bis(naphthalen-2-yl)-4,7-diphenyl-1,10-phenanthroline (abbreviation: NBPhen) represented by Structural Formula (iv) above was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the cathode 102, whereby an EL device 1-0 of this example was fabricated.

(Method for Fabricating EL Device 1-1 to EL Device 1-3)

An EL device 1-1 was fabricated in a manner similar to that for the EL device 1-0 except that the hole-injection layer 111 of the EL device 1-0 was formed by depositing F9BPPad and molybdenum(VI) oxide by co-evaporation to a thickness of 50 nm at a weight ratio of 2:0.5 (=F9BPPad: molybdenum oxide), and then depositing 4,4',4"-(benzene-1,3,5-triyl)tri(dibenzothiophene) (abbreviation: DBT3P-II) represented by Structural Formula (v) above and molybdenum(VI) oxide by co-evaporation to a thickness of 5 nm at a weight ratio of 2:0.5 (=DBT3P-II: molybdenum oxide).

An EL device 1-2 was fabricated in a manner similar to that for the EL device 1-1 except that the layer of the EL device 1-1 formed by depositing DBT3P-II and molybdenum oxide by co-evaporation was formed to a thickness of 10 nm.

An EL device 1-3 was fabricated in a manner similar to that for the EL device 1-1 except that the layer of the EL device 1-1 formed by depositing DBT3P-II and molybdenum oxide by co-evaporation was formed to a thickness of 15 nm.

(Method for fabricating EL device 2-0 to EL device 2-3)

An EL device 2-0 was fabricated in a manner similar to that for the EL device 1-0 except that 10,10'-(2,2',3,3',5,5',6,6'-octafluorobiphenylen-4,4'-diyl)bis(9,9-diphenyl-9H,10H-acridine) (abbreviation: Pad2F8BP) represented by Structural Formula (200) above was used instead of F9BPPad used for the hole-injection layer 111 of the EL device 1-0.

An EL device 2-1, an EL device 2-2, and an EL device 2-3 were fabricated using Pad2F8BP instead of F9BPPad for the EL device 1-1, the EL device 1-2, and the EL device 1-3, respectively.

(Method for Fabricating Comparative EL Device 1-0 to Comparative EL Device 1-3)

A comparative EL device 1-0 was fabricated in a manner similar to that for the EL device 1-0 except that DBT3P-II was used instead of F9BPPad used for the hole-injection layer 111 of the EL device 1-0.

A comparative EL device 1-1, a comparative EL device 1-2, and a comparative EL device 1-3 were fabricated using DBT3P-II instead of F9BPPad for the EL device 1-1, the EL device 1-2, and the EL device 1-3, respectively.

(Method for Fabricating Comparative EL Device 2-0 to Comparative EL Device 2-3)

A comparative EL device 2-0 was fabricated in a manner similar to that for the EL device 1-0 except that 4,4,8,8,12,12-hexa-p-tolyl-4H-8H-12H-12C-aza-dibenzo[cd,mn]pylene (abbreviation: FATPA) represented by Structural Formula (vi) above was used instead of F9BPPad used for the hole-injection layer 111 of the EL device 1-0.

A comparative EL device 2-1, a comparative EL device 2-2, and a comparative EL device 2-3 were fabricated using FATPA instead of F9BPPad for the EL device 1-1, the EL device 1-2, and the EL device 1-3, respectively.

The element structures of the EL device 1-0 to the EL device 1-3, the EL device 2-0 to the EL device 2-3, the comparative EL device 1-0 to the comparative EL device 1-3, and the comparative EL device 2-0 to the comparative EL device 2-3 are listed in the following table.

DBT3P-II, and FATPA. Note that examples of a refractive index n includes a refractive index of an ordinary ray, n ordinary, a refractive index of an extraordinary ray, n extraordinary, and the average of them, n average. In this specification, the simple term "refractive index" may be rephrased as n average when anisotropy analysis is not performed, and as n ordinary when anisotropy analysis is performed. Note that n average is a value obtained by dividing the sum of n extra-ordinary and 2 n Ordinary by 3. Note that DBT3P-II is a material that can obtain favorable characteristics when used as an electron-donating material in the hole-injection layer.

Figure 18:
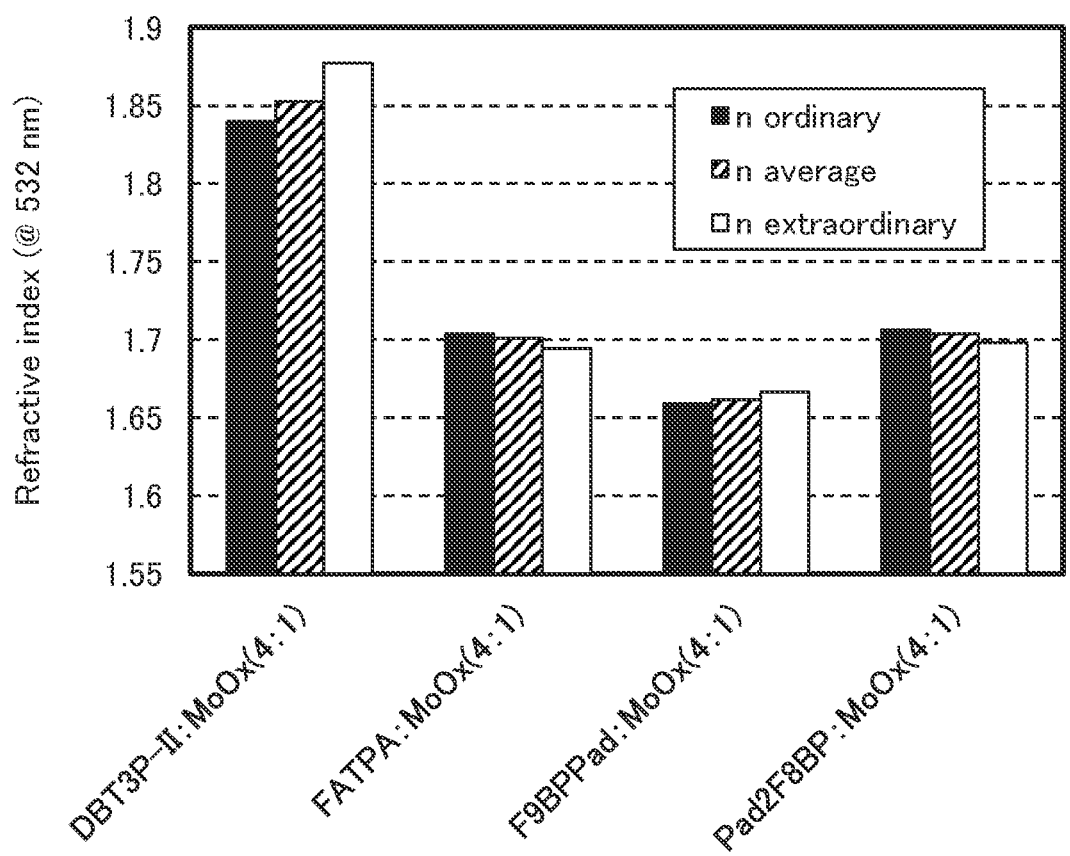
FIG. 18 is a graph showing refractive indexes of composite materials using F9BPPad, Pad2F8BP, DBT3P-II, and FATPA.

As shown in FIG. 18, the composite material using F9BPPad or Pad2F8BP is a low refractive index material, and the EL device of one embodiment of the present invention includes a hole-transport layer formed using the composite material and thus is an EL device including a hole-transport layer with a low refractive index. Note that the refractive index of another organic compound used for an EL device is approximately 1.70 to 1.90.

Figure 21:
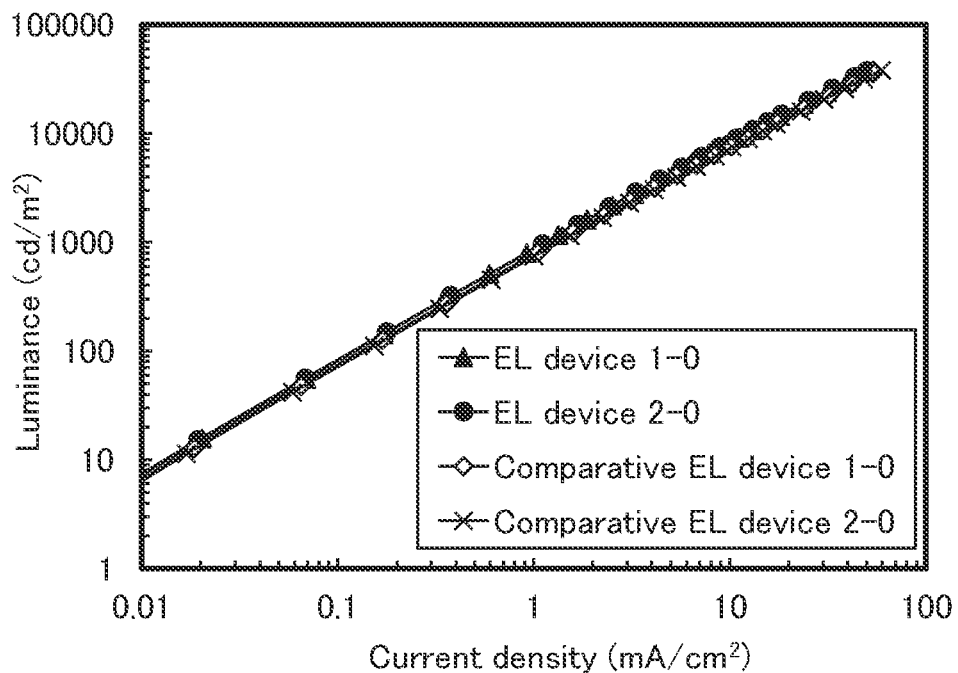
FIG. 21 shows luminance-current density characteristics of an EL device 1-0, an EL device 2-0, a comparative EL device 1-0, and a comparative EL device 2-0.
Figure 22:
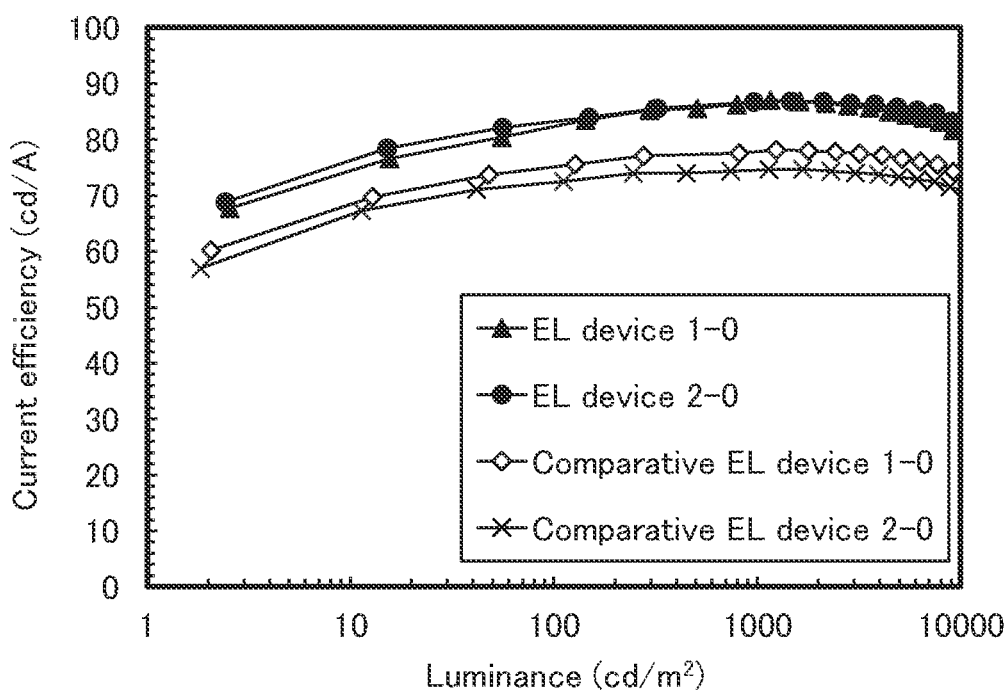
FIG. 22 shows current efficiency-luminance characteristics of the EL device 1-0, the EL device 2-0, the comparative EL device 1-0, and the comparative EL device 2-0.
Figure 23:
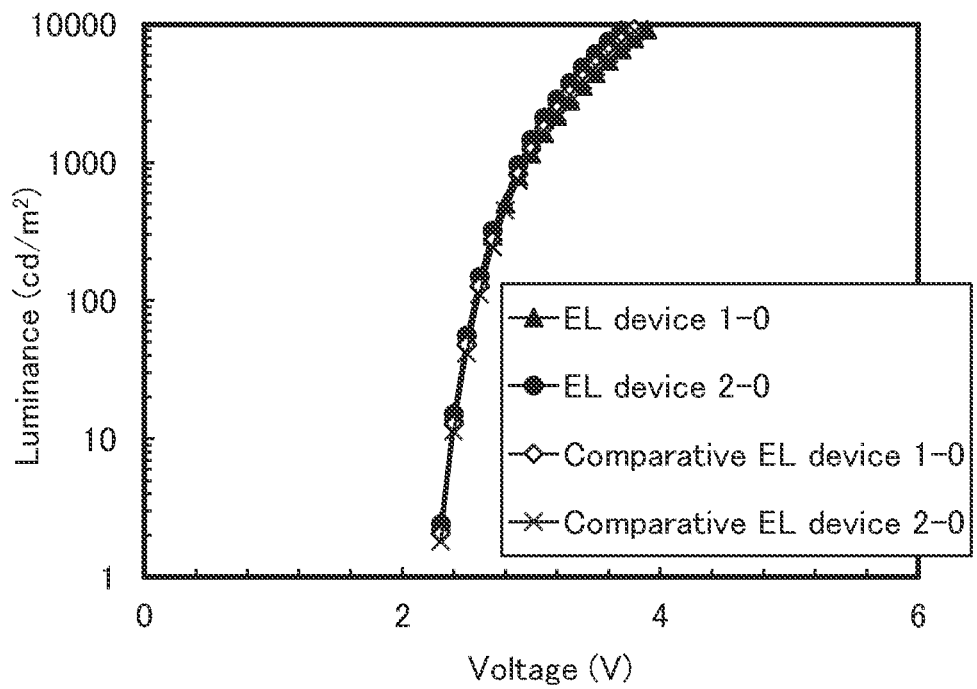
FIG. 23 shows luminance-voltage characteristics of the EL device 1-0, the EL device 2-0, the comparative EL device 1-0, and the comparative EL device 2-0.
Figure 24:
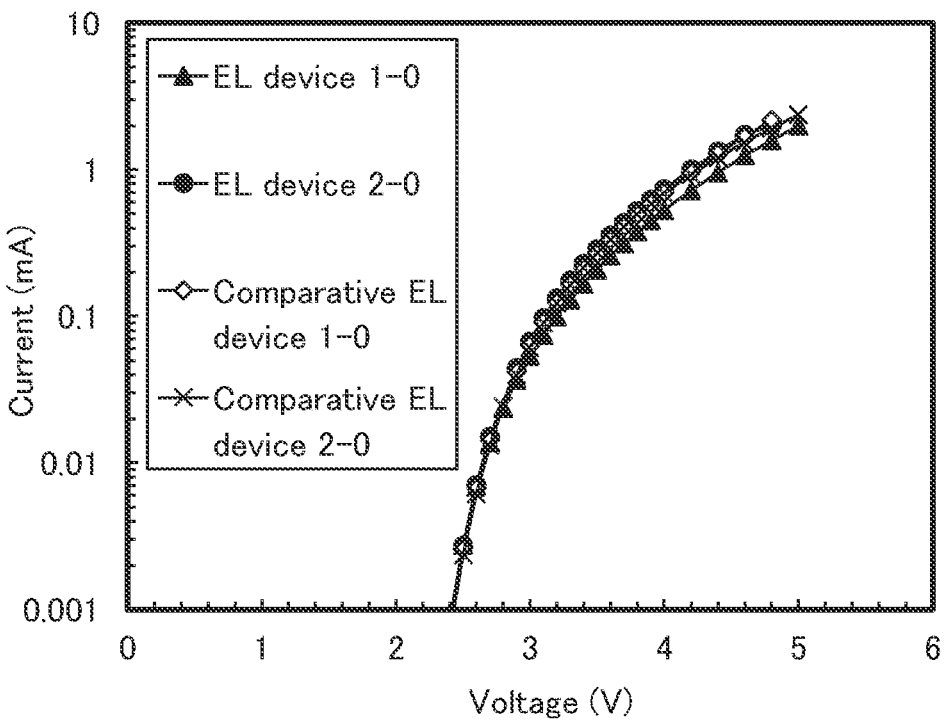
FIG. 24 shows current-voltage characteristics of the EL device 1-0, the EL device 2-0, the comparative EL device 1-0, and the comparative EL device 2-0.
Figure 25:
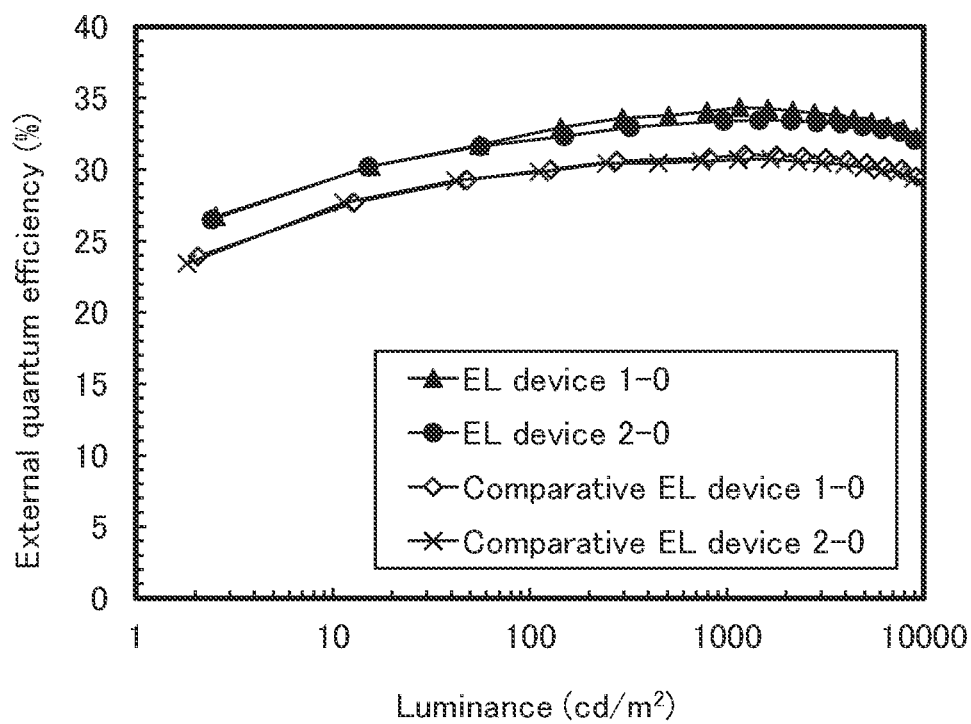
FIG. 25 shows external quantum efficiency-luminance characteristics of the EL device 1-0, the EL device 2-0, the comparative EL device 1-0, and the comparative EL device 2-0.
Figure 26:
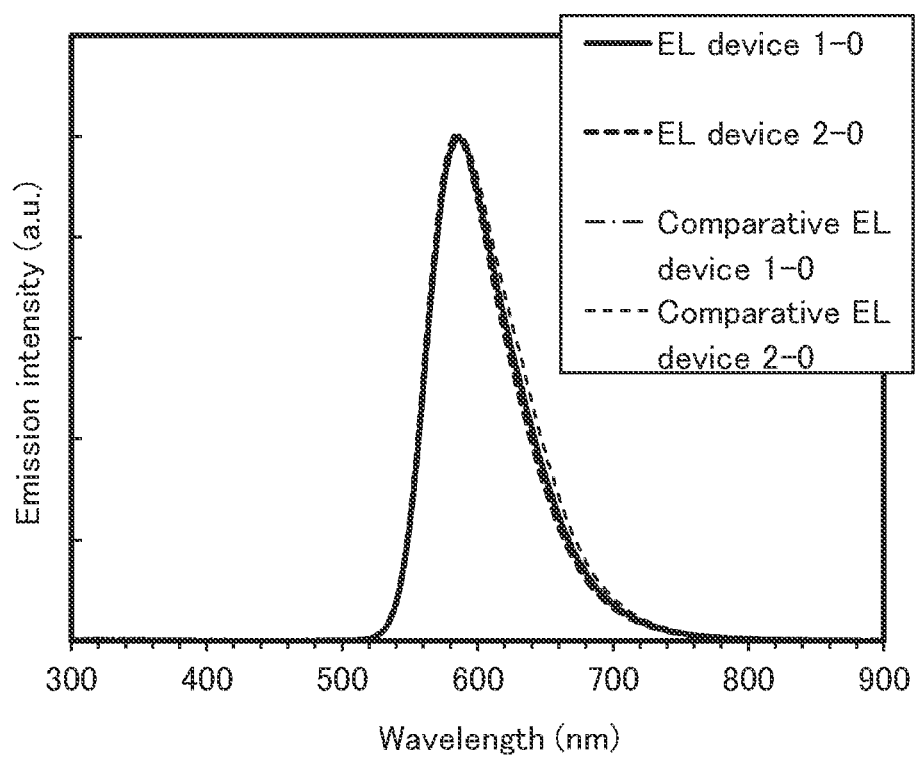
FIG. 26 shows emission spectra of the EL device 1-0, the EL device 2-0, the comparative EL device 1-0, and the comparative EL device 2-0.

FIG. 21 shows the EL device 1-0, the EL device 2-0, the comparative EL device 1-0, and the comparative EL device 2-0; FIG. 22, the current efficiency-luminance characteristics; FIG. 23, the luminance-voltage characteristics; FIG. 24, the current-voltage characteristics; FIG. 25, the external quantum efficiency-luminance characteristics; and FIG. 26, the emission spectra.

TABLE 1

| | | Thickness | EL device 1-X | EL device 2-X | Comparative EL device 1-X | Comparative EL device 2-X |
|---|---|---|---|---|---|---|
| Hole-injection layer | 1 | 50 nm | F9BPPad:MoOx (2:0.5) | Pad2F8BP:MoOx (2:0.5) | DBT3P-II:MoOx (2:0.5) | FAIPA:MoOx (2:0.5) |
| | 2 | *1 | | DBT3P-II:MoOx (2:0.5) | | |
| Hole-transport layer | | 20 nm | | PCBBiF | | |
| Light-emitting layer | 1 | 20 nm | | 2mDBTBPDBq-II:PCBBiF:Ir(dppm)₂(acac) (0.7:0.3:0.06) | | |
| | 2 | 20 nm | | 2mDBTBPDBq-II:PCBBiF:Ir(dppm)₂(acac) (0.8:0.2:0.06) | | |
| Electron-transport layer | 1 | 30 nm | | 2mDBTBPDBq-II | | |
| | 2 | 10 nm | | NBPhen | | |
| Electron-injection layer | | 1 nm | | LiF | | |

*1 X = 0:0 nm, X = 2:5 nm, X = 3:10 nm, X = 4:15 nm

These EL devices were subjected to sealing with a glass substrate (a sealant was applied to surround the elements, followed by UV treatment and one-hour heat treatment at 80° C. at the time of sealing) in a glove box containing a nitrogen atmosphere so that the EL devices are not exposed to the air, and then the initial characteristics and reliability of these EL devices were measured. Note that the glass substrate over which the EL device was formed was not subjected to particular treatment for improving outcoupling efficiency.

FIG. 18 shows the measurement results of refractive indexes of composite materials using F9BPPad, Pad2F8BP, Table 2 shows main characteristics at around 1000 cd/m² of the EL device 1-0 to the EL device 1-3, the EL device 2-0 to the EL device 2-3, the comparative EL device 1-0 to the comparative EL device 1-3, and the comparative EL device 2-0 to the comparative EL device 2-3. Note that luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

TABLE 2

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| EL device 1-0 | 3.0 | 0.05 | 1.3 | 0.5612 | 0.4375 | 87.0 | 34.3 |
| EL device 1-1 | 3.0 | 0.05 | 1.2 | 0.5662 | 0.4323 | 79.1 | 32.5 |

TABLE 2-continued

|  | Voltage (V) | Current (mA) | Current density (mA/cm²) | Chromaticity x | Chromaticity y | Current efficiency (cd/A) | External quantum efficiency (%) |
|---|---|---|---|---|---|---|---|
| EL device 1-2 | 3.0 | 0.05 | 1.2 | 0.5686 | 0.4297 | 73.1 | 28.9 |
| EL device 1-3 | 3.1 | 0.07 | 1.8 | 0.5716 | 0.4271 | 65.4 | 28.7 |
| EL device 2-0 | 2.9 | 0.04 | 1.1 | 0.5573 | 0.4412 | 86.7 | 33.4 |
| EL device 2-1 | 2.9 | 0.04 | 1.0 | 0.5625 | 0.4349 | 81.3 | 32.4 |
| EL device 2-2 | 3.0 | 0.06 | 1.5 | 0.5676 | 0.4312 | 74.0 | 30.7 |
| EL device 2-3 | 3.0 | 0.06 | 1.5 | 0.5702 | 0.4283 | 68.1 | 29.2 |
| Comparative EL device 1-0 | 2.9 | 0.04 | 1.1 | 0.5561 | 0.4412 | 77.5 | 30.8 |
| Comparative EL device 1-1 | 3.0 | 0.06 | 1.6 | 0.5602 | 0.4385 | 73.0 | 29.9 |
| Comparative EL device 1-2 | 3.0 | 0.06 | 1.6 | 0.5669 | 0.4317 | 66.6 | 28.0 |
| Comparative EL device 1-3 | 3.0 | 0.06 | 1.5 | 0.5678 | 0.4307 | 62.0 | 26.8 |
| Comparative EL device 2-0 | 3.0 | 0.06 | 1.5 | 0.5667 | 0.4320 | 74.6 | 30.7 |
| Comparative EL device 2-1 | 3.0 | 0.06 | 1.5 | 0.5696 | 0.4290 | 68.2 | 29.1 |
| Comparative EL device 2-2 | 3.0 | 0.06 | 1.6 | 0.5720 | 0.4265 | 62.3 | 27.3 |
| Comparative EL device 2-3 | 3.0 | 0.06 | 1.5 | 0.5730 | 0.4254 | 56.5 | 25.5 |

It was found from FIG. 21 to FIG. 26 that the EL device 1-0 and the EL device 2-0 of embodiments of the present invention are EL devices having driving characteristics similar to those of the comparative EL device 1-0 and the comparative EL device 2-0 and having favorable emission efficiency.

Note that in this example, the EL devices are fabricated using the materials with different refractive indexes, so that the EL devices have different optical distances between electrodes although the EL devices are fabricated to have the same thickness. Furthermore, fabrication of an EL device by evaporation has difficulty in precise control of the thicknesses; thus, an element is not fabricated to an assumed thickness in some cases.

In the EL device of this example, a large amount of light is reflected on the cathode because aluminum is used as the cathode and a certain amount of light is reflected on the anode due to a difference in refractive index; thus, the EL device has a structure in which light is amplified or attenuated by interference. Which wavelength of light is interfered or amplified depends on the optical distance between the electrodes in principle.

Here, the substance has its specific emission spectrum; therefore, amplification is efficiently performed when the amplification is performed at a wavelength with high emission intensity, and the emission efficiency is increased. Meanwhile, in the case where light of a wavelength with low emission intensity is amplified, the efficiency is decreased compared to the aforementioned case. That is, emission efficiency is increased or decreased also depending on the optical distance between the electrodes.

As described above, in this example, the optical distances between the electrodes are different because materials with different refractive indexes are used and precise control of the thickness is difficult; thus, emission efficiencies cannot be strictly compared in FIG. 25.

Figure 27:
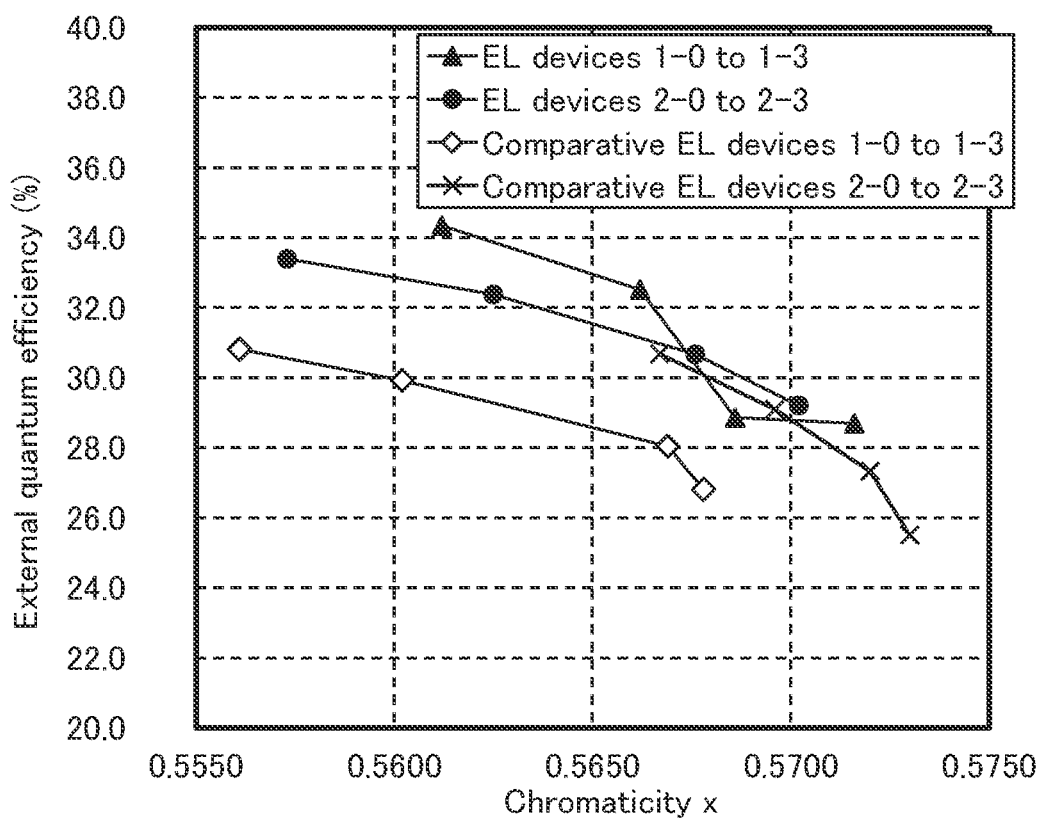
FIG. 27 shows the relation between a chromaticity x and external quantum efficiency at around 1000 cd/m$^2$ of EL devices of Example and EL devices that are comparative examples.

In view of the above, FIG. 27 shows a diagram showing the relation between the chromaticity x and external quantum efficiency at around 1000 cd/m² of the EL device 1-0 to the EL device 1-3, the EL device 2-0 to the EL device 2-3, the comparative EL device 1-0 to the comparative EL device 1-3, and the comparative EL device 2-0 to the comparative EL device 2-3.

The reason why the horizontal axis represents the chromaticity x is as follows: the interference effect depends on the optical distance between electrodes, and lights emitted using similar light-emitting substances and subjected to similar interference effects show similar emission spectra; thus, lights with the same chromaticity can be regarded as being subjected to the same interference effect, which indicate the optical distances between the electrodes are the same.

In other words, with reference to FIG. 27, the improvement in emission efficiency owing to the layer with a low refractive index can be simply examined, without considering the difference in refractive index of the materials and the difference in optical distances derived from deposition operation.

As shown in FIG. 27, the EL devices 2-0 to 2-3 and the comparative EL devices 2-0 to 2-3 using Pad2F8BP and FATPA, which have similar refractive indexes, respectively show similar external quantum efficiencies at the same chromaticity. In addition, the EL devices 1-0 to 1-3 using F9BPPad with a lower refractive index show higher external quantum efficiency than the EL devices 2-0 to 2-3 and the comparative EL devices 2-0 to 2-3, and obtain an effect of making efficiency, at maximum, 15% higher than those of the comparative EL devices 1-0 to 1-3 using DBT3P-II, which has a normal refractive index as an organic compound used as an organic compound for an EL device.

As shown in Table 2, the EL devices of embodiments of the present invention are EL devices having favorable driving characteristics with no significant deterioration of driving voltage and the like.

Figure 28:
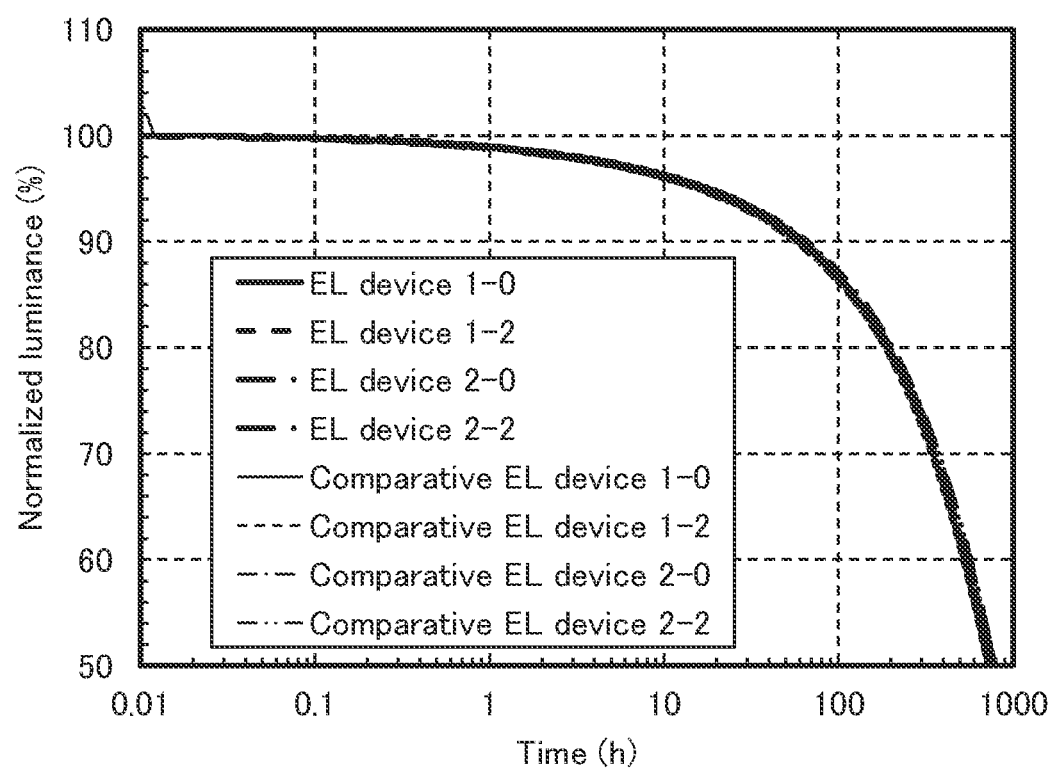
FIG. 28 shows normalized luminance-time change characteristics of the EL devices of Example and the EL devices that are comparative examples.

FIG. 28 shows a diagram showing luminance change with respect to driving time when the EL device 1-0, the EL device 1-2, the EL device 2-0, the EL device 2-2, the comparative EL device 1-0, the comparative EL device 1-2, the comparative EL device 2-0, and the comparative EL device 2-2 are driven at a constant current of 2 mA. FIG. 28 shows no big difference in luminance change among the EL devices, which reveals that the EL devices of embodiments of the present invention are EL devices having high emission efficiency while keeping a long lifetime.

REFERENCE NUMERALS

101: anode, 102: cathode, 103: EL layer, 111: hole-injection layer, 112: hole-transport layer, 113: light-emitting layer, 114: electron-transport layer, 115: electron-injection layer, 116: charge-generation layer, 117: p-type layer, 118: electron-relay layer, 119: electron-injection buffer layer, 400: substrate, 401: anode, 403: EL layer, 404: cathode, 405: sealant, 406: sealant, 407: sealing substrate, 412: pad, 420: IC chip, 501: anode, 502: cathode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealant, 607: space, 608: wiring, 609: FPC (flexible printed circuit), 610: element substrate, 611: switching FET, 612: current control FET, 613: anode, 614: insulator, 616: EL layer, 617: cathode, 618: EL device, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: anode, 1024R: anode, 1024G: anode, 1024B: anode, 1025: partition, 1028: EL layer, 1029: cathode, 1031: sealing substrate, 1032: sealant, 1033: transparent base material, 1034R: red coloring layer, 1034G: green coloring layer, 1034B: blue coloring layer, 1035: black matrix, 1036: overcoat layer, 1037: third interlayer insulating film, 1040: pixel portion, 1041: driver circuit portion, 1042: peripheral portion, 2001: housing, 2002: light source, 2100: robot, 2110: arithmetic device, 2101: illuminance sensor, 2102: microphone, 2103: upper camera, 2104: speaker, 2105: display, 2106: lower camera, 2107: obstacle sensor, 2108: moving mechanism, 3001: lighting device, 5000: housing, 5001: display portion, 5002: second display portion, 5003: speaker, 5004: LED lamp, 5006: connection terminal, 5007: sensor, 5008: microphone, 5012: support, 5013: earphone, 5100: cleaning robot, 5101: display, 5102: camera, 5103: brush, 5104: operation button, 5150: portable information terminal, 5151: housing, 5152: display region, 5153: bend portion, 5120: dust, 5200: display region, 5201: display region, 5202: display region, 5203: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7401: housing, 7402: display portion, 7403: operation button, 7404: external connection port, 7405: speaker, 7406: microphone, 9310: portable information terminal, 9311: display panel, 9312: display region, 9313: hinge, 9315: housing

The invention claimed is:
1. A compound represented by Formula (G1),

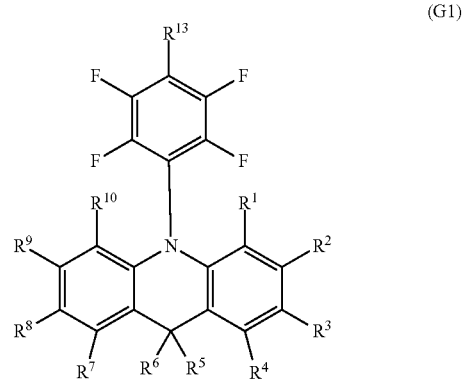

(G1)

wherein each of $R^1$ to $R^4$ and $R^7$ to $R^{10}$ independently represents any one of hydrogen, an alkyl group having 1 to 6 carbon atoms, and an alkyl fluoride group having 1 to 6 carbon atoms, wherein each of $R^5$ and $R^6$ represents an unsubstituted phenyl group, wherein $R^{13}$ represents a group represented by Formula (g1),

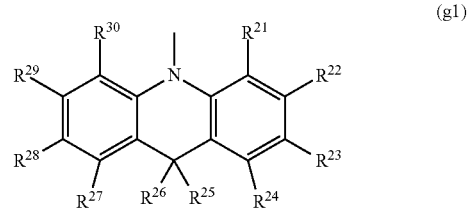

(g1)

wherein each of $R^{21}$ to $R^{24}$ and $R^{27}$ to $R^{30}$ independently represents any one of hydrogen, an alkyl group having 1 to 6 carbon atoms, and an alkyl fluoride group having 1 to 6 carbon atoms, and wherein each of $R^{25}$ and $R^{26}$ independently represent any one of hydrogen, an alkyl group having 1 to 6 carbon atoms, an alkyl fluoride group having 1 to 6 carbon atoms, and a substituted or unsubstituted phenyl group, and wherein a proportion of fluorine included in the compound is higher than or equal to 7 atomic % and lower than or equal to 40 atomic %.

2. A compound represented by Formula (G2),

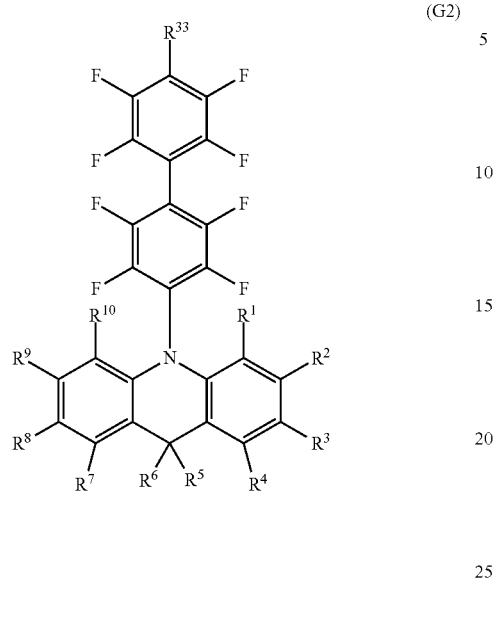

(G2)

wherein each of $R^1$ to $R^4$ and $R^7$ to $R^{10}$ independently represents any one of hydrogen, an alkyl group having 1 to 6 carbon atoms, and an alkyl fluoride group having 1 to 6 carbon atoms, wherein each of $R^5$ and $R^6$ represents an unsubstituted phenyl group, wherein $R^{33}$ represents a group represented by Formula (g1),

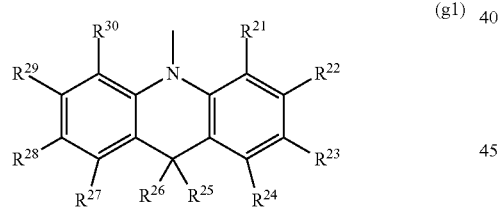

(g1)

wherein each of $R^{21}$ to $R^{24}$ and $R^{27}$ to $R^{30}$ independently represents any one of hydrogen, an alkyl group having 1 to 6 carbon atoms, and an alkyl fluoride group having 1 to 6 carbon atoms, and wherein each of $R^{25}$ and $R^{26}$ independently represent any one of hydrogen, an alkyl group having 1 to 6 carbon atoms, an alkyl fluoride group having 1 to 6 carbon atoms, and a substituted or unsubstituted phenyl group, and wherein a proportion of fluorine included in the compound is higher than or equal to 7 atomic % and lower than or equal to 40 atomic %.

3. The compound according to claim 2, wherein the compound is represented by Formula (200):

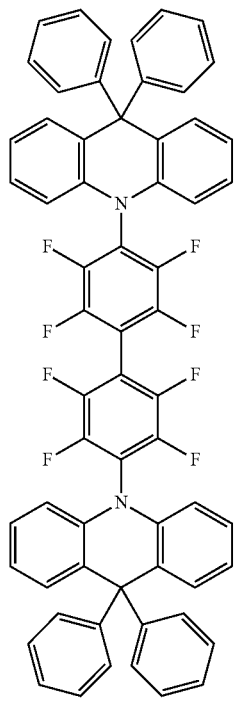

(200)

4. A light-emitting device comprising the compound according to claim 1.

5. A light-emitting device comprising:
a first electrode;
a first hole-injection layer over the first electrode, the first hole-injection layer comprising a compound; and
a second electrode over the first hole-injection layer,
wherein the compound comprises:
an acridine skeleton;
a first phenyl group bonded to a nitrogen atom in the acridine skeleton;
a first substituent bonded to the acridine skeleton; and
a second substituent bonded to the acridine skeleton,
wherein the first phenyl group is substituted by a fluorine atom,
wherein each of the first substituent and the second substituent independently represents any one of hydrogen, an alkyl group having 1 to 6 carbon atoms, a cyclohexyl group, an alkyl fluoride group having 1 to 6 carbon atoms, and a substituted or unsubstituted phenyl group, and
wherein a proportion of fluorine included in the compound is higher than or equal to 7 atomic % and lower than or equal to 40 atomic %.

6. The light-emitting device according to claim 5, wherein the first hole-injection layer further comprises a substance exhibiting an electron-accepting property with respect to the compound.

7. The light-emitting device according to claim 6,
wherein the substance exhibiting an electron-accepting property is an organic compound or any one of molybdenum oxide, vanadium oxide, ruthenium oxide, tungsten oxide and manganese oxide,
wherein the organic compound comprises a fused aromatic ring having a plurality of heteroatoms, and
wherein the fused aromatic ring is substituted with at least one of a cyano group and a halogen group.

8. The light-emitting device according to claim 5, wherein the first hole-injection layer is in contact with the first electrode.

9. The light-emitting device according to claim 6, further comprising a second hole-injection layer over the first hole-injection layer,
   wherein the second hole-injection layer comprises the substance exhibiting an electron-accepting property.

10. The light-emitting device according to claim 5, wherein the first hole-injection layer has a refractive index less than or equal to 1.8.

11. A light-emitting device comprising the compound according to claim 2.

* * * * *